United States Patent
Hecht et al.

(10) Patent No.: US 11,434,492 B2
(45) Date of Patent: Sep. 6, 2022

(54) RIBOSOME-MEDIATED INCORPORATION OF PEPTIDES AND PEPTIDOMIMETICS

(71) Applicants: Sidney Hecht, Phoenix, AZ (US); Larisa (Liza) Dedkova, Scottsdale, AZ (US); Rumit Maini, Tempe, AZ (US); Sandipan Roy Chowdhury, Tempe, AZ (US); Rakesh Paul, Baltimore, MD (US)

(72) Inventors: Sidney Hecht, Phoenix, AZ (US); Larisa (Liza) Dedkova, Scottsdale, AZ (US); Rumit Maini, Tempe, AZ (US); Sandipan Roy Chowdhury, Tempe, AZ (US); Rakesh Paul, Baltimore, MD (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/915,362

(22) Filed: Jun. 29, 2020

(65) Prior Publication Data
US 2020/0370057 A1 Nov. 26, 2020

Related U.S. Application Data

(62) Division of application No. 15/545,275, filed as application No. PCT/US2016/014548 on Jan. 22, 2016, now Pat. No. 10,745,705.

(60) Provisional application No. 62/106,958, filed on Jan. 23, 2015.

(51) Int. Cl.
| | |
|---|---|
| C12N 15/67 | (2006.01) |
| C12N 15/11 | (2006.01) |
| C07D 263/34 | (2006.01) |
| C07D 277/593 | (2006.01) |
| C12N 9/06 | (2006.01) |

(52) U.S. Cl.
CPC ........... *C12N 15/67* (2013.01); *C07D 263/34* (2013.01); *C07D 277/593* (2013.01); *C12N 9/003* (2013.01); *C12N 15/11* (2013.01); *C12Y 105/01003* (2013.01)

(58) Field of Classification Search
CPC ........ C12N 15/67; C12N 9/003; C12N 15/11; C07D 263/34; C07D 277/593; C12Y 105/01003
See application file for complete search history.

(56) References Cited

U.S. PATENT DOCUMENTS

2011/0117556 A1 5/2011 Liao
2016/0102140 A1 4/2016 Sierks

OTHER PUBLICATIONS

Amblard, M., et al. "Synthesis and characterization of bradykinin B2 receptor agonists containing constrained dipeptide mimics." Journal of medicinal chemistry 42.20 (1999): 4193-4201.
Bagley, M. C., et al. "Thiopeptide antibiotics." Chemical reviews 105.2 (2005): 685-714.
Bertram, A. et al. "Dendroamide A, Nostocyclamide and Related Cyclopeptides from Cyanobacteria. Total Synthesis, together with Organised and Metal-templated Assembly from Oxazole and Thiazolebased Amino Acids." Heterocycles 58 (2002): 521-561.
Chalfie, M., et al. "Green fluorescent protein as a marker for gene expression." Science 263.5148 (1994): 802-805.
Dedkova, L. M., "B-Puromycin Selection of Modified Ribosomes for In Vitro Incorporation of B-Amino Acids," Biochemistry, vol. 51, No. 1, pp. 401-415 (Jan. 10, 2012).
Dedkova, L. M., et al. "Construction of modified ribosomes for incorporation of D-amino acids into proteins." Biochemistry45.51 (2006): 15541-15551.
Dedkova, L. M., et al. "Enhanced D-amino acid incorporation into protein by modified ribosomes." Journal of the American Chemical Society 125.22 (2003): 6616-6617.
Dedkova, L. M., et al., "Enhanced D-Amino Acid Incorporation Into Protein by Modified Ribosomes," Journal of the American Chemical Society, vol. 125, No. 22, pp. 6616-6617 (May 10, 2003).
Erlacher, M. D., et al., "Efficient Ribosomal Peptidyl Transfer Critically Relies on the Presence of the Ribose 2'-OH at A2451 of 23S rRNA," Journal of the American Chemical Society, vol. 128, No. 13, pp. 4453-4459 (Apr. 1, 2006).
Extended European Search Report issued in related European Patent Application EP16740844, dated Sep. 11, 2018 (11 pp.).
Huynh, M. L., et al. "Tryptic digestion of in-gel proteins for mass spectrometry analysis." Two-dimensional electrophoresis protocols. Humana Press, 2009. 507-513.
Igarashi, Yasuhiro, et al. "Goadsporin, a chemical substance which promotes secondary metabolism and morphogenesis in *Streptomycetes*." The Journal of antibiotics54.12 (2001): 1045-1053.
International Search Report and Written Opinion issued in related International Application PCT/US2016/014548, dated May 6, 2016 (8 pp.).
Ivashkin, P. E., et al. "Synthesis and properties of chromophores of fluorescent proteins." Bioorganicheskaia khimiia 35.6 (2009): 726.
Janknecht, Ralf, et al. "Rapid and efficient purification of native histidine-tagged protein expressed by recombinant vaccinia virus." Proceedings of the National Academy of Sciences88.20 (1991): 8972-8976.

(Continued)

*Primary Examiner* — Iqbal H Chowdhury
(74) *Attorney, Agent, or Firm* — Quarles & Brady, LLP

(57) ABSTRACT

Modified ribosomes that were selected using a dipeptidyl-puromycin aminonucleoside are used to mediate site-specific incorporation of one or more peptides and peptidomimetics into protein in a cell free translation system. In addition, new fluorescent dipeptidomimetics have been synthesized and incorporated into proteins, as well as modified proteins containing one or more non-naturally occurring dipeptides.

4 Claims, 14 Drawing Sheets

Specification includes a Sequence Listing.

(56) References Cited

OTHER PUBLICATIONS

Liu, Chang C., et al. "Adding new chemistries to the genetic code." Annual review of biochemistry 79 (2010): 413-444.
Lodder, M. et al. "Chemical deprotection strategy for the elaboration of misacylated transfer RNA's." The Journal of Organic Chemistry 62.4 (1997): 778-779.
Lodder, M., et al. "Misacylated transfer RNAs having a chemically removable protecting group." The Journal of organic chemistry 63.3 (1998): 794-803.
Maini, R., "Study of Ribosomes Having Modifications in the Peptidyltransferase Center Using Non a-L-Amino Acids and Biological Evaluation of Topopyrones," Doctoral Dissertation, Arizona State University, pp. 1-144 (Retrieved on Apr. 9, 2016).
Maini, R., et al. "Incorporation of β-amino acids into dihydrofolate reductase by ribosomes having modifications in the peptidyltransferase center." Bioorganic & medicinal chemistry 21.5 (2013): 1088-1096.
Maini, R., et al. "Ribosome-mediated incorporation of dipeptides and dipeptide analogues into proteins in vitro." Journal of the American Chemical Society 137.35 (2015): 11206-11209.
O'Donnell, M. J. et al. "A mild and efficient route to Schiff base derivatives of amino acids." The Journal of Organic Chemistry 47.13 (1982): 2663-2666.
Pereyre, S., "Chracterisation of In Vitro-Selected Mutants of Ureaplasma Parvum Resistant to Macrolides and Related Antibiotics," International Journal of Antimicrobial Agents, Elsevier, Amsterdam, vol. 29, No. 2, pp. 207-211 (2007).
Phillips, A. J., et al. "Synthesis of functionalized oxazolines and oxazoles with DAST and Deoxo-Fluor." Organic letters 2.8 (2000): 1165-1168.
Polacek, N. et al. "The ribosomal peptidyl transferase center: structure, function, evolution, inhibition." Critical reviews in biochemistry and molecular biology 40.5 (2005): 285-311.
Robertson, S. A. et al. "A general and efficient route for chemical aminoacylation of transfer RNAs." Journal of the American Chemical Society 113.7 (1991): 2722-2729.
Robertson, S. A., et al. "The use of 5'-pbospho-2 deoxyribocytidylylriboadenosine as a facile route to chemical aminoacylation of tRNA." Nucleic acids research 17.23 (1989): 9649-9660.
Sanz-Cervera, J. F., et al. "Solution versus fluorous versus solid-phase synthesis of 2, 5-disubstituted 1, 3-azoles. Preliminary antibacterial activity studies." The Journal of organic chemistry 74.23 (2009): 8988-8996.
Singh, E. K. et al. "Total synthesis of trans, trans-sanguinamide B and conformational isomers." Organic letters 14.5 (2012): 1198-1201.
Tang, T. et al. "A flexible approach to (S)-3-amino-2-pyrrolidinone derivatives." Heterocycles 64 (2004): 121-128.
Tsien, R. Y. "Constructing and exploiting the fluorescent protein paintbox (Nobel Lecture)." Angewandte Chemie International Edition 48.31 (2009): 5612-5626.
Tsien, R. Y. "The green fluorescent protein" Annu. Rev. Biochem. 1998, 67, 509.
Vizan, J. L., et al. "The peptide antibiotic microcin B17 induces double-strand cleavage of DNA mediated by *Escherichia coli* DNA gyrase." The EMBO journal 10.2 (1991): 467-476.
Wahyudi, H., et al. "Synthesis, Structure-Activity Analysis, and Biological Evaluation of Sanguinamide B Analogues." The Journal of organic chemistry 77.23 (2012): 10596-10616.
Wang, B., et al. "Tandemly activated tRNAs as participants in protein synthesis." Journal of Biological Chemistry 281.20 (2006): 13865-13868.
Wang, L., et al. "Unnatural amino acid mutagenesis of green fluorescent protein." The Journal of organic chemistry 68.1 (2003): 174-176.
Wipf, P. et al. "A new synthesis of highly functionalized oxazoles." The Journal of Organic Chemistry58.14 (1993): 3604-3606.
Wipf, P. et al. "Total synthesis of westiellamide." Journal of the American Chemical Society114.27 (1992): 10975-10977.

B

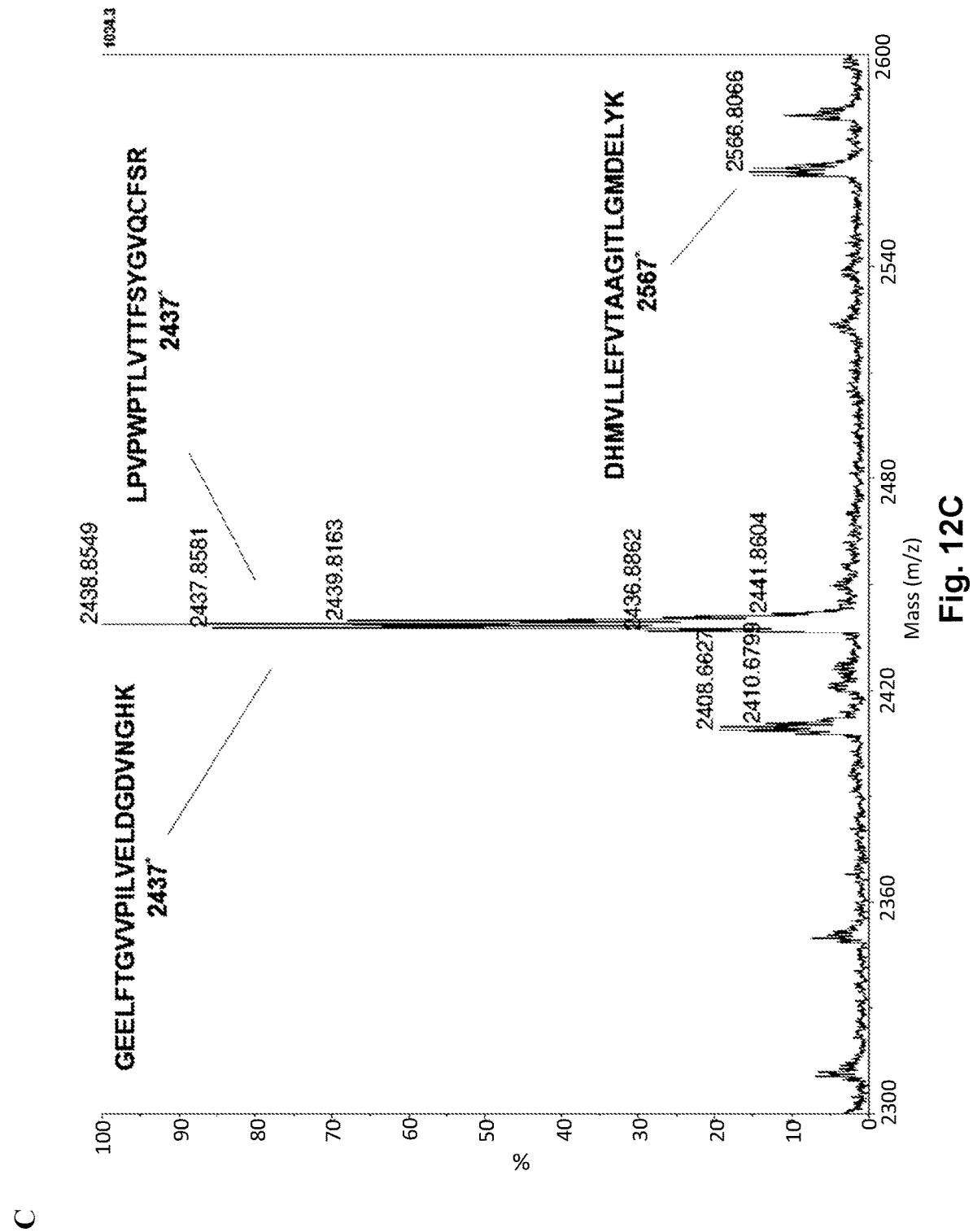

```
                            SEQUENCE LISTING

<160> NUMBER OF SEQ ID NOS: 20

<210> SEQ ID NO 1
<211> LENGTH: 15
<212> TYPE: PRT
<213> ORGANISM: Artificial Sequence
<220> FEATURE:
<223> OTHER INFORMATION: SYNTHETIC
<220> FEATURE:
<221> NAME/KEY: Xaa
<222> LOCATION: (13)..(13)
<223> OTHER INFORMATION: Xaa is dipeptidomimetic 6

<400> SEQUENCE: 1

Phe Ser Val Ser Gly Glu Gly Glu Gly Asp Ala Thr Xaa Gly Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: SYNTHETIC

<400> SEQUENCE: 2
```

Phe Ser Val Ser Gly Glu Gly Glu Gly Asp Ala Thr Tyr Gly Lys
1               5                   10                  15

<210> SEQ ID NO 3
<211> LENGTH: 21
<212> TYPE: PRT
<213> ORGANISM: Artificial Sequence
<220> FEATURE:
<223> OTHER INFORMATION: SYNTHETIC

<400> SEQUENCE: 3

Leu Pro Val Pro Trp Pro Thr Leu Val Thr Thr Phe Ser Tyr Gly Val
1               5                   10                  15

Gln Cys Phe Ser Arg
            20

<210> SEQ ID NO 4
<211> LENGTH: 23
<212> TYPE: PRT
<213> ORGANISM: Artificial Sequence
<220> FEATURE:
<223> OTHER INFORMATION: SYNTHETIC

<400> SEQUENCE: 4

Gly Glu Glu Leu Phe Thr Gly Val Val Pro Ile Leu Val Glu Leu Asp
1               5                   10                  15

Gly Asp Val Asn Gly His Lys
            20

<210> SEQ ID NO 5
<211> LENGTH: 21
<212> TYPE: PRT
<213> ORGANISM: Artificial Sequence
<220> FEATURE:
<223> OTHER INFORMATION: SYNTHETIC

<400> SEQUENCE: 5

Leu Pro Val Pro Trp Pro Thr Leu Val Thr Thr Phe Ser Gly Gly Val
1               5                   10                  15

Gln Cys Phe Ser Arg
            20

<210> SEQ ID NO 6
<211> LENGTH: 21
<212> TYPE: PRT
<213> ORGANISM: Artificial Sequence
<220> FEATURE:
<223> OTHER INFORMATION: SYNTHETIC
<220> FEATURE:
<221> NAME/KEY: Xaa
<222> LOCATION: (14)..(14)
<223> OTHER INFORMATION: Xaa is dipeptidomimetic 6

<400> SEQUENCE: 6

Leu Pro Val Pro Trp Pro Thr Leu Val Thr Thr Phe Ser Xaa Gly Val
1               5                   10                  15

Gln Cys Phe Ser Arg
            20

<210> SEQ ID NO 7
<211> LENGTH: 8
<212> TYPE: PRT
<213> ORGANISM: Artificial Sequence
<220> FEATURE:
<223> OTHER INFORMATION: SYNTHETIC

```
<400> SEQUENCE: 7

Val Tyr Glu Gln Phe Leu Pro Lys
1               5

<210> SEQ ID NO 8
<211> LENGTH: 11
<212> TYPE: PRT
<213> ORGANISM: Artificial Sequence
<220> FEATURE:
<223> OTHER INFORMATION: SYNTHETIC

<400> SEQUENCE: 8

Asn Thr Leu Asn Lys Pro Val Ile Met Gly Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: SYNTHETIC

<400> SEQUENCE: 9

Met Ile Ser Leu Ile Ala Ala Leu Ala Phe Asp Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: SYNTHETIC

<400> SEQUENCE: 10

Asn Ile Ile Leu Ser Ser Gln Pro Gly Thr Asp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: SYNTHETIC

<400> SEQUENCE: 11

His Thr Trp Glu Ser Ile Gly Arg Pro Leu Pro Gly Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: SYNTHETIC

<400> SEQUENCE: 12

Met Ile Ser Leu Ile Ala Ala Leu Ala Gly Phe Asp Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: SYNTHETIC
```

```
<400> SEQUENCE: 13

Asn Ile Ile Leu Ser Ser Gln Pro Gly Thr Asp Asp Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: SYNTHETIC
<220> FEATURE:
<221> NAME/KEY: Xaa
<222> LOCATION: (10)..(10)
<223> OTHER INFORMATION: Xaa is dipeptidomimetic 5

<400> SEQUENCE: 14

Met Ile Ser Leu Ile Ala Ala Leu Ala Xaa Asp Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: SYNTHETIC

<400> SEQUENCE: 15

His Thr Trp Glu Ser Ile Gly Arg Pro Leu Pro Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: SYNTHETIC
<220> FEATURE:
<221> NAME/KEY: Xaa
<222> LOCATION: (10)..(10)
<223> OTHER INFORMATION: Xaa is dipeptidomimetic 6

<400> SEQUENCE: 16

Met Ile Ser Leu Ile Ala Ala Leu Ala Xaa Asp Arg
1               5                   10

<210> SEQ ID NO 17
<211> LENGTH: 9
<212> TYPE: PRT
<213> ORGANISM: Artificial Sequence
<220> FEATURE:
<223> OTHER INFORMATION: SYNTHETIC

<400> SEQUENCE: 17

Phe Glu Gly Asp Thr Leu Val Asn Arg
1               5

<210> SEQ ID NO 18
<211> LENGTH: 11
<212> TYPE: PRT
<213> ORGANISM: Artificial Sequence
<220> FEATURE:
<223> OTHER INFORMATION: SYNTEHTIC

<400> SEQUENCE: 18

Ser Ala Met Pro Glu Gly Tyr Val Gln Gln Arg
1               5                   10
```

```
<210> SEQ ID NO 19
<211> LENGTH: 16
<212> TYPE: PRT
<213> ORGANISM: Artificial Sequence
<220> FEATURE:
<223> OTHER INFORMATION: SYNTEHTIC

<400> SEQUENCE: 19

Leu Glu Tyr Asn Phe Asn Ser His Asn Val Tyr Ile Met Ala Asp Lys
1               5                   10                  15

<210> SEQ ID NO 20
<211> LENGTH: 23
<212> TYPE: PRT
<213> ORGANISM: Artificial Sequence
<220> FEATURE:
<223> OTHER INFORMATION: SYNTHETIC

<400> SEQUENCE: 20

Asp His Met Val Leu Leu Glu Phe Val Thr Ala Ala Gly Ile Thr Leu
1               5                   10                  15

Gly Met Asp Glu Leu Tyr Lys
            20
```

RIBOSOME-MEDIATED INCORPORATION OF PEPTIDES AND PEPTIDOMIMETICS

CROSS REFERENCE

This application is a divisional application of U.S. application Ser. No. 15/545,275, filed Jul. 20, 2017, which is a 371 application of PCT/US2016/014548 filed Jan. 22, 2016, which claims priority to U.S. provisional patent application 62/106,958 filed on Jan. 23, 2015, which are incorporated herein by reference as if set forth in their entirety.

FEDERALLY SPONSORED RESEARCH OR DEVELOPMENT

This invention was made with government support under R01 GM103861 awarded by the National Institutes of Health. The government has certain rights in the invention.

REFERENCE TO A SEQUENCE LISTING SUBMITTED VIA EFS-WEB

The content of the ASCII text file of the sequence listing named "112624_01209_ST25.txt" which is 40 KB in size was created on Jun. 28, 2020 and electronically submitted via EFS-Web herewith the application is incorporated herein by reference in its entirety.

FIELD OF THE INVENTION

This disclosure relates to modified ribosomes used to mediate site-specific incorporation of peptides and peptidomimetics into protein in a cell free translation system, as well as to the creation of novel fluorescent dipeptidomimetics and novel fluorescent proteins having a fluorescent peptidomimetic.

BACKGROUND OF THE INVENTION

Peptide and protein engineering have long been desired. Irrespective of the approach, the engineered chemical structure is designed to advantageously adjust the molecular properties such as, stability or biological activity. This can have a role in the development of drug-like compounds from existing peptides and peptidomimetics.

SUMMARY OF THE INVENTION

Embodiments disclosed herein relate to a genetically modified ribosome having a 23S rRNA sequence modification, for example, the modification for clone groups 1-9 in Table 1.

Other embodiments relate to methods for the selection of modified ribosomes able to incorporate any dipeptide and dipeptidomimetic using a dipeptidyl or dipeptidomimetic puromycin derivative.

Further embodiments relate to in vitro translation systems and methods for producing a modified peptide, polypeptide, or protein that utilize a genetically modified ribosome having a 23S rRNA sequence modification selected from the combinations and permutations found in Table 5.

These and other aspects of the embodiments disclosed herein will be apparent upon reference to the following detailed description and figures.

BRIEF DESCRIPTION OF THE DRAWINGS

FIG. 12C depicts the MALDI-MS of tryptic fragments of wt GFP, mass range 2300-2600 Da; Serine-tyrosine-glycine residues are in red (grayscale in blank and white reproductions).

DETAILED DESCRIPTION OF THE INVENTION

Figure 1:
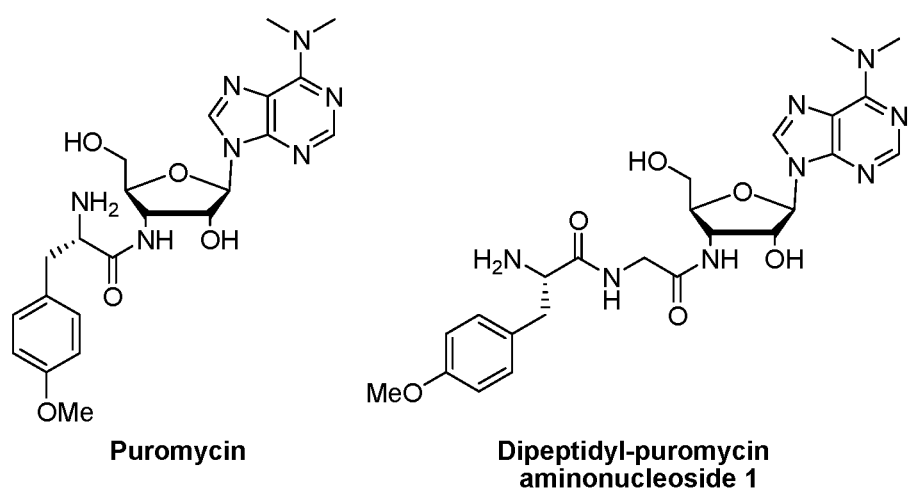
FIG. 1 depicts the structures of puromycin and dipeptidyl-puromycin aminonucleoside 1.

The embodiments herein described relate to a novel set of modified ribosomes (Table 1), which were selected using a dipeptidyl-puromycin aminonucleoside (FIG. 1), following a strategy similar to that described previously.[1] For the first time, it is demonstrated that modified ribosome mediated site-specific incorporation of three dipeptides and five dipeptidomimetics (FIG. 2) into protein using a single amber codon in the mRNA transcript in a cell free translation system is achieved.

Figure 2:
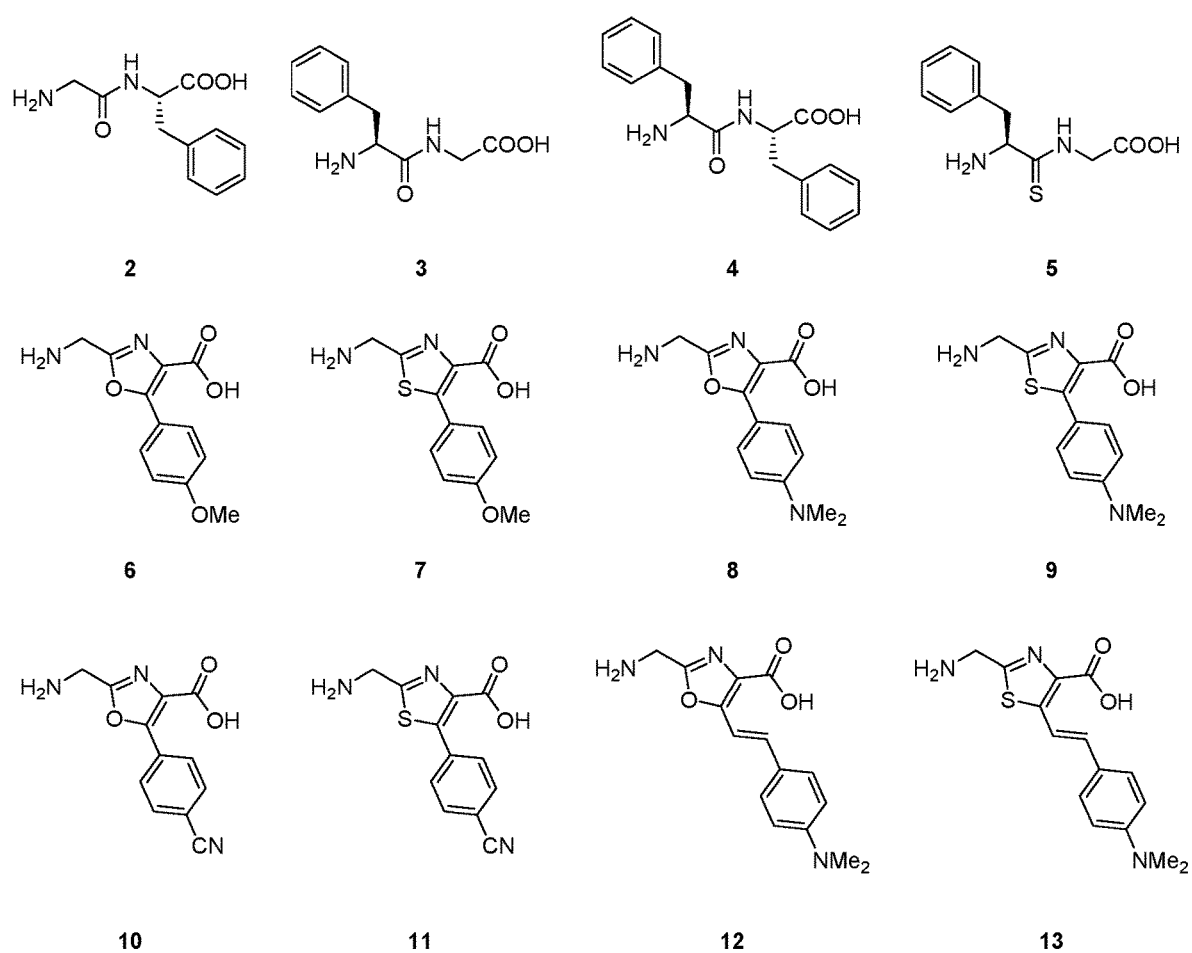
FIG. 2 shows the structures of dipeptides 2-4 and dipeptidomimetics 5-13.

In another inventive aspect, eight novel fluorescent dipeptidomimetics 6-13, which are stable structural analogues of GFP-chromophore, are disclosed (see FIG. 2).

In the examples described below, four dipeptidomimetics were incorporated into *E. coli* dihydrofolate reductase (DHFR) at position 10. Modified DHFRs bearing dipeptide 2, dipeptidomimetics 5 or 6 were authenticated by MALDI-TOF mass spectrometry of tryptic digests. Moreover, an artificial fluorescent protein having dipeptidomimetic 6, which gave 20-fold enhanced fluorescent intensity relative to wild-type blue fluorescent protein (BFP), was also prepared.

Further examples are directed to other dipeptidomimetics and related proteins, compounds, and methods.

EXAMPLES

Experimental (for the chemical structures corresponding to the numeric references below, see Schemes 1-8 at the end of the Detailed Description).

Synthesis of Puromycin and pdCpA Derivatives (S)-methyl-2-(2-(((9H-fluoren-9-yl)methoxy)carbonyl)-3-(4-methoxyphenyl)propanamido)acetate (15). To an ice-cold slurry of 0.60 g (1.59 mmol) of 14 and 0.20 g (1.59 mmol) of glycine methyl ester in 6.6 mL of anhydrous CH$_3$CN, 0.5 mL (3.5 mmol) of Et$_3$N and 0.62 g (1.65 mmol) of HBTU were added. The mixture was stirred at room temperature for 2 h. After the completion of the reaction, the resulting solution was poured into brine and extracted with 100 mL of ethyl acetate.

The pooled extracts were successively washed with 1 N HCl and saturated NaHCO$_3$, dried (anhydrous MgSO$_4$) and evaporated under reduced pressure to afford the crude product. The residue was purified by flash chromatography on a silica gel column (15×2 cm). Elution with 1:1 ethyl acetate-hexanes afforded 15 as white solid: yield 0.77 g (95%). Silica gel TLC R$_f$=0.65 (4:1 chloroform-methanol); $^1$H NMR (DMSO-d$_6$) δ 2.72 (t, 1H, J=9.2 Hz), 2.96 (q, 1H, J=8.4 Hz), 3.63 (s, 3H), 3.67 (s, 3H), 3.89 (m, 2H), 4.12 (m, 3H), 4.25 (m, 1H), 6.79-6.81 (d, 2H, J=8.4 Hz), 7.22-7.23 (d, 2H, J=6.4 Hz), 7.29 (m, 2H), 7.40 (m, 2H), 7.62 (m, 3H) 7.86-7.88 (d, 2H, J=6 Hz), and 8.47 (t, 1H, J=4.4 Hz); $^{13}$C NMR (DMSO-d$_6$) δ 37.0, 46.9, 52.1, 55.3, 56.7, 66.1, 113.9, 120.5, 125.7, 125.8, 127.4, 128.0, 128.0, 130.4, 130.6, 141.0, 141.0, 144.1, 144.2, 156.2, 158.1, 170.6, and 172.6; mass spectrum (APCI), m/z 489.2026 (M+H)$^+$ (C$_{28}$H$_{29}$N$_2$O$_6$ requires m/z 488.5317).

(S)-2-(2-(((9H-fluoren-9-yl)methoxy)carbonyl)-3-(4-ethoxyphenyl)propanamido)acid (16). To an ice-cold solution of 0.15 g (0.29 mmol) of 15 in 3 mL of THF, a solution of 13.5 mg (0.66 mmol) of LiOH in 3 mL water was added drop wise (over 10 minutes). The reaction mixture was stirred at room temperature while being monitored by silica gel TLC. After disappearance of starting material, the pH of the reaction mixture was adjusted to 3 with 0.3 M HCl.

The resulting mixture was then extracted with 10 mL of ethyl acetate, dried (anhydrous MgSO$_4$) and concentrated under reduced pressure. The residue was purified by flash chromatography on a silica gel column (15×2 cm). Elution with 1:4 ethyl acetate-hexanes afforded 16 as a white solid: yield 87.0 mg (60%); Silica gel TLC R$_f$=0.4 (1:1 ethyl acetate-hexanes). $^1$H NMR (CD$_3$OD) δ 2.81 (t, 1H, J=9.2 Hz), 3.14 (q, 1H, J=8.4 Hz), 3.69 (s, 3H), 3.91 (m, 2H), 4.15 (m, 3H), 4.33 (m, 1H), 6.78-6.80 (d, 2H, J=8.4 Hz), 7.15-7.17 (d, 2H, J=6.4 Hz), 7.29 (m, 2H), 7.39 (m, 2H), 7.56 (m, 3H) 7.77-7.79 (d, 2H, J=6 Hz), 8.22 (t, 1H, J=4.4 Hz), and 9.33 (br s, 1H); $^{13}$C NMR (CD$_3$OD) δ 36.8, 40.5, 54.2, 56.5, 66.6, 113.4, 119.4, 124.8, 124.9, 126.7, 126.7, 127.3, 129.1, 129.9, 141.1, 141.1, 143.8, 143.8, 156.8, 158.5, 171.3 and 173.1; mass spectrum (APCI), m/z 475.1867 (M+H)$^+$ (C$_{27}$H$_{27}$N$_2$O$_6$ requires m/z 474.1791).

9-[3"-Deoxy-3"-(N-Fmoc-4-O-methyl-(S)-tyrosylglycyl)-β-D-ribofuranosyl]-6-(N,N'-dimethylamino)purine (17). To an ice-cold mixture of 103 mg (0.21 mmol) 16 and 35.0 mg (0.30 mmol) N-hydroxysuccinimide in 3 mL of dry CH$_2$Cl$_2$, under argon environment, 61.0 mg (0.30 mmol) DCC dissolved in 3 mL dry CH$_2$Cl$_2$ was added drop wise. The reaction was stirred at room temperature for 18 h. The reaction mixture was then concentrated under diminished pressure and suspended in CH$_3$CN (Side product DCU is least soluble in CH$_3$CN). The suspension was the filtered. The filtrate was concentrated under reduced pressure. The resulting solid was crystallized from hot hexane and used in the next reaction without further purification.

To a solution of 14.0 mg (24.0 μmol) of this crude intermediate and 4.70 mg (16.0 μmol) of puromycin aminonucleoside in 0.8 mL of dry DMF was added 3.00 μL (2.40 mg; 24.0 μmol) of Et$_3$N. The reaction mixture was stirred at 25° C. for 3.5 h and then concentrated under diminished pressure. The residue was purified by flash chromatography on a silica gel column (15×2 cm). Elution with 15:1 chloroform-methanol afforded 17 as a colorless solid: yield 11.3 mg (94%); $^1$H NMR (500 MHz, DMSO-$d_6$) δ 2.73 (m, 1H), 2.97 (dd, 1H, J=13.7 and 3.7 Hz), 3.47 (br s, 6H). 3.68 (s, 3H), 3.74, (m, 1H), 3.82 (d, 2H, J=5.6 Hz), 4.04 (m, 1H), 4.17 (m, 4H), 4.50 (m, 2H), 6.01 (d, 1H, J=2.4 Hz), 6.80 (d, 2H, J=8.4 Hz), 7.21 (m, 2H), 7.29 (m, 2H), 7.39 (d, 2H, J=7.8 Hz), 7.63 (d, 3H, J=7.8 Hz), 7.87 (d, 2H, J=7.5 Hz), 7.96 (d, 1H, J=7.6 Hz), 8.25 (s, 1H), and 8.49 (s, 1H); $^{13}$C NMR (DMSO-$d_6$) δ 29.0, 36.5, 42.0, 46.5, 48.6, 50.3, 54.9, 56.5, 65.7, 73.2, 83.1, 89.4, 113.5, 119.6, 120.0, 125.30, 125.31, 127.0, 127.6, 130.0, 130.2, 138.1, 140.6, 140.6, 143.7, 143.8, 149.3, 151.1, 153.6, 155.9 157.7, 169.0, and 171.9; mass spectrum (APCI), m/z 751.3201 (M+H)$^+$ ($C_{39}H_{43}N_8O_8$ requires m/z 751.3204).

9-[3"-Deoxy-3"-(O-methyl-(S)-tyrosylglycyl)-β-D-ribofuranosyl]-6-(N,N" dimethylamino)purine(dipeptidylpuromycin) (1). A solution of 10 mg (13 μmol) of 17 in 1 mL of 5:1 DMF-piperidine was stirred at 25° C. for 40 min and concentrated under diminished pressure. The residue was purified by flash chromatography on a silica gel column (5×2 cm). Elution with 9:1 chloroform-methanol afforded 1 as a colorless solid: yield 3.1 mg (49%); $^1$H NMR (CD$_3$OD) δ 2.85 (m, 1H), 3.07 (m, 1H), 3.51 (s, 6H), 3.76 (m, 4H) 3.93 (m, 3H), 4.18 (m, 1H), 4.63 (m, 2H), 6.03 (d, 1H, J=3.0 Hz), 6.87 (d, 2H, J=8.5 Hz), 7.17 (d, 2H, J=8.6 Hz), 8.21 (s, 1H) and 8.36 (s, 1H); $^{13}$C NMR (CD$_3$OD) δ 39.0, 39.3, 43.3, 52.1, 55.7, 62.3, 68.6, 75.1, 85.0, 92.0, 106.4, 115.2, 121.6, 131.4, 139.2, 150.6, 153.0, 156.2, 160.4 and 171.6; mass spectrum (APCI), m/z 529.2530 (M+H)$^+$ ($C_{24}H_{33}N_8O_6$ requires m/z 529.2523).

(N-(4-Pentenoyl)glycyl)phenylalanine methyl ester (19). To a solution of 0.25 g (3.33 mmol) of glycine (18) in 10 mL of 10% aq Na$_2$CO$_3$ was added a solution of 1.31 g (6.66 mmol) of 4-pentenoylsuccinimide[4,5] in 10 mL of dioxane. The reaction mixture was stirred at 25° C. for 12 h. The mixture was acidified with 1 N aq HCl and aq layer was extracted with three 50-mL portions of ethyl acetate. The combined organic extract was dried (anhydrous MgSO$_4$) and concentrated under diminished pressure to afford the crude product.

The crude product was dissolved in 15 mL of dry DMF at 0° C., 1.90 g (4.98 mmol) of HBTU was added and resulting solution was stirred for 15 minutes. To this solution 1.10 g (4.99 mmol) of L-phenylalanine methyl ester and 1.40 mL (1.01 g, 9.98 mmol) of triethylamine in 5 mL of dry DMF was added. The reaction mixture was stirred at 25° C. for 5 h. The mixture was concentrated under diminished pressure and the residue was diluted with 80 mL of ethyl acetate. The organic layer was washed with two 40-mL portions of 1 N aq HCl, 40 mL of water and 20 mL of brine, then dried (anhydrous MgSO$_4$) and concentrated under diminished pressure. The residue was purified by flash chromatography on a silica gel column (20×3 cm). Elution with 4% methanol in dichloromethane afforded 19 as colorless oil: yield 0.50 g (47%); silica gel TLC $R_f$ 0.59 (9:1 chloroform-methanol); $^1$H NMR (CDCl$_3$) δ 2.28 (m, 4H), 3.02 (m, 2H), 3.64 (s, 3H), 3.86 (m, 2H), 4.78 (m, 1H), 4.97 (m, 2H), 5.76 (m, 1H), 7.01 (t, 1H, J=5.1 Hz), 7.09 (m, 2H), 7.19 (m, 3H) and 7.36 (d, 1H, J=8.0 Hz); $^{13}$C NMR (CDCl$_3$) δ 29.3, 35.1, 37.7, 42.9, 52.2, 53.4, 115.4, 126.9, 128.4, 129.1, 135.9, 136.8, 169.1, 171.7 and 173.0; mass spectrum (ESI), m/z 319.1655 (M+H)$^+$ ($C_{17}H_{23}N_2O_4$ requires m/z 319.1652).

(N-(4-Pentenoyl)glycyl)phenylalanine cyanomethyl ester (20). To a solution of 350 mg (1.10 mmol) of 19 in 10 mL of THF was added dropwise a solution of 105 mg (4.39 mmol) of LiOH in 5 mL of water at 0° C. The reaction mixture was stirred at 25° C. for 12 h, diluted with 30 mL of water and washed with two 15-mL portions of ether. The aqueous layer was acidified with 1 N aq HCl to pH ~2 and extracted with three 40-mL portions of ethyl acetate. The combined organic layer was dried (anhydrous MgSO$_4$) and concentrated under diminished pressure to obtain crude product.

The crude product was dissolved in 18 mL of anhydrous acetonitrile. To this solution was added 0.70 mL (0.51 g; 5.06 mmol) of Et$_3$N followed by 0.63 mL (0.53 g; 9.90 mmol) of chloroacetonitrile. The reaction mixture was stirred at room temperature for 16 h and then concentrated under diminished pressure. The residue was suspended in 80 mL of ether. The ether layer was washed successively with 40 mL of water, 40 mL of 1 N HCl and 30 mL of brine. The organic layer was dried (anhydrous MgSO$_4$) and concentrated under diminished pressure. The residue was purified by flash chromatography on a silica gel column (15×3 cm). Elution with 1:3 hexanes-ethyl acetate afforded the ester 20 as a colorless oil: yield 0.28 g (75%); silica gel TLC $R_f$ 0.67 (9:1 chloroform-methanol); $^1$H NMR (CDCl$_3$) δ 2.31 (m, 4H), 3.09 (m, 2H), 3.89 (m, 2H), 4.67 (m, 2H), 4.81 (m, 1H), 5.01 (m, 2H), 5.76 (m, 1H), 6.79 (m, 1H), 7.14 (d, 2H, J=7.7 Hz), 7.26 (m, 3H) and 7.44 (d, 1H, J=7.6 Hz); $^{13}$C NMR (CDCl$_3$) δ 29.3, 35.2, 37.5, 43.1, 49.0, 53.4, 114.0, 115.7, 127.4, 128.8, 129.2, 135.2, 136.8, 169.4, 170.2 and 173.3; mass spectrum (APCI), m/z 344.1607 (M+H)$^+$ ($C_{18}H_{22}N_2O_4$ requires m/z 344.1610).

N-(4-pentenoyl)glycyl)phenylalanyl-pdCpA (22). A solution containing 35 mg (0.1 mmol) of cyanomethyl ester 20 and 8.0 mg (5.9 μmol) of the tris(tetrabutylammonium) salt of pdCpA (21) in 100 μL of 9:1 DMF-Et$_3$N was subjected to sonication at room temperature for 2 h. After which time, the reaction mixture was purified by C$_{18}$ reversed phase HPLC (250×10 mm) using a gradient of 1%→65% acetonitrile in 50 mM ammonium acetate, pH 4.5, over a period of 45 min. The fractions eluting at 18.4 and 18.8 min were collected, combined and lyophilized to afford 22 as a colorless solid: yield 5.4 mg (100%); mass spectrum (ESI), m/z 921.2365 (M−H)$^-$ ($C_{35}H_{43}N_{10}O_{16}P_2$ requires m/z 921.2339).

(N-(4-Pentenoyl)phenylalanyl)glycine methyl ester (25). To a solution of 0.50 g (3.01 mmol) of L-phenylalanine (24) in 10 mL of 10% aq Na$_2$CO$_3$ was added a solution of 0.65 g (3.30 mmol) of pentenoylsuccinimide in 10 mL of dioxane. The reaction mixture was stirred at 25° C. for 24 h. The mixture was acidified with 1 N aq HCl and aq layer was extracted with three 50-mL portions of ethyl acetate. The combined organic extract was dried (anhydrous MgSO$_4$) and concentrated under diminished pressure to afford crude product.

The crude product was dissolved in 15 mL of dry DMF at 0° C., 1.25 g (3.30 mmol) of HBTU was added and resulting solution was stirred for 15 minutes. To this solution 0.25 g (3.30 mmol) of glycine methyl ester and 0.92 mL (0.67 g, 6.60 mmol) of triethylamine in 5 mL of dry DMF was added. The reaction mixture was stirred at 25° C. for 5 h. The mixture was concentrated under diminished pressure and the residue was diluted in 80 mL of ethyl acetate. The organic layer was washed with two 40-mL portions of 1 N aq HCl, 40 mL of water and 20 mL of brine, then dried (anhydrous MgSO$_4$) and concentrated under diminished pressure. The residue was purified by flash chromatography on a silica gel column (20×3 cm). Elution with 4% methanol in dichloromethane afforded 25 as colorless oil: yield 0.48 g (50%); silica gel TLC $R_f$ 0.5 (4% methanol in dichloromethane); $^1$H NMR (CDCl$_3$) δ 2.21-2.29 (m, 4H), 3.02-3.07 (m, 2H), 3.69 (s, 3H), 3.91-3.96 (m, 2H), 4.74-4.78 (m, 1H), 4.94-4.99 (m, 2H), 5.65-5.73 (m, 1H), 6.34 (d, 1H, J=8.0 Hz), 6.72 (s, 1H) and 7.17-7.28 (m, 5H); $^{13}$C NMR (CDCl$_3$) δ 29.3, 35.5, 38.1, 41.1, 52.3, 54.0, 115.6, 126.9, 128.6, 129.2, 136.5, 136.7, 169.7, 171.4 and 172.5; mass spectrum (APCI), m/z 319.1658 (M+H)$^+$ (C$_{17}$H$_{23}$N$_2$O$_4$ requires m/z 319.1652).

(N-(4-Pentenoyl)phenylalanyl)glycine cyanomethyl ester (26). To a solution of 50.0 mg (0.16 mmol) of 25 in 4 mL of 1:1 THF-water was added 0.32 mL (0.32 mmol) of 1 M aq LiOH at 0° C. The reaction mixture was stirred at room temperature for 24 h and neutralized carefully with 0.5 N HCl. The solution was concentrated under diminished pressure to obtain crude product.

The crude product was dissolved in 3 mL of anhydrous acetonitrile. To this solution was added 108 μL (79.0 mg; 0.78 mmol) of Et$_3$N followed by 0.50 mL (59.0 mg; 0.78 mmol) of chloroacetonitrile. The reaction mixture was stirred at room temperature for 24 h and then concentrated under diminished pressure. The residue was purified by flash chromatography on a silica gel column (20×2 cm). Elution with 1:3 hexanes-ethyl acetate afforded 26 as a colorless semi-solid: yield 33.0 mg (62%); silica gel TLC R$_f$ 0.4 (1:3 hexanes-ethyl acetate); $^1$H NMR (CDCl$_3$) δ 2.22-2.29 (m, 4H), 2.97-3.12 (m, 2H), 4.01 (t, 2H, J=5.6 Hz), 4.71 (s, 2H), 4.77-4.83 (m, 1H), 4.92-4.99 (m, 2H), 5.65-5.75 (m, 1H), 6.41 (d, 1H, J=8.0 Hz) and 7.14-7.28 (m, 6H); $^{13}$C NMR (CDCl$_3$) δ 29.3, 35.4, 37.9, 40.6, 53.9, 113.9, 115.7, 126.9, 128.6, 129.2, 136.4, 136.6, 168.1, 171.9 and 172.8; mass spectrum (APCI), m/z 344.1617 (M+H)$^+$ (C$_{18}$H$_{22}$N$_3$O$_4$ requires m/z 344.1610).

(N-(4-Pentenoyl)phenylalanyl)glycyl-pdCpA (27). A solution containing 10 mg (30 μmol) of cyanomethyl ester 26 and 5.3 mg (3.9 μmol) of the tris(tetrabutylammonium) salt of pdCpA (21) in 100 μL of 9:1 DMF-Et$_3$N was subjected to sonication at room temperature for 2 h. After which time, the reaction mixture was purified by C$_{18}$ reversed phase HPLC (250×10 mm) using a gradient of 1%→65% acetonitrile in 50 mM ammonium acetate, pH 4.5, over a period of 45 min. The fraction eluting at 18.6 min was collected and lyophilized to afford 27 as a colorless solid: yield 3.6 mg (100%); mass spectrum (ESI), m/z 921.2338 (M−H)$^-$ (C$_{35}$H$_{43}$N$_{10}$O$_{16}$P$_2$ requires m/z 921.2339).

(N-(4-Pentenoyl)phenylalanyl)phenylalanine methyl ester (29). To a solution of 0.50 g (3.01 mmol) of L-phenylalanine (24) in 10 mL of 10% aq Na$_2$CO$_3$ was added a solution of 0.65 g (3.30 mmol) of 4-pentenoylsuccinimide in 10 mL of dioxane. The reaction mixture was stirred at 25° C. for 24 h. The mixture was acidified with 1 N aq HCl and the aq layer was extracted with three 50-mL portions of ethyl acetate. The combined organic extract was dried (anhydrous MgSO$_4$) and concentrated under diminished pressure to afford crude product.

The crude product was dissolved in 15 mL of dry DMF at 0° C., 1.25 g (3.30 mmol) of HBTU was added and resulting solution was stirred for 15 minutes. To this solution 0.59 g (3.30 mmol) of phenylalanine methyl ester and 0.92 mL (0.67 g, 6.6 mmol) of triethylamine in 5 mL of dry DMF was added. The reaction mixture was stirred at 25° C. for 5 h. The mixture was concentrated under diminished pressure and the residue was diluted in 80 mL of ethyl acetate. The organic layer was washed with two 40-mL portions of 1 N aq HCl, 40 mL of water and 20 mL of brine, then dried (anhydrous MgSO$_4$) and concentrated under diminished pressure.

The residue was purified by flash chromatography on a silica gel column (20×3 cm). Elution with 4% methanol in dichloromethane afforded 29 as colorless oil: yield 0.75 g (61%); silica gel TLC R$_f$ 0.6 (2% methanol in dichloromethane); $^1$H NMR (CDCl$_3$) δ 2.16-2.27 (m, 4H), 2.93-3.06 (m, 4H), 3.62 (s, 3H), 4.72-4.85 (m, 2H), 4.89-4.99 (m, 2H), 5.64-5.73 (m, 1H), 6.72 (d, 1H, J=8.0 Hz), 6.98-7.03 (m, 3H) and 7.14-7.24 (m, 8H); $^{13}$C NMR (CDCl$_3$) δ 29.4, 35.4, 37.9, 38.4, 52.2, 53.6, 54.1, 115.5, 126.8, 127.0, 128.4, 128.5, 129.2, 129.4, 135.8, 136.6, 136.9, 171.1, 171.4 and 172.3; mass spectrum (APCI), m/z 409.2138 (M+H)$^+$ (C$_{24}$H$_{29}$N$_2$O$_4$ requires m/z 409.2127).

(N-(4-Pentenoyl)phenylalanyl)phenylalanine cyanomethyl ester (30). To a solution of 0.30 g (0.74 mmol) of 29 in 10 mL of 1:1 THF-water was added 2.20 mL (2.20 mmol) of 1 M aq LiOH in at 0° C. The reaction mixture was stirred at room temperature for 24 h, neutralized with 0.5 N HCl and concentrated under diminished pressure to afford crude product.

The crude product was dissolved in 5 mL of anhydrous DMF. To this solution was added 0.52 mL (0.37 g, 3.7 mmol) of Et$_3$N followed by 0.23 mL (0.28 g, 3.7 mmol) of chloroacetonitrile. The reaction mixture was stirred at room temperature for 24 h and then concentrated under diminished pressure. The residue was purified by flash chromatography on a silica gel column (20×2 cm). Elution with 1:4 hexanes-ethyl acetate afforded 30 as a colorless solid: yield 0.25 g (80%); silica gel TLC R$_f$ 0.3 (1:4 hexanes-ethyl acetate); $^1$H NMR (CDCl$_3$) δ 2.17-2.28 (m, 4H), 2.93-3.09 (m, 4H), 4.61-4.66 (m, 2H), 4.69-4.76 (m, 1H), 4.92-4.99 (m, 2H), 5.65-5.75 (m, 1H), 6.03 (d, 1H, J=7.6 Hz), 6.40 (d, 1H, J=6.8 Hz), 6.99-7.01 (m, 2H) and 7.16-7.29 (m, 8H); $^{13}$C NMR (CDCl$_3$) δ 29.3, 35.5, 37.5, 37.8, 48.8, 53.2, 54.1, 113.7, 115.8, 127.1, 127.5, 128.7, 128.8, 129.1, 129.3, 134.7, 136.3, 136.6, 169.6, 170.8 and 172.4; mass spectrum (APCI), m/z 434.2087 (M+H)$^+$ (C$_{25}$H$_{28}$N$_3$O$_4$ requires m/z 434.2080).

(N-(4-Pentenoyl)phenylalanyl)phenylalanyl-pdCpA (31). A solution containing 10 mg (23 μmol) of cyanomethyl ester 30 and 5.3 mg (3.9 μmol) of the tris(tetrabutylammonium) salt of pdCpA (21) in 100 μL of 9:1 DMF-Et$_3$N was subjected to sonication at room temperature for 2 h. After which time, the reaction mixture was purified by C$_{18}$ reversed phase HPLC (250×10 mm) using a gradient of 1%→65% acetonitrile in 50 mM ammonium acetate, pH 4.5, over a period of 45 min. The fraction eluting at 23.5 min was collected and lyophilized to afford 31 as a colorless solid: yield 3.6 mg (100%); mass spectrum (ESI), m/z 1011.2834 (M−H)$^-$ (C$_{42}$H$_{49}$N$_{10}$O$_{16}$P$_2$ requires m/z 1011.2803).

(N-Boc-phenylalanyl)glycine methyl ester (34). To a solution of 1.00 g (3.80 mmol) of N-Boc-L-phenylalanine (33) in 40 mL of freshly distilled CH$_2$Cl$_2$ at 0° C. was added 1.50 g (4.02 mmol) of HBTU. The reaction mixture was stirred for 30 min. After which time, a solution of 0.52 g (4.15 mmol) of L-phenylalanine methyl ester and 1.2 mL (0.85 g, 8.5 mmol) of Et$_3$N in CH$_2$Cl$_2$ was added. The reaction was further stirred at room temperature for 24 h. The mixture was diluted with 100 mL of CH$_2$Cl$_2$, washed with 100 mL of 1 N HCl, dried (anhydrous MgSO$_4$) and concentrated under diminished pressure.

The residue was purified by flash chromatography on a silica gel column (20×2 cm). Elution with 1:1 ethyl acetate-hexanes afforded 34 as colorless oil: yield 1.05 g (83%); silica gel TLC R$_f$ 0.5 (4% methanol in dichloromethane); $^1$H NMR (CDCl$_3$) δ 1.31 (s, 9H), 2.91-2.96 (m, 1H), 3.07-3.12 (m, 1H), 3.65 (s, 3H), 3.92 (t, 2H, J=6.0 Hz), 4.44 (br s, 1H), 5.37 (d, 1H, J=6.8 Hz), 6.96 (br s, 1H) and 7.13-7.24 (m, 5H); $^{13}$C NMR (CDCl$_3$) δ 28.2, 38.4, 41.1, 52.2, 55.5, 79.9, 126.7, 128.4, 129.3, 136.8, 155.5, 170.0 and 172.0; mass spectrum (APCI+), m/z 337.1761 (M+H)$^+$ (C$_{17}$H$_{25}$N$_2$O$_5$ requires m/z 337.1763).

(N-Boc-(thio)phenylalanyl)glycine methyl ester (35). A mixture containing 0.33 g (0.98 mmol) of 34 and 0.42 g (1.03 mmol) of Lawesson's reagent in 50 mL of toluene was stirred at reflux for 4 h. The reaction mixture was cooled to room temperature and diluted with 100 mL of ethyl acetate. The resulting mixture was washed with 200 mL water, dried (anhydrous $MgSO_4$) and concentrated under diminished pressure. The residue was purified by flash chromatography on a silica gel column (20×3 cm). Elution with 1:2 ethyl acetate-hexanes afforded 35 as a light yellow oil; yield 0.21 g (61%); $R_f$ 0.4 (1:2 ethyl acetate-hexanes); $^1$H NMR ($CDCl_3$) δ 1.37 (s, 9H), 3.11-3.16 (m, 2H), 3.71 (s, 3H), 4.18-4.31 (m, 2H), 4.65 (q, 1H, J=7.2 Hz), 5.32 (br d, 1H, J=6.4 Hz), 7.17-7.27 (m, 5H) and 8.18 (br s, 1H); $^{13}$C NMR ($CDCl_3$) δ 28.2, 41.9, 43.1, 46.7, 52.5, 80.1, 127.0, 128.6, 129.1, 136.6, 155.2, 168.5 and 204.0; mass spectrum (APCI), m/z 353.1540 $(M+H)^+$ ($C_{17}H_{25}N_2O_4S$ requires m/z 353.1535).

(N-(4-pentenoyl)-(thio)phenylalanyl)glycine methyl ester (36). To a solution of 0.18 g (0.51 mmol) of 35 in 5 mL of $CH_2Cl_2$ was added 0.20 mL (0.29 g; 2.60 mmol) of TFA. The reaction mixture was stirred at room temperature for 24 h. The solution was concentrated and dried under diminished pressure for 15 min to afford crude product.

The crude product was dissolved in 5 mL of anhydrous DMF. To this solution was added 0.26 g (3.10 mmol) of $NaHCO_3$ and 0.20 g (1.00 mmol) of 4-pentenoyloxysuccinimide. The reaction mixture was stirred at room temperature for 24 h, diluted with 50 mL of ethyl acetate, washed with 50 mL of water, dried (anhydrous $MgSO_4$) and concentrated under diminished pressure to obtain crude product. The residue was purified by flash chromatography on a silica gel column (15×2 cm). Elution with 1:1 ethyl acetate-hexanes afforded 36 as light yellow semi-solid; yield 0.10 g (60%); $R_f$ 0.3 (1:1 ethyl acetate-hexanes); $^1$H NMR ($CDCl_3$) δ 2.20-2.30 (m, 4H), 3.04-3.15 (m, 2H), 3.69 (s, 3H), 4.13-4.28 (m, 2H), 4.93-5.09 (m, 3H), 5.66-5.76 (m, 1H), 6.54 (d, 1H, J=8 Hz), 7.15-7.24 (m, 5H) and 8.48 (br s, 1H); $^{13}$C NMR ($CDCl_3$) δ 29.3, 35.6, 41.9, 46.7, 52.5, 60.0, 115.7, 127.0, 128.5, 129.2, 136.4, 136.6, 168.3, 172.1 and 203.8; mass spectrum (APCI+), m/z 335.1439 $(M+H)^+$ ($C_{17}H_{23}N_2O_3S$ requires m/z 335.1429).

(N-(4-pentenoyl)-(thio)phenylalanyl)glycine cyaonomethyl ester (37). To a solution of 70.0 mg (0.21 mmol) of 36 in 4 mL of 1:1 THF-water was added 0.40 mL (0.40 mmol) of 1 M aq LiOH. The reaction mixture was stirred at room temperature for 24 h, neutralized with 0.5 N HCl and concentrated under diminished pressure to afford crude product.

The crude product was dissolved in 2 mL of DMF. To this solution was added 55.0 mg (0.65 mmol) of $NaHCO_3$ followed by 50.0 µL (60.0 mg, 0.06 mmol) of chloroacetonitrile. The reaction mixture was stirred at room temperature for 24 h and concentrated under diminished pressure. The residue was purified by flash chromatography on a silica gel column (15×2 cm). Elution with 3:1 ethyl acetate-hexanes afforded 37 as pale yellow oil; yield 49.0 mg (66%); $R_f$ 0.2 (1:1 ethyl acetate-hexanes); $^1$H NMR ($CDCl_3$) δ 2.26 (s, 4H), 3.11 (d, 2H, J=7.6 Hz), 4.23-4.40 (m, 2H), 7.20 (d, 2H, J=4.0 Hz), 4.9-5.14 (m, 3H), 5.66-5.74 (m, 1H), 6.45 (d, 1H, J=8.4 Hz), 7.14-7.26 (m, 5H) and 8.85 (bs, 1H); $^{13}$C NMR ($CDCl_3$) δ 29.2, 35.6, 41.7, 46.2, 49.0, 59.9, 113.6, 115.9, 127.1, 128.6, 129.2, 136.3, 136.5, 166.5, 172.5 and 205.0; mass spectrum (APCI+), m/z 360.1384 $(M+H)^+$ ($C_{18}H_{22}N_2O_3S$ requires m/z 360.1382).

(N-(4-pentenoyl)-(thio)phenylalanyl)glycyl-pdCpA (38). A solution containing 10 mg (27 µmol) of cyanomethyl ester 37 and 5.3 mg (3.9 µmol) of the tris(tetrabutylammonium) salt of pdCpA (21) in 100 µL of 9:1 DMF-$Et_3N$ was subjected to sonication at room temperature for 2 h. The reaction mixture was purified by $C_{18}$ reversed phase HPLC (250×10 mm) using a gradient of 1%→65% acetonitrile in 50 mM ammonium acetate, pH 4.5, over a period of 45 min. The fraction eluting at 21.3 min was collected, and lyophilized to afford 38 as a colorless solid: yield 3.6 mg (100%); mass spectrum (ESI), m/z 937.2133 $(M-H)^+$ ($C_{35}H_{43}N_{10}O_{16}P_2S$ requires m/z 937.2105).

Methyl 2-(diphenylmethyleneamino)acetate (41). To a stirred suspension containing 5.00 g (39.9 mmol) of glycine methyl ester hydrochloride (40) in 20 mL of anhydrous $CH_2Cl_2$ was added 6.70 mL (7.20 g, 39.9 mmol) of benzophenone imine dropwise. The white mixture was stirred at 25° C. for 24 h under argon atmosphere. The reaction mixture was filtered and concentrated under diminished pressure.

The crude product was crystallized from ether-hexanes to afford 41 as white crystals; yield 8.20 g (81%); silica gel TLC $R_f$ 0.22 (1:9 ethyl acetate-hexanes); $^1$H NMR ($CDCl_3$) δ 3.73 (s, 3H), 4.21 (s, 2H), 7.15-7.18 (m, 2H), 7.30-7.45 (m, 6H) and 7.63-7.66 (m, 2H); $^{13}$C NMR ($CDCl_3$) δ 52.0, 55.6, 127.6, 128.05, 128.69, 128.75, 128.83, 130.5, 135.9, 139.2, 171.1 and 171.9; mass spectrum (APCI), m/z 254.1182 $(M+H)^+$ ($C_{16}H_{16}NO_2$ requires m/z 254.1181).

Methyl 2-(2-(((9H-fluoren-9-yl)methoxy)carbonylamino) acetamido)-3-(4-methoxyphenyl)-3-oxopropanoate (44). A solution of 0.50 g (2.00 mmol) of 41 in 5 mL of anhydrous THF was cooled to −78° C. under argon atmosphere and 2.00 mL (2.00 mmol) of 1 M sodium bis(trimethylsilyl) amide in THF was added dropwise while maintaining the temperature at −78° C. After 30 min, the resulting yellow solution was added via cannula to a stirred solution of 0.34 g (2.00 mmol) of 4-methoxybenzoyl chloride in 3 mL anhydrous THF at −78° C. The mixture was stirred at −78° C. for 1 h and then at 0° C. for 1 h. The yellow mixture was acidified with concentrated HCl until pH 2 and was concentrated under diminished pressure. The crude product (42) was utilized for the next reaction without further purification.

To a solution of the crude product in 10 mL of anhydrous THF at 0° C. was added 0.79 g (2.00 mmol) of Fmoc-gly-N-hydroxysuccinimide (43) followed by a dropwise addition of 0.22 mL (0.20 g, 2.00 mmol) N-methylmorpholine. The yellow mixture was stirred at 25° C. for 2 h and concentrated under diminished pressure. The crude product was purified on a silica gel column (15×2 cm). Elution with 1:1 ethyl acetate-hexanes afforded 44 as a colorless oil: yield 0.67 g (67%); silica gel TLC $R_f$ 0.29 (3:2 ethyl acetate-hexanes); $^1$H NMR ($CDCl_3$) δ 3.69 (s, 3H), 3.85 (s, 3H), 4.05 (br s, 2H), 4.22 (s, 1H), 4.40 (d, 2H, J=6.8 Hz), 5.68 (br s, 1H), 6.18 (d, 1H, J=6.8 Hz), 6.94 (d, 2H, J=8.8 Hz), 7.29 (t, 2H, J=7.2 Hz), 7.38 (t, 2H, J=7.4 Hz), 7.53 (d, 1H, J=6.8 Hz), 7.60 (d, 2H, J=7.6 Hz), 7.75 (d, 2H, J=7.6 Hz) and 8.09 (d, 2H, J=8.8 Hz); $^{13}$C NMR ($CDCl_3$) (44.3, 47.2, 53.4, 55.7, 57.7, 67.4, 114.2, 120.0, 125.2, 126.8, 127.2, 127.8, 132.2, 141.4, 143.9, 156.6, 164.9, 167.3, 169.0 and 189.1; mass spectrum (APCI), m/z 503.1816 $(M+H)^+$ ($C_{28}H_{27}N_2O_7$ requires m/z 503.1818).

Methyl 2-((((9H-fluoren-9-yl)methoxy)carbonylamino) methyl)-4-(4-methoxyphenyl)oxazole-5-carboxylate (45). To a stirred solution of 0.17 g (0.80 mmol) of triphenylphosphine and 0.20 g (0.80 mmol) of iodine in 10 mL of anhydrous $CH_2Cl_2$ was added 0.11 mL (83.0 mg, 0.80 mmol) of triethylamine. The dark yellow solution was stirred for 5 min and 0.20 g (0.40 mmol) 44 dissolved in 5 mL anhydrous CH$_2$Cl$_2$ was added dropwise. The mixture was stirred for 30 minutes at 25° C. under argon atmosphere and was concentrated under diminished pressure. The residue was purified on a silica gel column (15×2 cm). Elution with 3:2 ethyl acetate-hexanes afforded 45 as a white solid: yield 0.15 g (78%); silica gel TLC R$_f$ 0.45 (1:1 ethyl acetate-hexanes); $^1$H NMR (CDCl$_3$) δ 3.83 (s, 3H), 3.90 (s, 3H), 4.21 (t, 1H, J=6.8 Hz), 4.43 (d, 2H, J=6.8 Hz), 4.57 (d, 2H, J=5.6 Hz), 5.62 (br s, 1H), 6.94 (d, 2H, J=9.2 Hz), 7.24-7.29 (m, 2H), 7.36 (t, 2H, J=7.4 Hz), 7.57 (d, 2H, J=7.2 Hz), 7.73 (d, 2H, J=7.6 Hz) and 7.80 (d, 2H, J=9.2 Hz); $^{13}$C NMR (CDCl$_3$) δ 38.2, 47.1, 52.2, 55.4, 67.2, 113.9, 119.0, 120.0, 125.0, 125.3, 127.0, 127.7, 130.1, 141.3, 143.7, 156.2, 156.3, 158.4, 161.3 and 162.5; mass spectrum (APCI), m/z 485.1722 (M+H)$^+$ (C$_{28}$H$_{25}$N$_2$O$_6$ requires m/z 485.1713).

Methyl 4-(4-methoxyphenyl)-2-(pent-4-enamidomethyl)oxazole-5-carboxylate (47). To a stirred solution of 0.15 g (0.31 mmol) of 45 in 4 mL of anhydrous CH$_2$Cl$_2$ was added 31.0 μL (27.0 mg, 0.31 mmol) piperidine dropwise. The reaction mixture was stirred at 25° C. under argon atmosphere for 2 h and was concentrated under diminished pressure. The residue was dissolved in 5 mL of anhydrous THF and 0.61 g (3.10 mmol) 4-pentenoyl succinimide followed by 66.0 mg (0.62 mmol) of Na$_2$CO$_3$ were added. The mixture was stirred at room temperature for 3 h under argon atmosphere and was concentrated under diminished pressure.

The residue was purified on a silica gel column (7×2 cm). Elution with 7:3 ethyl acetate-hexanes afforded 47 as a pale yellow solid: yield 60.0 mg (42% over two steps); silica gel TLC R$_f$ 0.19 (7:3 ethyl acetate-hexanes); $^1$H NMR (CDCl$_3$) δ 2.33-2.41 (m, 4H), 3.84 (s, 3H), 3.90 (s, 3H), 4.62 (d, 2H, J=5.6 Hz), 4.96-5.07 (m, 2H), 5.78-5.85 (m, 1H), 6.43 (br s, 1H), 6.95 (d, 2H, J=8.8 Hz) and 7.99 (d, 2H, J=9.2 Hz); $^{13}$C NMR (CDCl$_3$) δ 29.4, 35.6, 36.6, 52.3, 55.5, 114.0, 115.8, 119.1, 125.3, 130.2, 136.9, 156.4, 158.6, 161.4, 162.5 and 172.5; mass spectrum (APCI), m/z 345.1452 (M+H)$^+$ (C$_{18}$H$_{21}$N$_2$O$_5$ requires m/z 345.1450).

Cyanomethyl 4-(4-methoxyphenyl)-2-(pent-4-enamidomethyl)oxazole-5-carboxylate (49). To a stirred solution of 15.0 mg (0.04 mmol) of 47 in 0.40 mL of 3:1 THF-water was added 0.13 mL of 1 N LiOH. The mixture was stirred at 25° C. for 2 h. The yellow aqueous layer was diluted with MeOH. The organic layer was dried over anhydrous Na$_2$SO$_4$ and was concentrated under diminished pressure.

The crude product was dissolved in 2 mL of anhydrous DMF and 27.0 mg (0.32 mmol) NaHCO$_3$ was added followed by 13.0 μL (15.0 mg, 0.21 mmol) of ClCH$_2$CN. The reaction mixture was stirred at 25° C. for 3 h under argon atmosphere. The mixture was concentrated under diminished pressure and was purified on a silica gel column (7×1 cm). Elution with 2.5% methanol in dichloromethane afforded 49 as a pale yellow solid: yield 6.0 mg (37%); silica gel TLC R$_f$ 0.74 (ethyl acetate); $^1$H NMR (CDCl$_3$) δ 2.37-2.44 (m, 4H), 3.87 (s, 3H), 4.64 (d, 2H, J=2.8 Hz), 4.94 (s, 2H), 4.99-5.10 (m, 2H), 5.80-5.84 (m, 1H), 6.25 (br s, 1H), 6.99 (d, 2H, J=8.8 Hz) and 8.10 (d, 2H, J=8.8 Hz); $^{13}$C NMR (CDCl$_3$) δ 29.4, 31.1, 35.6, 36.6, 48.8, 55.6, 114.2, 116.0, 118.4, 123.4, 130.4, 136.8, 158.3, 158.9, 160.6, 162.0 and 172.5; mass spectrum (APCI), m/z 370.1402 (M+H)$^+$ (C$_{19}$H$_{20}$N$_3$O$_5$ requires m/z 370.1403).

4-(4-methoxyphenyl)-2-(pent-4-enamidomethyl)oxazole-5-carboxyl pdCpA (51). A solution containing 6.0 mg (16 μmol) of cyanomethyl ester 49 and 5.3 mg (4.0 mol) of the tris(tetrabutylammonium) salt of pdCpA (14) in 100 μL of 9:1 DMF-Et$_3$N was subjected to sonication at room temperature for 2 h. The reaction mixture was purified by C$_{18}$ reversed phase HPLC (250×10 mm) using a gradient of 1% to 65% acetonitrile in 50 mM ammonium acetate, pH 4.5, over a period of 45 min. The fraction eluting at 19 min was collected and lyophilized to afford 51 as a colorless solid: yield-4.0 mg (60%). mass spectrum (ESI), m/z 947.2159 (M−H)$^-$ (C$_{36}$H$_{41}$N$_{10}$O$_{17}$P$_2$ requires m/z 947.2126).

Methyl 2-((((9H-fluoren-9-yl)methoxy)carbonylamino)methyl)-4-(4-methoxyphenyl)thiazole-5-carboxylate (46). To a stirred solution of 0.22 g (0.44 mmol) of 44 in 5 mL of anhydrous THF was added 0.36 g (0.88 mmol) of the lawessen's reagent. The mixture was heated to reflux under argon atmosphere for 1 h. The yellow reaction mixture was diluted with 20 mL saturated NaHCO$_3$ solution. The aqueous layer was extracted with two 25-mL portions of ethyl acetate. The organic layer was dried over anhydrous MgSO$_4$ and was concentrated under diminished pressure. The crude (46) was utilized in the next reaction without further purification.

Methyl 4-(4-methoxyphenyl)-2-(pent-4-enamidomethyl)thiazole-5-carboxylate (48). To a stirred solution of crude 46 in 4 mL of anhydrous CH$_2$Cl$_2$ was added 43.0 μL (37.0 mg, 0.44 mmol) of piperidine dropwise. The reaction mixture was stirred at 25° C. under argon atmosphere for 3 h and was concentrated under diminished pressure. The residue was dissolved in 5 mL of anhydrous THF and 0.13 g (0.66 mmol) of 4-pentenoyl succinimide followed by 47.0 mg (0.44 mmol) of Na$_2$CO$_3$ was added. The mixture was stirred at room temperature for 3 h under argon atmosphere and was concentrated under diminished pressure.

The residue was purified on a silica gel column (7×2 cm). Elution with 7:3 ethyl acetate-hexanes afforded 48 as a pale yellow solid: yield 73.0 mg (45% over three steps); silica gel TLC R$_f$ 0.19 (7:3 ethyl acetate-hexanes); $^1$H NMR (CDCl$_3$) δ 2.32-2.41 (m, 4H), 3.81 (s, 3H), 3.83 (s, 3H), 4.70 (d, 2H, J=6.4 Hz), 4.97-5.07 (m, 2H), 5.77-5.81 (m, 1H), 6.59 (br s, 1H), 6.91 (d, 2H, J=8.8 Hz) and 7.39 (d, 2H, J=8.4 Hz); $^{13}$C NMR (CDCl$_3$) δ 29.4, 35.5, 41.1, 52.3, 55.4, 113.8, 115.9, 122.1, 131.4, 136.8, 138.6, 148.3, 160.6, 162.5, 165.4 and 172.7; mass spectrum (MALDI-TOF), m/z 361.1110 (M+H)$^+$ (C$_{18}$H$_{21}$N$_2$O$_4$S requires m/z 361.1144).

Cyanomethyl 4-(4-methoxyphenyl)-2-(pent-4-enamidomethyl)thiazole-5-carboxylate (50). To a stirred solution of 15.0 mg (0.04 mmol) of 48 in 0.40 mL of 3:1 THF-water was added 0.13 mL of 1 N LiOH. The mixture was stirred at 25° C. for 2 h. The yellow aqueous layer was diluted with MeOH. The organic layer was dried over anhydrous Na$_2$SO$_4$ and was concentrated under diminished pressure.

The crude product was dissolved in 2 mL of anhydrous DMF and 7.00 mg (0.08 mmol) of NaHCO$_3$ was added followed by 13.0 μL (16.0 mg, 0.21 mmol) of ClCH$_2$CN. The reaction mixture was stirred at 25° C. for 3 h under argon atmosphere. The mixture was concentrated under diminished pressure and was purified on a silica gel column (7×1 cm). Elution with ethyl acetate afforded 50 as a pale yellow solid: yield 6.0 mg (38%); silica gel TLC R$_f$ 0.74 (ethyl acetate); $^1$H NMR (CDCl$_3$) δ 2.37-2.44 (m, 4H), 3.87 (s, 3H), 4.64 (d, 2H, J=2.8 Hz), 4.94 (s, 2H), 4.99-5.10 (m, 2H), 5.80-5.84 (m, 1H), 6.25 (br s, 1H), 6.99 (d, 2H, J=8.8 Hz) and 8.10 (d, 2H, J=8.8 Hz); $^{13}$C NMR (CDCl$_3$) δ 29.4, 31.1, 35.6, 36.6, 48.8, 55.6, 114.2, 116.0, 118.4, 123.4, 130.4, 136.8, 158.3, 158.9, 160.6, 162.0 and 172.5; mass spectrum (MALDI-TOF), m/z 386.1040 (M+H)$^+$ (C$_{19}$H$_{20}$N$_3$O$_4$S requires m/z 386.1096).

4-(4-methoxyphenyl)-2-(pent-4-enamidomethyl)thiazole-5-carboxyl pdCpA (52). A solution containing 6.0 mg (16 μmol) of cyanomethyl ester 50 and 8.0 mg (6.0 μmol) of the tris(tetrabutylammonium) salt of pdCpA (38) in 100 μL of 9:1 DMF-Et$_3$N was subjected to sonication at room temperature for 4 h. The reaction mixture was purified by C$_{18}$ reversed phase HPLC (250×10 mm) using a gradient of 1% to 65% acetonitrile in 50 mM ammonium acetate, pH 4.5, over a period of 45 min. The fraction eluting at 19 min was collected and lyophilized to afford 52 as a colorless solid: yield-6.0 mg (60%). mass spectrum (MALDI-TOF), m/z 965.1964 (M+H)$^+$ (C$_{36}$H$_{43}$N$_{10}$O$_{16}$P$_2$S requires m/z 965.2010).

Methyl 2-(2-(((9H-fluoren-9-yl)methoxy)carbonylamino)acetamido)-3-(4-(dimethylamino)phenyl)-3-oxopropanoate (56). A solution of 0.50 g (2.00 mmol) of 35 in 5 mL of anhydrous THF was cooled to −78° C. under argon atmosphere and 2.00 mL (2.00 mmol) of 1 M sodium bis(trimethylsilyl)amide in THE was added dropwise while maintaining the temperature at −78° C. After 30 min, the resulting yellow solution was added via cannula to a stirred solution of 0.43 g (2.00 mmol) of 4-dimethylaminobenzoyl chloride in 3 mL of anhydrous THE at −78° C. The mixture was stirred at −78° C. for 2 h. The yellow mixture was acidified with concentrated HCl until pH 2 and was concentrated under diminished pressure.

The crude product (55) was utilized for the next reaction without further purification. To a solution of the crude product in 10 mL of anhydrous THF at 0° C. was added 0.79 g (2.00 mmol) of N-Fmoc-glycine succinimide ester (43) followed by a dropwise addition of 0.22 mL (0.20 g, 2.00 mmol) N-methylmorpholine. The yellow mixture was stirred at 25° C. for 2 h and concentrated under diminished pressure. The crude product was purified on a silica gel column (15×2 cm). Elution with 1:1 ethyl acetate-hexanes afforded 56 as a yellowish solid: yield 0.35 g (34%); silica gel TLC R$_f$ 0.27 (1:1 ethyl acetate-hexanes); $^1$H NMR (CDCl$_3$) δ 3.03 (s, 6H), 3.68 (s, 3H), 4.07 (br s, 2H), 4.21 (s, 1H), 4.38 (d, 2H, J=7.6 Hz), 5.65 (br s, 1H), 6.10 (d, 1H, J=7.6 Hz), 6.63 (d, 2H, J=8.8 Hz), 7.28 (t, 2H, J=7.4 Hz), 7.37 (t, 2H, J=7.4 Hz), 7.48 (d, 1H, J=7.2 Hz), 7.59 (d, 2H, J=7.6 Hz), 7.73 (d, 2H, J=7.6 Hz) and 8.00 (d, 2H, J=8.8 Hz); $^{13}$C NMR (CDCl$_3$) δ 44.3, 47.2, 53.4, 55.7, 57.7, 67.4, 114.2, 120.0, 125.2, 126.8, 127.2, 127.8, 132.2, 141.4, 143.9, 156.6, 164.9, 167.3, 169.0 and 189.1; mass spectrum (MALDI-TOF), m/z 516.2060 (M+H)$^+$ (C$_{29}$H$_{30}$N$_3$O$_6$ requires m/z 516.2069).

Methyl 2-((((9H-fluoren-9-yl)methoxy)carbonylamino)methyl)-4-(4-(dimethylamino)phenyl)oxazole-5-carboxylate (57). To a stirred solution of 0.29 g (1.12 mmol) of triphenylphosphine and 0.28 g (1.12 mmol) of iodine in 10 mL of anhydrous CH$_2$Cl$_2$ was added 0.15 mL (0.11 g, 1.12 mmol) of triethylamine. The dark yellow solution was stirred for 5 min and 0.29 g (0.56 mmol) of 56 dissolved in 5 mL of anhydrous CH$_2$Cl$_2$ was added dropwise. The mixture was stirred for 30 minutes at 25° C. under argon atmosphere and was concentrated under diminished pressure.

The residue was purified on a silica gel column (15×2 cm). Elution with 2:3 ethyl acetate-hexanes afforded 57 as a yellow solid: yield 0.20 g (71%); silica gel TLC R$_f$ 0.43 (1:1 ethyl acetate-hexanes); $^1$H NMR (CDCl$_3$) δ 3.03 (s, 6H), 3.92 (s, 3H), 4.24 (t, 1H, J=6.8 Hz), 4.44 (d, 2H, J=7.2 Hz), 4.59 (d, 2H, J=5.6 Hz), 5.59 (br s, 1H), 6.71 (d, 2H, J=8.8 Hz), 7.29 (m, 2H), 7.38 (t, 2H, J=7.4 Hz), 7.60 (d, 2H, J=6.8 Hz), 7.75 (d, 2H, J=7.6 Hz) and 7.99 (d, 2H, J=9.2 Hz); $^{13}$C NMR (CDCl$_3$) δ 38.3, 40.1, 47.1, 52.1, 67.3, 111.3, 113.8, 120.0, 123.8, 125.1, 127.1, 127.7, 130.0, 141.3, 143.8, 151.6, 156.2, 157.46, 157.53 and 162.7; mass spectrum (MALDI-TOF), m/z 498.1930 (M+H)$^+$ (C$_{29}$H$_{28}$N$_3$O$_5$ requires m/z 498.1951).

Methyl 4-(4-(dimethylamino)phenyl)-2-(pent-4-enamidomethyl)oxazole-5-carboxylate (59). To a stirred solution of 0.20 g (0.40 mmol) of 57 in 4 mL of anhydrous CH$_2$Cl$_2$ was added 77.0 μL (66.0 mg, 0.78 mmol) of piperidine dropwise. The reaction mixture was stirred at 25° C. under argon atmosphere for 2 h and was concentrated under diminished pressure. The residue was dissolved in 5 mL of anhydrous THF and 0.15 g (0.78 mmol) of 4-pentenoyl succinimide followed by 83.0 mg (0.78 mmol) of Na$_2$CO$_3$ was added. The mixture was stirred at room temperature for 3 h under argon atmosphere and was concentrated under diminished pressure.

The residue was purified on a silica gel column (7×2 cm). Elution with 7:3 ethyl acetate-hexanes afforded 59 as a pale yellow solid: yield 48.0 mg (33% over two steps); silica gel TLC R$_f$ 0.19 (7:3 ethyl acetate-hexanes); $^1$H NMR (CDCl$_3$) δ 2.39-2.44 (m, 4H), 3.04 (s, 6H), 3.92 (s, 3H), 4.63 (d, 2H, J=5.6 Hz), 4.99-5.10 (m, 2H), 5.80-5.87 (m, 1H), 6.24 (br s, 1H), 6.73 (d, 2H, J=9.2 Hz) and 7.99 (d, 2H, J=9.2 Hz); $^{13}$C NMR (CDCl$_3$) δ 29.3, 35.5, 36.6, 40.0, 52.1, 111.3, 113.7, 115.7, 123.7, 129.6, 136.8, 151.6, 157.45, 157.50, 162.7 and 172.2; mass spectrum (MALDI-TOF), m/z 358.1680 (M+H)$^+$ (C$_{19}$H$_{24}$N$_3$O$_4$ requires m/z 358.1689).

Cyanomethyl 4-(4-(dimethylamino)phenyl)-2-(pent-4-enamidomethyl)oxazole-5-carboxylate (61). To a stirred solution of 15.0 mg (0.04 mmol) of 59 in 0.40 mL 3:1 THF-water was added 0.08 mL of 1 N LiOH. The mixture was stirred at 25° C. for 3 h. The yellow aqueous layer was diluted with MeOH. The organic layer was dried over anhydrous Na$_2$SO$_4$ and was concentrated under diminished pressure.

The crude product was dissolved in 2 mL of anhydrous DMF and 10.0 mg (0.09 mmol) of NaHCO$_3$ was added followed by 13.0 μL (16.0 mg, 0.21 mmol) of ClCH$_2$CN. The reaction mixture was stirred at 25° C. for 3 h under argon atmosphere. The mixture was concentrated under diminished pressure and was purified on a silica gel column (7×1 cm). Elution with ethyl acetate afforded 61 as a pale yellow solid: yield 6.0 mg (38%); silica gel TLC R$_f$ 0.74 (ethyl acetate); $^1$H NMR (CDCl$_3$) δ 2.36-2.45 (m, 4H), 3.06 (s, 6H), 4.64 (d, 2H, J=5.2 Hz), 4.94 (s, 2H), 5.01-5.11 (m, 2H), 5.81-5.85 (m, 1H), 6.12 (br s, 1H), 6.73 (d, 2H, J=8.8 Hz) and 7.99 (d, 2H, J=8.8 Hz); mass spectrum (MALDI-TOF), m/z 383.1640 (M+H)$^+$ (C$_{20}$H$_{23}$N$_4$O$_4$ requires m/z 383.1641).

4-(4-(dimethylamino)phenyl)-2-(pent-4-enamidomethyl)oxazole-5-carboxyl pdCpA (63). A solution containing 6.0 mg (16 μmol) of cyanomethyl ester 61 and 8.0 mg (6.0 μmol) of the tris(tetrabutylammonium) salt of pdCpA (38) in 100 μL of 9:1 DMF-Et$_3$N was subjected to sonication at room temperature for 2.5 h. The reaction mixture was purified by C$_{18}$ reversed phase HPLC (250×10 mm) using a gradient of 1% to 65% acetonitrile in 50 mM ammonium acetate, pH 4.5, over a period of 45 min. The fraction eluting at 19.5 min was collected and lyophilized to afford 63 as a yellow solid: yield-3.7 mg (59%); mass spectrum (ESI), m/z 960.2440 (M−H)$^-$ (C$_{37}$H$_{44}$N$_{11}$O$_{16}$P$_2$ requires m/z 960.2443).

Methyl 2-((((9H-fluoren-9-yl)methoxy)carbonylamino)methyl)-4-(4-(dimethylamino)phenyl)thiazole-5-carboxylate (58). To a stirred solution of 0.16 g (0.31 mmol) of 56 in 5 mL of anhydrous THF was added 0.25 g (0.62 mmol) of the lawessen's reagent. The mixture was heated to reflux under argon atmosphere for 1 h. The yellow reaction mixture was diluted with 20 mL saturated NaHCO₃ solution. The aqueous layer was extracted with two 25 mL portions of ethyl acetate. The organic layer was dried over anhydrous MgSO₄ and was concentrated under diminished pressure. The crude was utilized in the next reaction without further purification.

Methyl 4-(4-(dimethylamino)phenyl)-2-(pent-4-enamidomethyl)thiazole-5-carboxylate (60). To a stirred solution of the crude 58 in 4 mL of anhydrous $CH_2Cl_2$ was added 64.0 μL (55.0 mg, 0.65 mmol) of piperidine dropwise. The reaction mixture was stirred at 25° C. under argon atmosphere for 2 h and was concentrated under diminished pressure. The residue was dissolved in 5 mL of anhydrous THF and 0.26 g (1.32 mmol) of 4-pentenoyl succinimide followed by 83.0 mg (0.78 mmol) of $Na_2CO_3$ was added. The mixture was stirred at room temperature for 3 h under argon atmosphere and was concentrated under diminished pressure.

The residue was purified on a silica gel column (7×2 cm). Elution with 7:3 ethyl acetate-hexanes afforded 60 as a pale yellow solid: yield 60.0 mg (52% over three steps); silica gel TLC $R_f$ 0.17 (7:3 ethyl acetate-hexanes); $^1$H NMR (CDCl₃) δ 2.35-2.44 (m, 4H), 3.01 (s, 6H), 3.86 (s, 3H), 4.72 (d, 2H, J=5.2 Hz), 5.00-5.10 (m, 2H), 6.25 (br s, 1H), 6.25 (br s, 1H), 6.70 (d, 2H, J=8.4 Hz) and 7.40 (d, 2H, J=8.4 Hz); mass spectrum (MALDI-TOF), m/z 374.1455 (M+H)⁺ ($C_{19}H_{24}N_3O_3S$ requires m/z 374.1460).

Cyanomethyl 4-(4-(dimethylamino)phenyl)-2-(pent-4-enamidomethyl)thiazole-5-carboxylate (62). To a stirred solution of 17.0 mg (0.05 mmol) of 60 in 0.4 mL of 3:1 THF-water was added 0.06 mL of 1 N LiOH. The mixture was stirred at 25° C. for 4.5 h. The yellow aqueous layer was diluted with MeOH. The organic layer was dried over anhydrous $Na_2SO_4$ and was concentrated under diminished pressure.

The crude product was dissolved in 2 mL of anhydrous DMF and 9.0 mg (0.11 mmol) of NaHCO₃ was added followed by 25.0 μL (30.0 mg, 0.40 mmol) of ClCH₂CN. The reaction mixture was stirred at 25° C. for 3 h under argon atmosphere. The mixture was concentrated under diminished pressure and was purified on a silica gel column (7×1 cm). Elution with 3:2 ethyl acetate-hexanes afforded 62 as a bright yellow solid: yield 12.0 mg (65%); silica gel TLC $R_f$ 0.7 (ethyl acetate); $^1$H NMR (CDCl₃) δ 2.36-2.44 (m, 4H), 3.02 (s, 6H), 4.71 (d, 2H, J=2.8 Hz), 4.87 (s, 2H), 5.00-5.10 (m, 2H), 5.79-5.84 (m, 1H), 6.29 (br s, 1H), 6.71 (d, 2H, J=8.4 Hz) and 7.39 (d, 2H, J=8.4 Hz); mass spectrum (MALDI-TOF), m/z 399.1210 (M+H)⁺ ($C_{20}H_{23}N_4O_3S$ requires m/z 399.1413).

4-(4-(dimethylamino)phenyl)-2-(pent-4-enamidomethyl) thiazole-5-carboxyl pdCpA (64). A solution containing 6.0 mg (15 μmol) of cyanomethyl ester 62 and 5.7 mg (3.7 μmol) of the tris(tetrabutylammonium) salt of pdCpA in 100 μL of 9:1 DMF-Et₃N was subjected to sonication at room temperature for 4 h. The reaction mixture was purified by C₁₈ reversed phase HPLC (250×10 mm) using a gradient of 1% to 65% acetonitrile in 50 mM ammonium acetate, pH 4.5, over a period of 45 min. The fraction eluting at 19.5 min was collected and lyophilized to afford 64 as a yellow solid: yield-3.7 mg (59%); mass spectrum (ESI), m/z 976.2213 (M–H)⁻ ($C_{37}H_{44}N_{11}O_{15}P_2S$ requires m/z 976.2214).

Methyl 2-(2(2-(benzyloxycarbonyl)acetamido)acetamido)-3-(4-cyanophenyl)-3-oxopropanoate (69). A solution of 1.00 g (4.00 mmol) of 35 in 10 mL of anhydrous THF was cooled to –78° C. under argon atmosphere and 4.00 mL (4.00 mmol) of 1 M sodium bis(trimethylsilyl)amide in THF was added dropwise while maintaining the temperature at –78° C. After 30 min, the resulting yellow solution was added via cannula to a stirred solution of 0.66 g (4.00 mmol) of 4-cyanobenzoyl chloride in 3 mL of anhydrous THF at –78° C. The mixture was stirred at –78° C. for 2 h. The yellow mixture was acidified with concentrated HCl until pH 2 and was concentrated under diminished pressure. The crude product (67) was utilized for the next reaction without further purification.

To a solution of the crude product in 10 mL of anhydrous THF at 0° C. was added 1.56 g (4.00 mmol) of N-Cbz-glycine succinimide ester (68) followed by a dropwise addition of 0.44 mL (0.40 g, 4.00 mmol) N-methylmorpholine. The yellow mixture was stirred at 25° C. for 2 h and concentrated under diminished pressure. The crude product was purified on a silica gel column (15×2 cm). Elution with 1:1 ethyl acetate-hexanes afforded 69 as a colorless oil: yield 0.60 g (38%); silica gel TLC Re 0.3 (1:1 ethyl acetate-hexanes); $^1$H NMR (CDCl₃) (3.69 (s, 3H), 3.97 (d, 2H, J=5.2 Hz), 5.10 (s, 2H), 5.57 (d, 11H, J=4.8 Hz), 6.16 (d, 1H, J=6.8 Hz), 7.32 (br s, 5H), 7.51-7.53 (m, 1H), 7.76 (d, 2H, J=8.4 Hz), 8.15 (d, 2H, J=8.8 Hz); mass spectrum (MALDI-TOF), m/z 392.1050 (M+H)⁺ ($C_{21}H_{20}N_3O_6$ requires m/z 392.1168).

Methyl 2-((benzyloxycarbonyl)methyl)-5-(4-cyanophenyl)oxazole-4-carboxylate (70). To a stirred solution of 0.21 g (0.80 mmol) of triphenylphosphine and 0.2 g (0.8 mmol) of iodine in 10 mL of anhydrous $CH_2Cl_2$ was added 0.11 mL (83.0 mg, 0.80 mmol) of triethylamine. The dark yellow solution was stirred for 5 min and 0.20 g (0.40 mmol) of 69 dissolved in 5 mL of anhydrous $CH_2Cl_2$ was added dropwise. The mixture was stirred for 30 minutes at 25° C. under argon atmosphere and was concentrated under diminished pressure.

The residue was purified on a silica gel column (15×2 cm). Elution with 1:1 ethyl acetate-hexanes afforded 70 as a pale yellow solid: yield 0.14 g (73%); silica gel TLC $R_f$ 0.5 (1:1 ethyl acetate-hexanes); $^1$H NMR (CDCl₃) δ 3.92 (s, 3H), 4.59 (d, 2H, J=6.0 Hz), 5.13 (s, 2H), 5.56 (br s, 1H), 7.32 (br s, 5H), 7.71 (d, 2H, J=8.4 Hz), 8.17 (d, 2H, J=8.4 Hz); mass spectrum (MALDI-TOF), m/z 392.1050 (M+H)⁺ ($C_{21}H_{18}N_3O_5$ requires m/z 392.1168).

Methyl 4-(4-cyanophenyl)-2-(pent-4-enamidomethyl) oxazole-5-carboxylate (71). To a solution of 0.15 g (0.38 mmol) of 60 in 5 mL of ethanol was added 4 mg of 10%? Pd—C. The reaction mixture was stirred under H₂ atmosphere for 3 h and was filtered through a pad of celite. The filtrate was concentrated under diminished pressure.

The residue was dissolved in 5 mL of anhydrous THF and 0.17 g (0.86 mmol) of 4-pentenoyl succinimide followed by 40.0 mg (0.38 mmol) of $Na_2CO_3$ were added. The mixture was stirred at room temperature for 3 h under argon atmosphere and was concentrated under diminished pressure. The residue was purified on a silica gel column (7×2 cm). Elution with 7:3 ethyl acetate-hexanes yielded 71 as a pale yellow solid: yield 47.0 mg (37% over two steps); silica gel TLC $R_f$ 0.29 (7:3 ethyl acetate-hexanes); $^1$H NMR (CDCl₃) δ 2.34-2.40 (m, 4H), 3.92 (s, 3H), 4.64 (d, 2H, J=6.0 Hz), 4.96-5.12 (m, 2H), 5.77-5.81 (m, 1H), 6.45 (br s, 1H), 7.72 (d, 2H, J=8.8 Hz), 8.18 (d, 2H, J=8.8 Hz); mass spectrum (MALDI-TOF), m/z 340.1210 (M+H)⁺ ($C_{18}H_{18}N_3O_4$ requires m/z 340.1219).

Cyanomethyl 4-(4-cyanophenyl)-2-(pent-4-enamidomethyl)oxazole-5-carboxylate (72). To a stirred solution of 16.0 mg (0.05 mmol) of 71 in 0.4 mL of 3:1 THF-water was added 0.05 mL of 1 N LiOH, The mixture was stirred at 25° C. for 2 h. The aqueous layer was diluted with MeOH. The organic layer was dried over anhydrous $Na_2SO_4$ and was concentrated under diminished pressure.

The crude product was dissolved in 2 mL of anhydrous DMF and 12.0 mg (0.14 mmol) of $NaHCO_3$ was added followed by 15.0 µL (18.0 mg, 0.24 mmol) of $ClCH_2CN$. The reaction mixture was stirred at 25° C. for 3 h under argon atmosphere. The mixture was concentrated under diminished pressure and was purified on a silica gel column (7×1 cm). Elution with ethyl acetate afforded 72 as a pale yellow solid: yield 13.0 mg (76%); silica gel TLC $R_f$ 0.65 (ethyl acetate); $^1$H NMR ($CDCl_3$) δ 2.37-2.44 (m, 4H), 4.67 (d, 2H, J=5.2 Hz), 4.96-5.15 (m, 4H), 5.78-5.86 (m, 1H), 6.30 (br s, 1H), 7.77 (d, 2H, J=8.4 Hz), 8.19 (d, 2H, J=8.4 Hz); mass spectrum (MALDI-TOF), m/z 365.1140 (M+H)$^+$ ($C_{19}H_{17}N_4O_4$ requires m/z 365.1172).

4-(4-cyanophenyl)-2-(pent-4-enamidomethyl)oxazole-5-carboxyl pdCpA (73). A solution containing 7.0 mg (20 µmol) of cyanomethyl ester 72 and 6.0 mg (4.0 µmol) of the tris(tetrabutylammonium) salt of pdCpA (38) in 100 µL of 9:1 DMF-$Et_3$N was subjected to sonication at room temperature for 4 h. The reaction mixture was purified by $C_{18}$ reversed phase HPLC (250×10 mm) using a gradient of 1% to 65% acetonitrile in 50 mM ammonium acetate, pH 4.5, over a period of 45 min. The fraction eluting at 17 min was collected and lyophilized to afford 73 as a white solid: yield 1.9 mg (29%); mass spectrum (ESI), m/z 942.1973 (M–H)$^-$ ($C_{36}H_{38}N_{11}O_{16}P_2$ requires m/z 942.1968).

Preparation of Aminoacyl-tRNA$_{CUA}$s. The activation of suppressor tRNA$_{CUA}$s was carried out as described previously.[4,5] Briefly, 100-µL reaction mixture of 100 mM Na Hepes, pH 7.5, contained 1.0 mM ATP, 15 mM $MgCl_2$, 100 µg of suppressor tRNA$_{CUA}$-$C_{OH}$, 0.5 $A_{260}$ unit of N-pentenoyl-protected aminoacyl-pdCpA, 15% DMSO, and 100 units of T4 RNA ligase. The reaction mixture was incubated at 37° C. for 1.5 h and quenched by the addition of 0.1 vol of 3 M NaOAc, pH 5.2. The N-protected aminoacylated tRNA was precipitated with 3 vol of cold ethanol. The efficiency of ligation was estimated by 8% polyarylamide-7 M urea gel electrophoresis (pH 5.0).

The N-pentenoyl-protected aminoacyl-tRNA$_{CUA}$s were deprotected by treatment with 5 mM aqueous 12 at 25° C. for 15 min. The solution was centrifuged, and the supernatant was adjusted to 0.3 M NaOAc and treated with 3 vol of cold ethanol to precipitate the aminoacylated tRNA. The tRNA pellet was collected by centrifugation, washed with 70% aq EtOH, air dried and dissolved in 20 µL of RNase free water.

Preparation of S-30 Extracts from Cells Having Modified Ribosomes. Aliquots (5-10 µL) from liquid stocks of *E. coli* BL-21 (DE-3) cells, harboring plasmids with a wild-type or modified rrnB gene, were placed on LB agar supplemented with 100 g/mL of ampicillin and grown at 37° C. for 16-18 h. One colony was picked from each agar plate and transferred into 3 mL of LB medium supplemented with 100 µg/mL of ampicillin and 0.5 mM IPTG.

The cultures were grown at 37° C. for 3-6 h in a thermostated shaker until $OD_{600}$~0.15-0.3 was reached, diluted with LB medium supplemented with 100 µg/mL ampicillin, 1 mM IPTG and 3 µg/mL of erythromycin (for selectively enhancing the modified ribosome fraction) until $OD_{600}$ 0.01 was reached, and then grown at 37° C. for 12-18 h. The optimal concentration of the final cultures was $OD_{600}$ 0.5-1.0. Cells were harvested by centrifugation (5000×g, 4° C., 10 min), washed three times with S-30 buffer (1 mM Tris-OAc, pH 8.2, containing 1.4 mM Mg(OAc)$_2$, 6 mM KOAc and 0.1 mM DTT) supplemented with β-mercaptoethanol (0.5 mL/L) and once with S-30 buffer having 0.05 mL/L β-mercaptoethanol.

The weight of the wet pellet was estimated and 1.27 mL of S-30 buffer was added to suspend each 1 g of cells. The volume of the suspension was measured and used for estimating the amount of other components. Pre-incubation mixture (0.3 mL) (0.29 M Tris, pH 8.2, containing 9 mM Mg(OAc)$_2$, 13 mM ATP, 84 mM phosphoenol pyruvate, 4.4 mM DTT and 5 µM amino acids mixture), 15 units of pyruvate kinase and 10 µg of lyzozyme were added per 1 mL of cell suspension and the resulting mixture was incubated at 37° C. for 30 min. The incubation mixture was then frozen at −80° C. (~30 min), melted (37° C., 30 min), and again frozen and melted at room temperature (~30 min). Ethylene glycol tetraacetic acid (EGTA) was then added to 2.5 mM final concentration and the cells were incubated at 37° C. for 30 min. Same molar concentration of $CaCl_2$ was added, mixed well and frozen (−80° C., 30 min). The frozen mixture was centrifuged (15,000×g, 4° C., 1 h) and the supernatant was stored in aliquots at −80° C.

In vitro Protein Translation. Protein translation reactions were carried out in 12-2000 µL of incubation mixture containing 0.4 µL/µL of S-30 system, 100 ng/µL of plasmid, 35 mM Tris acetate, pH 7.4, 190 mM potassium glutamate, 30 mM ammonium acetate, 2 mM DTT, 0.2 mg/mL total *E. coli* tRNA, 3.5% PEG 6000, 20 µg/mL folinic acid, 20 mM ATP and GTP, 5 mM CTP and UTP, 100 µM amino acids mixture, 0.5 µCi/µL of $^{35}$S-methionine for analytical purposes only and 1 µg/mL rifampicin. In the case of plasmids having a gene with a TAG codon, a suppressor tRNA was added to a concentration of 0.8 µg/µL. Reactions were carried out at 37° C. for 1 h (for 12 µL reaction mixtures) to 1.5 h (for 2000 µL reaction mixtures) and terminated by chilling on ice. Aliquots from in vitro translation mixtures were analyzed by SDS-PAGE followed by quantification of the radioactive bands by phosphorimager analysis.

'In-Gel' Trypsin Digestion.[8] Samples to be digested in the gel were run in 3-4 lanes of a 12% SDS-polyacrylamide gel, stained with Coomassie R-250 and destained until the background was clear. That area of the gel having the DHFR was cut from the gel and washed with 0.1 M ammonium bicarbonate (1 h, room temperature). The solution was discarded and 0.1-0.2 mL of 0.1 M ammonium bicarbonate and 10-30 µL of 0.045 mM DTT were added. Gel pieces were incubated at 60° C. for 30 min, cooled to room temperature and incubated at room temperature for 30 min in the dark after the addition of 10-30 µL of 0.1 M iodoacetamide. Gel pieces were washed with 1:1 acetonitrile-0.1 M ammonium bicarbonate until they became colorless.

After discarding the solution, the gel pieces were incubated in 0.1-0.2 mL of acetonitrile (10-20 min at room temperature) and, after removal of solvent, were re-swelled in 50-100 µL of 25 mM ammonium bicarbonate containing 0.02 µg/µL trypsin. After incubation at 37° C. for 4 h, the supernatant was removed to a new tube and the peptides were extracted with 60% acetonitrile in 0.1% TFA (20 min at room temperature). The combined fractions were dried and reconstituted in minimum amount of 60% acetonitrile in 0.1% TFA.

Selection of Modified Ribosomes using Dipeptidyl-puromycin Aminonucleoside The selection experiments were carried on in a fashion similar to that described previously. (1) Briefly, library from 419 clones, having mutations in two regions of the PTC in the 23S rRNA (2057-2063, 2496-2501 or 2502-2507) and organized in five 96 well plates ("master plates"), were used for selection of variants with modified ribosome. Three new plates were prepared for each "master plate" by transferring 2 μL of culture from each well of the master plate to the corresponding well of new plate and 98 μL assay solution was added to each well. Assay solutions have been prepared from LB medium (pH 8.4), containing 100 μg/mL ampicillin, 1 mM IPTG and 100 μg/mL 1 or 3.5 μg/mL erythromycin.

A solution without any puromycin derivative was used for control plate. All plates were incubated at 37° C. for 16-18 h in a thermostated shaker, and extent of cell growth was estimated by measuring the optical density at 600 nm. Inhibition of cell growth by 1 was estimated as described in previously. Clones with inhibition value more than 50% were taken for verification. Cultures were diluted with LB medium, supplemented with 100 μg/mL ampicillin and 1 mM IPTG, until optical density at 600 nm was about 0.01 and placed in 8 wells of a 96-well plate, having six different dilutions of 1 (200-6.25 μg/mL). Plates were incubated at 37° C. for 16-18 h in a thermostated shaker, extent of cell growth was estimated by measuring the optical density at 600 nm and $IC_{50}$ data was calculated for each culture.

Plasmids from cultures showing more than two times decreasing enhancement in $IC_{50}$ value for modified ribosomes relative to wild-type ribosomes were isolated, analyzed by restriction analysis (EcoRI) to check presence of full size rrnB operon and sequenced in two mutated regions.

Synthesis of Dipeptidyl-puromycin Aminonucleoside (1). The dipeptidyl puromycin derivative 1 was synthesized from Fmoc-protected (4-OMe)-tyrosine (14) in four consecutive steps. Compound 14 was activated with HBTU and condensed with glycine methyl ester in presence of $Et_3N$ to obtain 15 in 95% yield. A mild ester hydrolysis by LiOH in THF-water afforded free acid 16 (60% yield), which was subsequently activated as succinimide ester. The crude activated ester was coupled to puromycin aminonucleoside in presence of $Et_3N$ to obtain Fmoc-protected puromycin derivative 17 in a high yield of 94%. Using piperidine, Fmoc group was deprotected and dipeptidyl-puromycin aminonucleoside 1 was obtained in 49% yield.

Selection of Modified Ribosomes. The selection of modified ribosomes, able to incorporate α-L-amino acids, dipeptides and dipeptidomimetics, was carried out in a fashion similar to described previously by our group.[1] Bacterial *E. coli* cells were used for the selection strategy and later on, for the preparation of S-30 extracts having modified ribosomes for in vitro protein translation. Initially, nucleotides 2057-2063 near the peptidyltransferase center in the 23S rRNA were altered to confer erythromycin resistance.

Since cells would harbor both modified (plasmid encoded) and wild-type (chromosomally encoded) 23S rRNAs, a pressure system would be required for enhanced production of modified ribosomes over wild-type ribosomes. Therefore, a library of *E. coli* colonies having randomly mutagenized 23S rRNA gene in nucleotides 2057-2063 was prepared and selected against erythromycin at concentration 3.5 μg/mL and pH 8.25. Eight 23S rRNA variants having different nucleotide sequences in the erythromycin-binding pocket were obtained. The next round of library preparation involved mutagenesis in a second region in the PTC of each of the eight 23S rRNAs. Finally, a new library of clones was obtained having mutations in two regions in the 23S rRNA: first region, 2057-2063 and second region, either one of three regions (2582-2588, 2496-2501 and 2502-2507).

Once a diverse library was in hand, a dual selection against erythromycin and dipeptidyl-aminopuromycin nucleoside (1) was carried out. Erythromycin assay (3.5 μg/mL) confirmed the erythromycin resistance of clones, while puromycin derivative 1 (100 μg/mL) identified clones having increased sensitivity to this antibiotic. It was anticipated that the ribosomes of those clones which show sensitivity for 1 would be more likely to accommodate dipeptides or dipeptidomimetics in the PTC during peptide synthesis. Sixteen clones showing erythromycin resistance and more than 50% inhibition in puromycin assay were selected for further evaluation. Plasmids from these clones were isolated and sequenced.

All selected clones had mutations in two regions as anticipated. Some of clones had wild-type nucleotide sequence in second region of the 23S rRNA and were not evaluated further. It was demonstrated previously that modifications in the region 2582-2588 of the 23S rRNA were responsible for low fidelity of translation and therefore, clones having mutations in region 2582-2588 of the 23S rRNA were not selected for S-30 preparations.[1] Four clones (010309, 010310, 010326 and 010328) were identified as mixtures of more than one clone as judged by the automatic DNA sequencing and were transformed again into *E. coli* cells to separate the clones. Table 1 summarizes the characterization of thirteen clones which were advanced for preparation of S-30 extracts for evaluation in in vitro protein translation using suppressor $tRNA_{CUA}$s activated with dipeptides or dipeptidomimetics.

Table 2 summarizes the homology in sequence in second region of clones. Three of clones (010309R9, 010326R6 and 010328R4) had same nucleotide sequence in two regions of the PTC (2057UGCGUGG2063 and 2502ACGAAG2507), while other two clones (010326R1 and 010328R2) also shared same nucleotide sequence in two mutated regions (2057UGCGUGG2063 and 2502CUACAG2507).

Preparation of Suppressor $tRNA_{CUA}$s Activated with Dipeptides and Dipeptidomimetics. Suppressor $tRNA_{CUA}$s activated with dipeptides and dipeptidomimetics were prepared as described previously[1,2] and pdCpA derivatives of compounds 2-10 were synthesized. Amino acids 11 and 17 were first N-protected using 4-pentenoylsuccimide followed by subsequent condensation with either L-phenylalanine methyl ester or L-glycine methyl ester in the presence of HBTU and $Et_3N$ to afford the N-protected dipeptide methyl esters 19 (47%), 25 (50%) and 29 (61%), respectively. The methyl esters were subjected to saponification in the presence of 1 M aq LiOH to produce the free acids, which were then converted to the corresponding cyanomethyl esters 20, 26 and 30 in 75%, 62% and 80% yields, respectively.

For the synthesis of pdCpA derivative of dipeptidomimetic 5, we started from L-boc-phenylalanine (33). Compound 33 was condensed with glycine methyl ester in presence of HBTU and $Et_3N$ to obtain dipeptide 34 in 83% yield. Dipeptide 34 was readily converted to thio-dipeptide 35 (61% yield) by treatment with Lawesson's reagent in toluene at reflux. The N-protection was removed using trifluoroacetic acid (TFA) and amine was subsequently protected using 4-pentenoylsuccimide to obtain product 36 in 60% yield. Mild hydrolysis of methyl ester by 1 M aq LiOH followed by treatment with chloroacetonitrile and $NaHCO_3$ in DMF afforded cyanomethyl ester 37 in 66% yield.

The synthetic strategy for pdCpA derivatives of 6-10 starts with double protection of glycine. Commercially available glycine methyl ester hydrochloride (40) was treated with benzophenone imine to obtain 41 in 68% yield. Compound 41 was then condensed with three different acyl chlorides in the presence of NaHMDS as a base. The subsequent hydrolysis of the imine with conc. HCl afforded 42, 55 and 67 as crude, which were then condensed with 43 or 68 to obtain α-amido-β-ketoester intermediates 44, 56 and 69 in 67%, 34% and 38% yields, respectively. The α-amido-β-ketoester intermediates were then cyclized using PPh$_3$/I$_2$/Et$_3$N to obtain oxazoles 45 (71%), 57 (78%) and 70 (65%). The corresponding thiazoles 46 and 58 were obtained by treating the α-amido-β-ketoester intermediates with lawessen's reagent. Subsequent removal of the Fmoc group with piperidine followed by condensation with pentenoyl N-hydroxy succinimide yielded the pentenoyl protected compounds with yields ranging from 33-52%. Hydrolysis of the methyl esters with 1M aq. LiOH followed by treatment with chloroacetonitrile and triethylamine yielded the corresponding cyanomethyl esters.

The cyanomethyl esters were used for the acylation of the dinucleotide pdCpA.[3] The acylation reaction was promoted by the use of sonication in 9:1 DMF-Et$_3$N and purified by reversed phase HPLC using semi-prep C$_{18}$ column, which provided the corresponding pdCpA derivatives.

Activated pdCpA derivatives were ligated to abbreviated tRNA$_{CUA}$ transcript using T4 RNA ligase and nine N-pentenoyl-aminoacyl-tRNA$_{CUA}$s were prepared.[4,5] The N-pentenoyl protection was removed by treatment with aqueous iodine for fifteen minutes. Removal of the protecting group was done immediately prior to the use of misacylated tRNAs in protein synthesis. The ligation of each pdCpA derivative to the abbreviated tRNA$_{CUA}$ was done with 100% efficiency.

Figure 3:
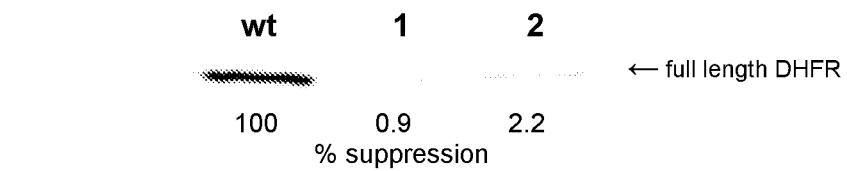
FIG. 3 depicts the translation of DHFR from wild-type (wt) and modified (lanes 1-2) (UAG codon in position 10) mRNA in the presence of different suppressor tRNA$_{CUA}$s using a S-30 preparation having wild-type ribosomes. Lane 2, nonacylated tRNA$_{CUA}$; lane 3, tRNA$_{CUA}$ activated with glycylphenylalanine (2). The suppression efficiency relative to wild type is shown below each lane.

Incorporation of Glycylphenylalanine (2) Using the Wild-Type Ribosome. The wild-type ribosomes synthesize polypeptide chains by incorporating one α-L-amino acid at a time via one monoacylated tRNA for each corresponding codon in the mRNA transcript.[6] Ribosome mediated sequential incorporation of two amino acids for one codon using bisacylated tRNAs has not been reported to date. Therefore, the ability of the wild-type ribosome to enable the incorporation of glycylphenylalanine using DHFR mRNA having a UAG codon at position 10 in the presence of glycylphenylalanyl-tRNA$_{CUA}$ was studied. The suppression efficiency of glycylphenylalanyl-tRNA$_{CUA}$ was compared to wild-type DHFR synthesis using an S-30 preparation having the wild-type ribosomes (FIG. 3). The suppression efficiency was ~2% for glycylphenylalanine. This data further proves that during translation, the wild-type ribosome cannot transfer a dipeptide from dipeptidyl-tRNA to a polypeptide chain.[7]

Incorporation of Dipeptides 2, 3 and 4 into DHFR Using the Modified Ribosomes. Initially, glycylphenylalanine (2) was chosen to screen the selected modified ribosomes for their ability to incorporate a dipeptide into DHFR. It was anticipated that minimal steric hindrance and more flexibility at the N-terminus of the dipeptide (a glycine residue) would enable optimal positioning of the amine for a nucleophilic attack in the PTC of the modified ribosomes. A modified DHFR construct, having a TAG codon in position 10 (pETDH10 plasmid) was used for the incorporation of glycylphenylalanine.

The suppression efficiencies were expressed relative to the wild-type DHFR synthesis. As a negative control, wild-type DHFR synthesis in the presence of nonacylated-tRNA$_{CUA}$ was measured for each experiment. The amounts of DHFR produced were quantified with a phosphoimager, which monitored the incorporation of $^{35}$S-methionine into DHFR. Using glycylphenylalanyl-tRNA$_{CUA}$, S-30 preparations having the modified ribosomes from clone groups 1, 2, 3 and 9 produced full length DHFR in ~9% yields relative to the wild-type DHFR synthesis (Table 3). The modified ribosomes from clone groups 4-8 incorporated glycylphenylalanine (2) with low yields (~2-4%). For dipeptide 2, best incorporation yields (up to 12%) were obtained by S-30 system having modified ribosomes from clone group 9 (2057AGUGAGA2063 and 2502AUCCGA2507). Therefore, using glycylphenylalanine (2) we identified four out of nine ribosomal variants (Table 3), which demonstrated reasonable incorporation of a dipeptide into protein using one codon in the mRNA transcript.

The next step was to test the incorporation of phenylalanylglycine (3) into DHFR, using modified ribosomes. Phenylalanylglycine has regio- and stereoisomerism analogous to the dipeptidyl moiety of puromycin derivative 1, which was used for the selection of modified ribosomes. We anticipated that the modified ribosomes would display enhanced incorporation of phenylalanylglycine (3) over glycylphenylalanine (2). To test this, we selected four modified ribosomes showing good results in our initial screening. Indeed, as shown in Table 3, all four modified ribosomes mediated enhanced incorporation of dipeptide 3 as compared to 2.

The best results were obtained by using modified ribosomes from clone groups 1 and 9, which incorporated dipeptide 3 into DHFR with ~14% (vs ~9% for 2) and ~13% (vs ~10% for 2) efficiency, respectively, in relative to the wild-type DHFR synthesis. Ribosomal clone 2 also showed good selectivity for dipeptide 3 over 2 (~12% vs ~8% suppression efficiency, respectively), whereas ribosomal clone 3 preferred dipeptide 3 only slightly over 2 (10% vs 9% suppression efficiency). The modified ribosomes tested for the incorporation of dipeptides 2 and 3 reasonably tolerated benzyl side chain both at the N- or C-terminus (phenylalanine residue).

Figure 4:
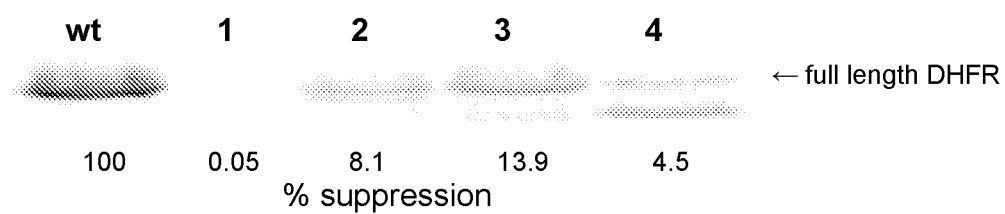
FIG. 4 depicts the translation of DHFR from wild-type (wt) and modified (lanes 1-4) (UAG codon in position 10) mRNA in the presence of different suppressor tRNA$_{CUA}$s using S-30 systems prepared from clone 010326R6. Lane 1, non acylated tRNA$_{CUA}$; lane 2, glycylphenylalanyl-tRNA$_{CUA}$; lane 3, phenylalanylglycyl-tRNA$_{CUA}$; lane 4, phenylalanylphenylalanyl-tRNA$_{CUA}$. The suppression efficiency relative to the wild type protein synthesis is shown below each lane.

Therefore, we also tested the incorporation of phenylalanylphenylalanyl (4) using ribosomal clone 1; however, a low ~4% suppression efficiency was obtained. Due to a poor incorporation of dipeptide 4 using ribosomal clone 1, we did not test other clones. FIG. 4 illustrates the formation of full length DHFR using an S-30 system prepared from ribosomal clone 010326R6 in presence of glycylphenylalanyl-tRNA$_{CUA}$, phenylalanylglycyl-tRNA$_{CUA}$ and phenylalanylphenylalanyl-tRNA$_{CUA}$.

Incorporation of Dipeptidomimetics 5, 6, 8, 9 and 10 into DHFR Using the Modified Ribosomes. After a successful demonstration of the incorporation of dipeptides into DHFR using modified ribosomes, we began investigating the ability to biosynthesize full length proteins in presence of suppressor tRNAs charged with dipeptidomimetics. So far, we have tested the incorporation of compounds 5, 6, 8, 9 and 10 (FIG. 2) into DHFR at position 10. Dipeptidomimetic 5 bears a minimum perturbation in the backbone, where an amide moiety has been replaced with a thioamide moiety. On the other hand dipeptidomimetics 6, 8, 9 and 10 are fluorescent structural analogues of the GFP chromophore.

Figure 5:
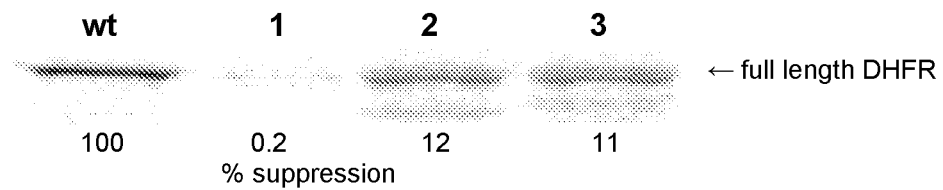
FIG. 5 depicts the translation of DHFR from wild-type and modified (lanes 1-3) (UAG codon in position 10) mRNA in the presence of different suppressor tRNA$_{CUA}$s using S-30 systems prepared from clone 010309R3. Lane 1, non acylated tRNA$_{CUA}$; lane 2, tRNA$_{CUA}$ activated with dipeptidomimetic 5; lane 3, tRNA$_{CUA}$ activated with dipeptidomimetic 6. The suppression efficiency relative to the wild type protein synthesis is shown below each lane.
Figure 6:
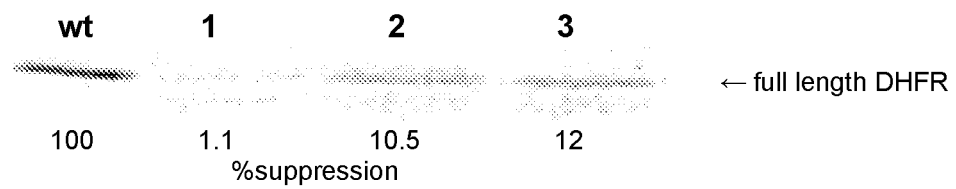
FIG. 6 depicts the translation of DHFR from wild-type and modified (lanes 1-3) (UAG codon in position 10) mRNA in the presence of different suppressor tRNA$_{CUA}$s using S-30 systems prepared from clone 010326R6. Lane 1, non acylated tRNA$_{CUA}$; lane 2, tRNA$_{CUA}$ activated with dipeptidomimetic 9; lane 3, tRNA$_{CUA}$ activated with dipeptidomimetic 10. The suppression efficiency relative to the wild type protein synthesis is shown below each lane.
Figure 7:
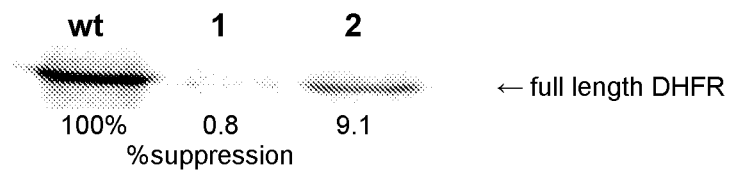
FIG. 7 depicts the translation of DHFR from wild-type and modified (lanes 1-2) (UAG codon in position 10) mRNA in the presence of different suppressor tRNA$_{CUA}$s using S-30 systems prepared from clone 010328R4. Lane 1, non acylated tRNA$_{CUA}$; lane 2, tRNA$_{CUA}$ activated with dipeptidomimetic 8. The suppression efficiency relative to the wild type protein synthesis is shown below each lane.

For the incorporation of 5 and 6, S-30 systems prepared from two ribosomal clones (clone group 1 and 9) were employed, whereas only clone group 1 was used for other three dipeptidomimetics 8-10. FIG. 5 illustrates the incorporation of dipeptidomimetics 5 and 6 into DHFR at position 10 using ribosomal clone 010309R3. Both ribosomal clone groups 1 and 9 incorporated thio-dipeptide 5 in ~11% suppression efficiency (Table 4) relative to the wild-type DHFR synthesis. Using ribosomal clone group 1, the suppression yields of 9 and 10 were ~11%, whereas 8 was incorporated with slightly lower yield of ~9%. FIGS. 6 and 7 demonstrate the incorporation of 9, 10 and 8 into DHFR at position 10, respectively.

Figure 8:
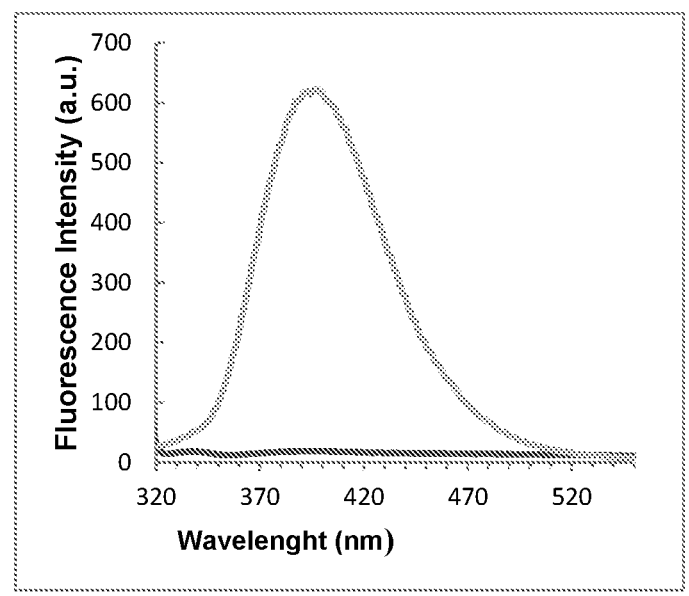
FIG. 8 shows the fluorescence emission spectrum of modified DHFR containing dipeptidomimetic 6 at position 10 (RED; top curve) and wild-type DHFR (BLUE; bottom line). The fluorescence emission was monitored from 350-450 nm following irradiation at 302 nm. The sample concentration was 10 nM for each.

Further, we prepared a modified DHFR having dipeptidomimetic 6 at position 10 at larger scale to investigate the fluorescence intensity of 6 in protein. The fluorescence emission spectra of wild-type DHFR and modified DHFR having 6 at position 10 were compared (FIG. 8) at 302 nm excitation wavelength. When excited at 302 nm, the modified DHFR had a fluorescence emission maximum at ~395 nm whereas no detectable fluorescence was observed for wild-type DHFR at similar protein concentrations.

Characterization of the incorporation of dipeptides and dipeptidomimetics into DHFR by MALDI-MS analysis of the peptides resulting from "in-gel" trypsin digestion. In order to provide direct evidence for the successful suppression of the UAG codon at position 10 of DHFR mRNA by a dipeptidyl-tRNA$_{CUA}$ or tRNA$_{CUA}$ activated with a dipeptidomimetic, three modified DHFRs putatively bearing glycylphenylalanine (2) (modified DHFR 1), dipeptidomimetic 5 (modified DHFR 2) or dipeptidomimetic 6 (modified DHFR 3) were prepared on a larger scale for an "in-gel" trypsin digestion followed by MALDI-MS analysis.[8] As a control, DHFR V10F was also prepared in amounts similar to the two modified DHFRs.

Figure 9A:
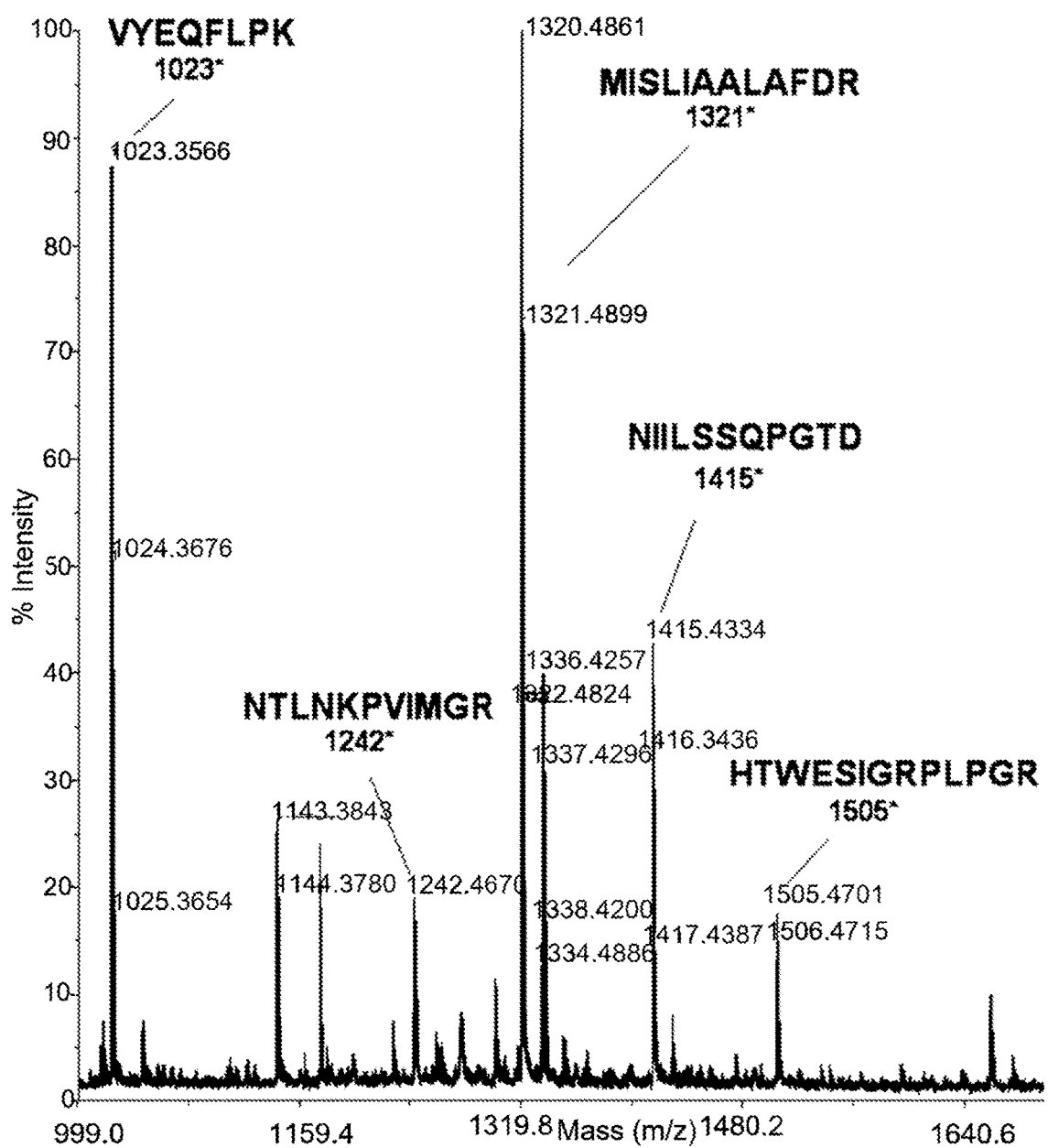
FIG. 9A depicts the MALDI-MS of tryptic fragments of DHFR V10F modified DHFR 1. Dipeptidomimetics 5 and 6 are denoted as 'x' in mass spectra. Mass range 1000-1600 Da (*=estimated value in Da).
Figure 9B:
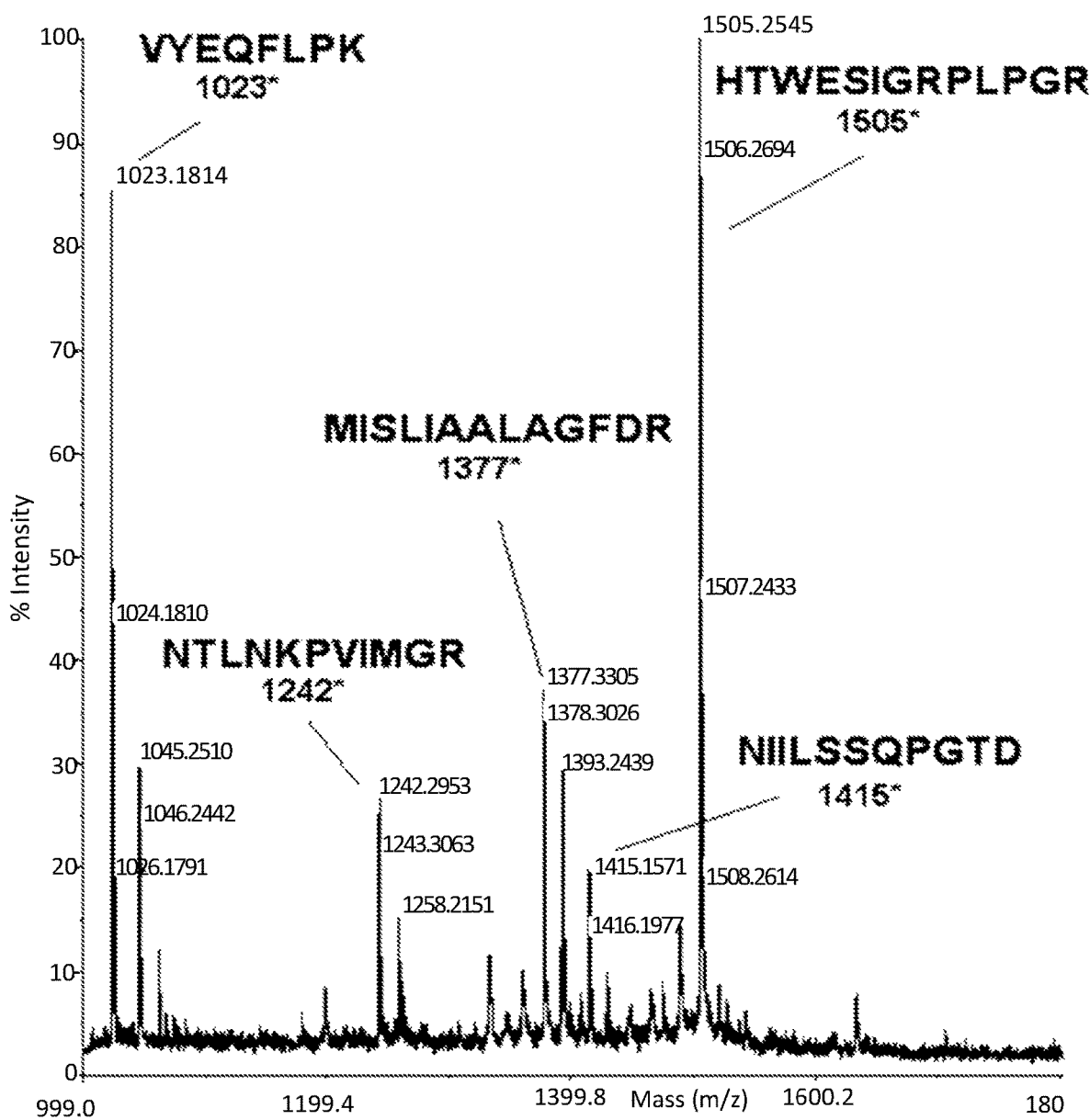
FIG. 9B depicts the MALDI-MS of tryptic fragments of DHFR V10F having glycylphenylalanine (2) at position 10. Dipeptidomimetics 5 and 6 are denoted as 'x' in mass spectra. Mass range 1000-1600 Da (*=estimated value in Da).

The modified DHFRs were purified by the use of Ni-NTA and DEAE-Sephadex chromatography followed by SDS-polyacrylamide gel electrophoresis. The tryptic digest of DHFR V10F gave an ion peak at m/z 1321.4899 (FIG. 9A) and confirmed the presence of peptide fragment (amino acids 1-12) having phenylalanine at position 10. For modified DHFR 1, a tryptic fragment encompassing amino acids 1-12 was anticipated to have a molecular mass of 1377 Da. As shown in FIG. 9B, there was an ion peak at m/z 1377.3305 consistent with the presence of glycylphenylalanine at position 10 of DHFR. During the preparation of tryptic digest, iodoacetamide is used to cap any reactive nucleophiles like sulfhydryl groups.

Figure 9C:
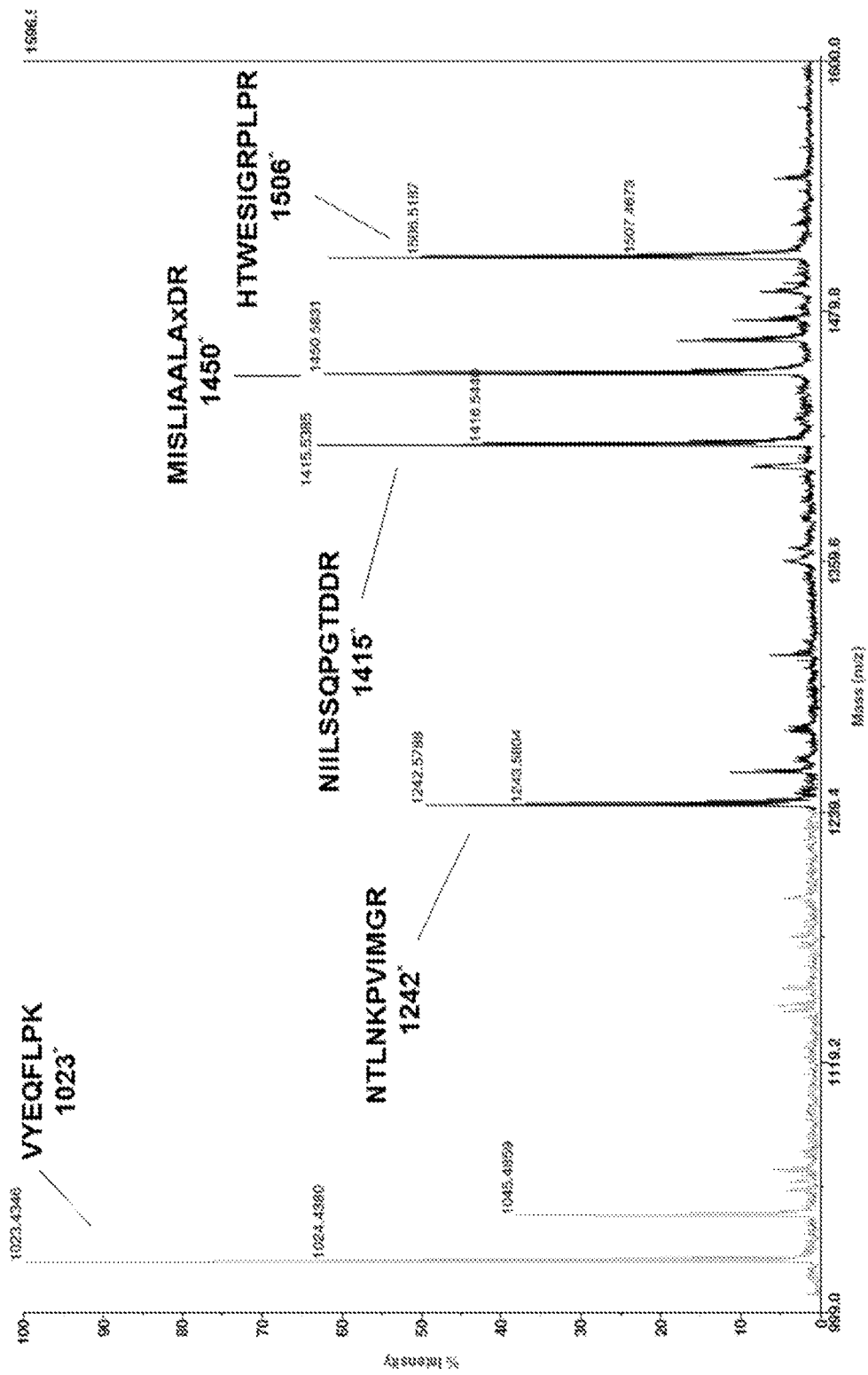
FIG. 9C depicts the MALDI-MS of tryptic fragments of modified DHFR 2 having dipeptidomimetic 5. Dipeptidomimetics 5 and 6 are denoted as 'x' in mass spectra. Mass range 1000-1600 Da (*=estimated value in Da).
Figure 9D:
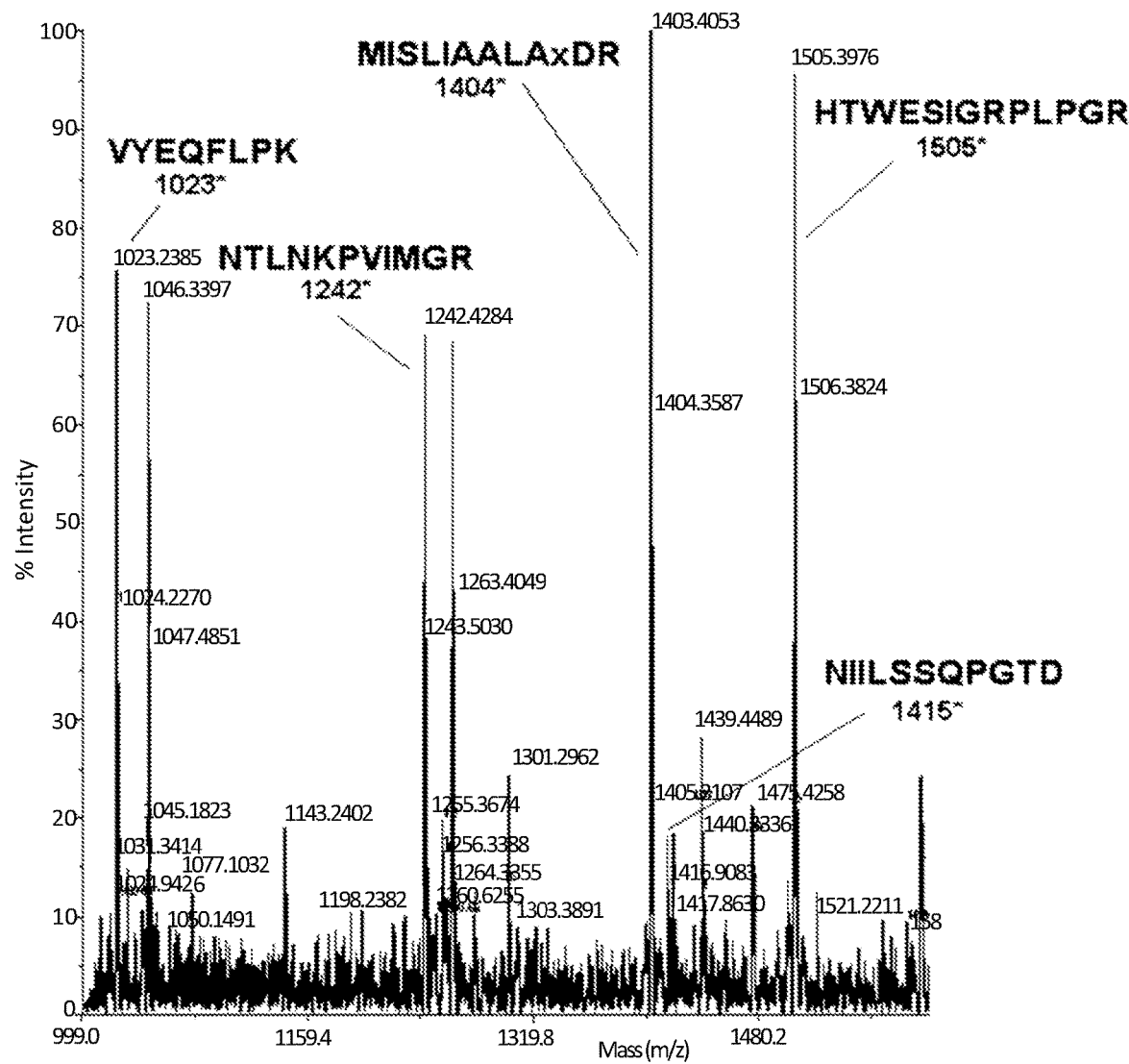
FIG. 9D depicts the MALDI-MS of tryptic fragments of modified DHFR 3 having dipeptidomimetic 6. Dipeptidomimetics 5 and 6 are denoted as 'x' in mass spectra. Mass range 1000-1600 Da (*=estimated value in Da).
Figure 10:
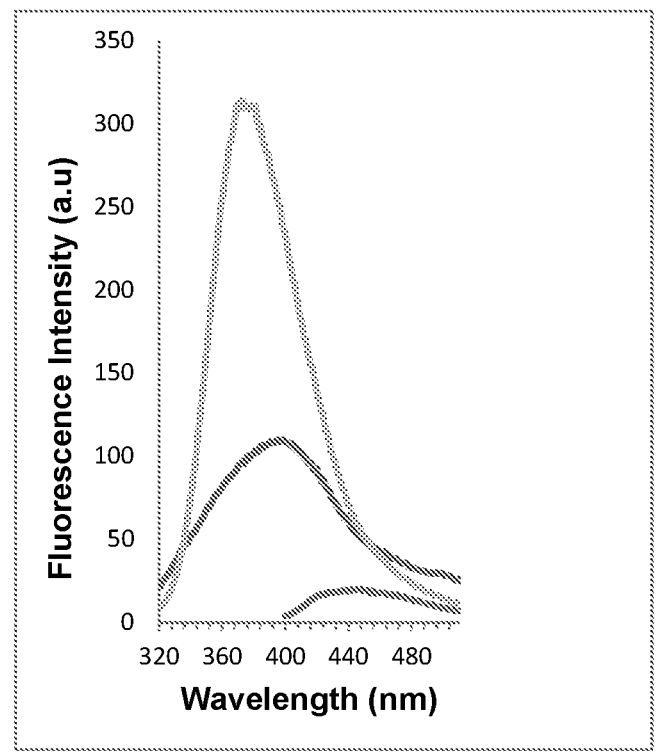
FIG. 10 shows the fluorescence emission spectra of artificial BFPs 1 (GREEN; top curve) and 2 (RED; middle curve) having dipeptidomimetic 6 and wild-type BFP (BLUE; bottom curve). Excitation wavelengths were 302 nm (artificial BFPs) and 375 nm (wt BFP).

For modified DHFR 2, we anticipated that the thio-amide group in 5 would react with iodoacetamide; a molecular mass of 1450 Da was expected for peptide (amino acids 1-12) having modified dipeptidomimetic 5. MALDI-MS spectrum, shown in FIG. 9C, had an ion peak at m/z 1450.5831, which demonstrates the presence of 5 in DHFR at position 10. As illustrated in FIG. 9D (modified DHFR 3), an ion peak at m/z 1404.3587 (estimated value 1404 Da) generated by the peptide having amino acids 1-12 confirmed the incorporation of dipeptidomimetic 6 into position 10 of DHFR. The other tryptic peptides encompassing amino acids 13-106 of DHFR were observed for DHFR V10F and the all three modified DHFRs. In replicate experiments, the (large) C-terminal fragment was never observed for any of the DHFRs.

Fluorescence Emission of an Artificial BFP Having Dipeptidomimetic 6. We designed fluorescent dipeptidomimetics 6-10 as stable analogues of GFP-chromophore. We anticipated their use to create artificial fluorescent proteins; to verify the same we replaced the chromophore of BFP with dipeptidomimetic 6 in order to prepare an artificial fluorescent protein. The fluorescence emission of 6 is near blue region of visible light spectrum (~400 nm). Therefore, we compared the fluorescence emission intensity of artificial FP (artificial BFP 1) having 6 at position 66 with wild-type BFP, which has a fluorescence emission ~450 nm. In wild-type BFP, a histidine residue is present at position 66. Wild-type and artificial BFP were prepared in a larger scale in a cell free translation system for fluorescence measurements.

A modified BFP construct, having a TAG codon in position 66 and a suppressor tRNA$_{CUA}$ activated with 6 were used for the preparation of artificial BFP 1. The protein concentrations were calculated following a standard BSA assay; the intensities of Coomassie Briallilant Blue staining of wild-type or modified DHFR samples were compared with a BSA standard of known concentration in an SDS-PAGE experiment. As illustrated from FIG. 11, fluorescence intensity of artificial BFP 1 (emission maximum ~375 nm) having 6 in position 66 is 20-fold greater than the wild-type BFP at similar protein concentrations. Position 66 is at the core of the β-barrel structure of BFP and is in a highly hydrophobic environment.

We were also interested to study fluorescence properties of 6 in protein, when it is exposed to an aqueous environment. For this reason, another modified BFP construct, having a TAG codon in position 39 and a glycine residue in position 66 was also prepared. This construct allowed us to prepare a protein having no fluorescent chromophore inside the β-barrel and 6 outside of the barrel exposed to solvent (artificial BFP 2). A glycine residue does not have an aromatic side chain and therefore, a fluorescent chromophore formation is highly unlikely. We predicted that the fluorescent dipeptidomimetic would give reduced fluorescence emission intensity with a red-shifted emission maximum due to a change from hydrophobic to hydrophilic environment. Indeed, as evident from FIG. 11, the fluorescent emission intensity of artificial BFP 2 having 6 in position 39 was diminished by 3-fold relative to artificial BFP having 6 in position 66. Moreover, the emission maximum was also red-shifted from ~375 nm to ~400 nm. Interestingly, the fluorescent intensity of artificial BFP 2 was 7-fold greater than the wild-type BFP.

Figure 11:
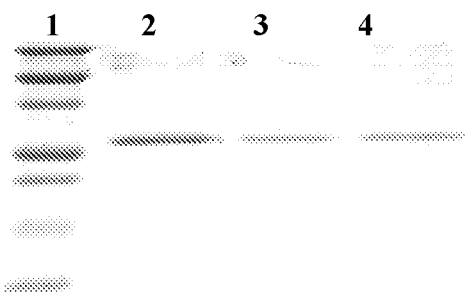
FIG. 11 depicts a SDS-PAGE gel stained with Coomassie Brilliant Blue; lane 1, standard protein ladder; lane 2, wt GFP; lane 3, artificial BFP 1; lane 4, artificial BFP 2.

Characterization of artificial BFPs 1 and 2 by MALDI-MS analysis of the peptides resulting from "in-gel" trypsin digestion. In order to provide direct evidence of presence of dipeptidomimetic 6 in artificial BFPs 1 and 2, an "in-gel" trypsin digestion followed by MALDI-MS analysis was performed.[8] As a control, wild-type GFP was also prepared in amounts similar to the two artificial BFPs. Proteins were purified by the use of Ni-NTA and DEAE-Sephadex chromatography followed by SDS-polyacrylamide gel electrophoresis (FIG. 11).

For artificial BFP 2, a tryptic fragment encompassing amino acids 27-41 (FSVSGEGEGDATxGK; SEQ ID NO. 1, dipeptidomimetic 6 denoted as x) was anticipated to have a molecular mass of 1570 Da, whereas the corresponding tryptic digest from wild-type GFP (FSVSGEGEGDATYGK; SEQ ID NO. 2) was expected to have a molecular mass of 1504 Da.

Figure 12A:
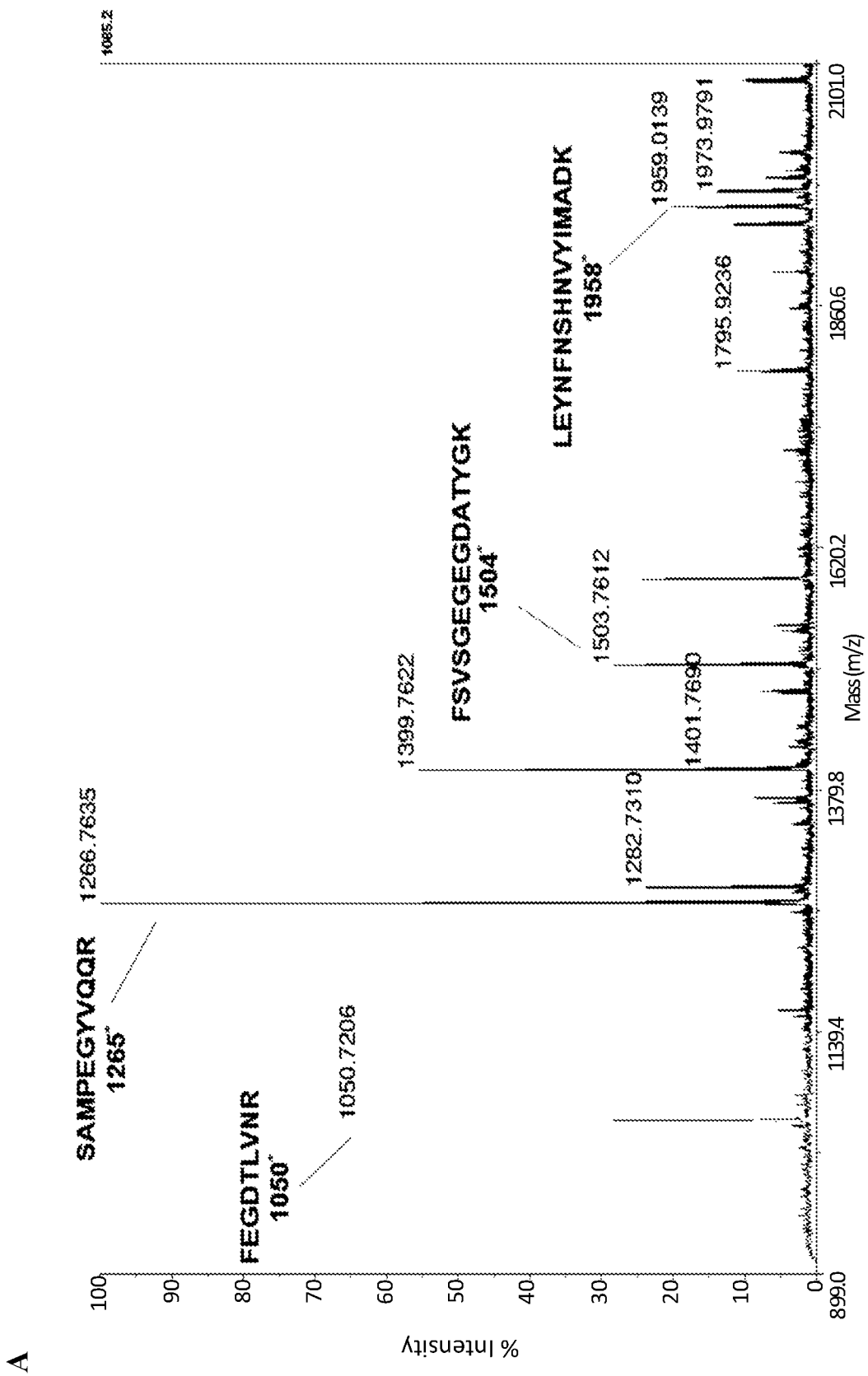
FIG. 12A depicts the MALDI-MS of tryptic fragments of wt GFP, mass range 900-2100 Da; (*=expected molecular mass in Da).
Figure 12B:
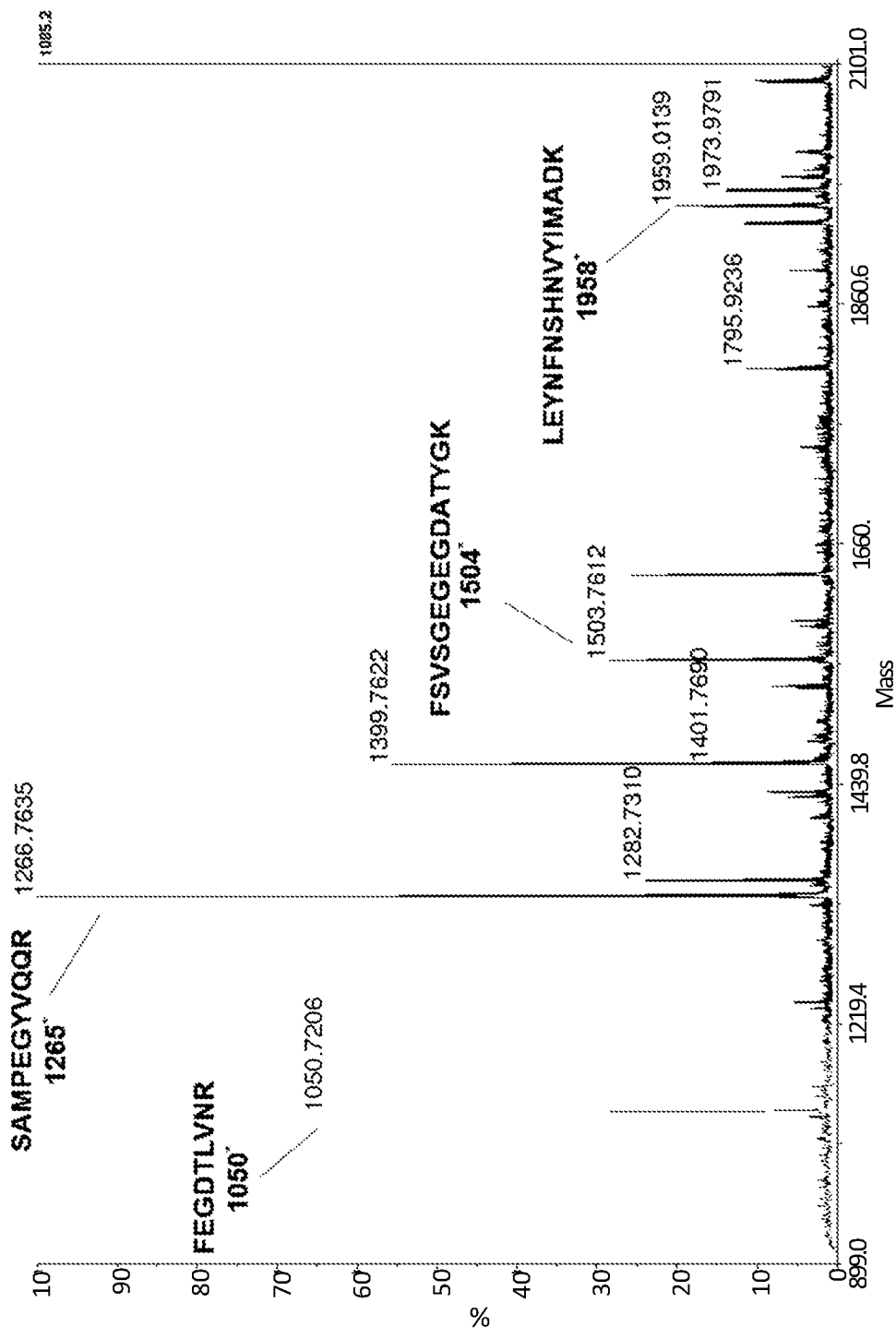
FIG. 12B depicts the MALDI-MS of tryptic fragments of artificial BFP 2, having dipeptidomimetic 6 at position 39, mass range 1000-2100. Dipeptidomimetic 6 is denoted as 'x'.

As shown in FIG. 12A, there was an ion peak at m/z 1503.7612 corresponding to wild-type GFP peptide FSVSGEGEGDATYGK (SEQ ID NO. 2), which shifted to ion peak at m/z 1570.4772 (FIG. 12B) consistent with the presence of dipeptidomimetic 6 at position 39 (FSVSGEGEGDATxGK; SEQ ID NO. 1) in artificial BFP 2. As discussed previously, iodoacetamide was used to cap any reactive nucleophiles like sulfhydryl groups. The tryptic digest from wild-type GFP (LPVPWPTLVTTFSYGVQ FSR; SEQ ID NO. 3) having serine-tyrosine-glycine at position 65-66-67 (in red or light greyscale in black and white reproductions) has a cysteine at position 70 (in green; i.e., the C following VQ in black and white reproductions). After chromophore formation and iodoacetamide capping of sulfhydryl group, the expected molecular mass of this peptide was 2437 Da.

Figure 12D:
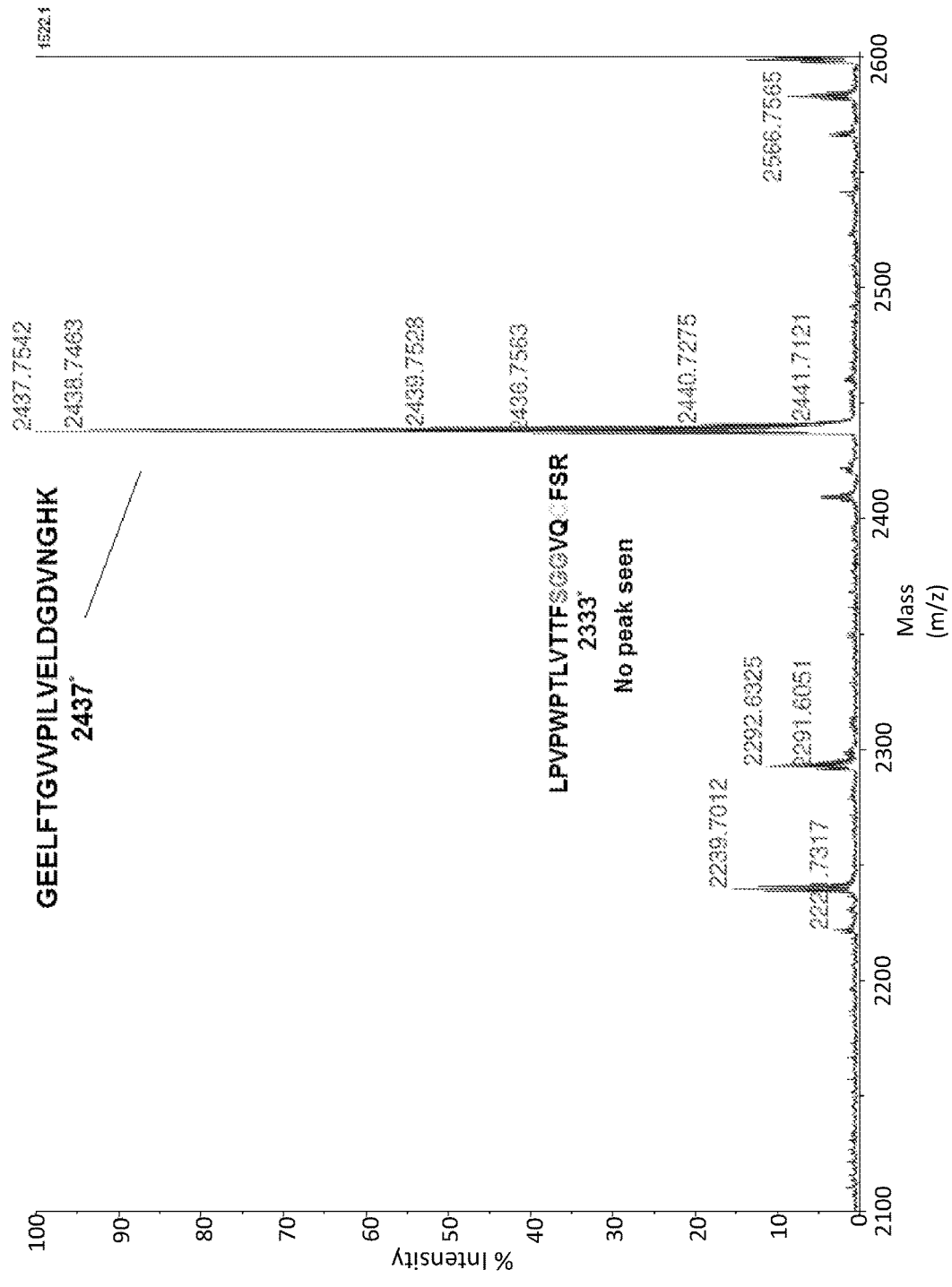
FIG. 12D depicts the MALDI-MS of tryptic fragments of wt GFP, mass range 2100-2600 Da. Serine-glycine-glycine residues are in red (grayscale in blank and white reproductions).

The tryptic digest corresponding to amino acids 4-26 (GEELFTGVVPILVELDGDVNGHK; SEQ ID NO. 4) also had an expected molecular mass of 2437 Da and as seen from FIG. 12C, there is an ion peak at m/z 2437.8581. To avoid this molecular mass overlap, a Y66G mutant GFP was prepared and an "in-gel" trypsin digestion followed by MALDI-MS analysis was performed. The anticipated molecular mass of the tryptic digest LPVPWPTLVTTFSGGVQ FSR, SEQ ID NO. 5, having glycine at position 66 was 2333 Da; surprisingly, no ion peak corresponding to molecular mass 2333 Da was seen in MALDI-MS (FIG. 12D). Even the tryptic digest (LPVPWPTLVTTFSxGVQ FSR; SEQ ID NO. 6) having dipeptidomimetic 6 at position 66 (in red) did not give any ion peak corresponding to expected molecular mass of 2523 Da.

Fluorescence Emission of an Artificial GFP Having Dipeptidomimetics 6 or 7. In Green fluorescent protein (GFP) is widely used as a fluorescent reporter in molecular and cell biology. *Aequorea victoria* GFP consists of 238 amino acid residues and has a 4-(p-hydroxybenzylidene) imidazolidin-5-one fluorophore, which forms by a posttranslational cyclization and oxidation of the polypeptide backbone, involving the Ser65-Tyr66-Gly67 residues. This results in an extended conjugated system capable of absorbing and emitting visible light. The maturation of the chromophore of GFP occurs spontaneously, which makes it an attractive molecular marker. The GFP chromophore has absorption peaks at 395 and 475 nm, usually assigned to the neutral and anionic forms of the chromophore, respectively, and an emission peak at 509 nm with a high fluorescence quantum yield (0.79). Numerous reports have described the study and spectral properties of novel fluorescent proteins and their chromophores. In comparison, there has been no report of the incorporation of a preformed fluorophore into a protein backbone by in vitro protein translation.

Compounds 6 and 7 are both strongly fluorescent. The free amino acids both have $\lambda_{ex}$ in the range 296-302 nm but the $\lambda_{em}$ of 7 is somewhat red-shifted compared to that of 6. After synthesis of the pdCpA derivatives of 6 and 7, the deprotected tRNAs were used in a cell-free coupled transcription-translation system containing an S-30 fraction prepared from *Escherichia coli*, programmed with a GFP analogue construct having a TAG codon at position 66 (pETGFP66 plasmid). The introduction of what may be regarded as "dipeptide analogues" into a single position of GFP reflected our analysis of the structure of that region of GFP, and the consequent belief that the substitution would be well tolerated. The S-30 system contained the modified ribosomes, the latter of which had altered peptidyltransferase centers, which enabled them to recognize dipeptides and dipeptide analogues in addition to α-L-amino acids. These modified ribosomes were selected by the use of a dipeptidylpuromycin derivative. Recognition of the dipeptidomimetic analogues by these modified ribosomes is presumably due to the fact that the distance between the amine and carboxylate groups in the dipeptidomimetics is similar to the distance between the free amine and carboxylate groups of a dipeptide. The suppression efficiencies were expressed relative to the wild-type GFP synthesis from the wild-type mRNA. As a negative control, wild-type GFP synthesis from the modified mRNA in the presence of nonacylated tRNA$_{CUA}$ was measured for each experiment. The amounts of GFP produced were quantified with a phosphoimager, which monitored the incorporation of $^{35}$S-methionine into proteins. S-30 preparations having the modified ribosomes from clone 010326R6 produced full length GFP in ~6.5% yield relative to wild-type GFP synthesis in case of 6, while in case of 7 the suppression yield was ~3.5% relative to wild-type GFP synthesis.

An elevated concentration (0.6-1.0 μg/μL) of the activated suppressor tRNA$_{CUA}$ was essential for successful translation, suggesting diminished binding of such species to one or more factors essential for protein synthesis. This concentration was quite high compared to the suppressor tRNA$_{CUA}$ concentration employed for the expression of α-amino acids (0.1-0.2 μg/μL). At lower concentrations of the aminoacyl-tRNA$_{CUA}$ minimal suppression was observed.

The GFP analogues having 6 and 7 at position 66 were prepared at larger scale and purified to permit study of the fluorescence intensity of 6 and 7 in the protein. The plasmid pETGFP66 was designed such that the translated protein had a hexahistidine moiety at its N-terminal and could be purified via Ni-NTA agarose chromatography. The purified proteins containing 6 and 7 were excited at 305 and 302 nm, respectively. The GFP analogue containing 6 exhibited a fluorescence emission maximum at ~375 nm whereas the protein carrying 7 had an emission maximum at ~403 nm. In addition, the fluorescence intensities of both the GFP analogues were compared with wild-type GFP. The fluorescence intensities of the modified GFP analogues were significantly greater than wild-type GFP at the same protein concentration.

Additional synthetic products and schemes are as follows.

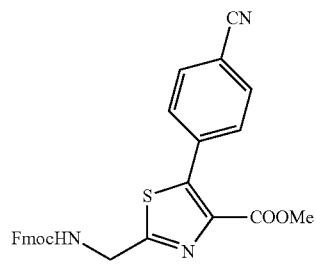

Methyl 2-((((9H-Fluoren-9-yl)methoxy)carbonylamino)methyl)-4-(4-cyanophenyl)thiazole-5-carboxylate (82). To a stirred solution of 0.30 g (0.60 mmol) of 81 in 5 mL of anhydrous THF was added 0.49 g (1.20 mmol) of the lawessen's reagent. The mixture was heated to reflux under argon atmosphere for 1 h. The yellow reaction mixture was diluted with 20 mL of saturated NaHCO$_3$ solution. The aqueous layer was extracted with two 25 mL portions of ethyl acetate. The organic layer was dried over anhydrous MgSO$_4$ and was concentrated under diminished pressure. The crude was utilized in the next reaction without further purification.

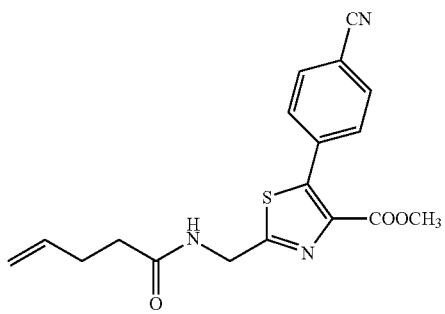 [SMILES: C=CCCC(=O)NCc1nc(C(=O)OC)c(-c2ccc(C#N)cc2)s1]

Methyl 4-(4-Cyanophenyl)-2-(pent-4-enamidomethyl)thiazole-5-carboxylate (83). To a stirred solution of the crude 82 in 4 mL of anhydrous CH$_2$Cl$_2$ was added 120 μL (0.10 g, 1.20 mmol) of piperidine dropwise. The reaction mixture was stirred at 25° C. under argon atmosphere for 2 h and was concentrated under diminished pressure. The residue was dissolved in 5 mL of anhydrous THF and 0.26 g (1.32 mmol) of 4-pentenoylsuccinimide was added followed by 83.0 mg (0.78 mmol) of Na$_2$CO$_3$. The mixture was stirred at room temperature for 3 h under argon atmosphere and was concentrated under diminished pressure. The residue was purified on a silica gel column (7×2 cm). Elution with 1:1 ethyl acetate-hexanes yielded 83 as a pale yellow solid: yield 47.0 mg (22% over two steps); silica gel TLC R$_f$ 0.29 (7:3 ethyl acetate-hexanes); $^1$H NMR (CDCl$_3$) δ 2.34-2.40 (m, 4H), 3.92 (s, 3H), 4.64 (d, 2H, J=6.0 Hz), 4.96-5.12 (m, 2H), 5.77-5.81 (m, 1H), 6.45 (br s, 1H), 7.72 (d, 2H, J=8.8 Hz), 8.18 (d, 2H, J=8.8 Hz); mass spectrum (APCI), m/z 356.0980 (M+H)$^+$ (C$_{18}$H$_{18}$N$_3$O$_3$S requires m/z 356.0991).

4-(4-Cyanophenyl)-2-(pent-4-enamidomethyl)thiazole-5-carboxyl pdCpA (85). A solution containing 6.0 mg (~15.8 μmol) of the crude cyanomethyl ester 84 and 6.0 mg (4.4 μmol) of the tris(tetrabutylammonium) salt of pdCpA in 100 μL of 9:1 DMF-Et$_3$N was subjected to sonication at room temperature for 4 h. The reaction mixture was purified by C$_{18}$ reversed phase HPLC (250×10 mm) using a gradient of 1% to 65% acetonitrile in 50 mM ammonium acetate, pH 4.5, over a period of 45 min. The fraction eluting at 17 min was collected and lyophilized to afford 85 as a white solid: yield 1.9 mg (45%). mass spectrum (MALDI), m/z 960.1815 (M+H)$^+$ (C$_{36}$H$_{40}$N$_{11}$O$_{15}$P$_2$S requires m/z 960.1823).

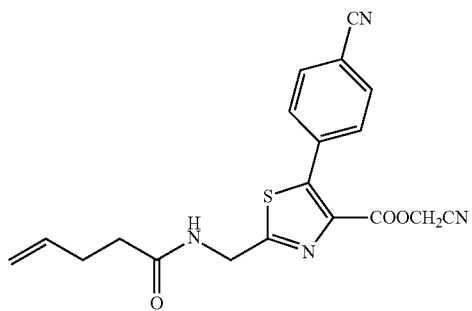

Cyanomethyl 4-(4-Cyanophenyl)-2-(pent-4-enamidomethyl)thiazole-5-carboxylate (84). To a stirred solution of 16.0 mg (0.05 mmol) of 83 in 0.4 mL of 3:1 THF-water was added 0.05 mL of 1 N LiOH. The mixture was stirred at 25° C. for 2 h. The aqueous layer was diluted with MeOH. The organic layer was dried over anhydrous Na$_2$SO$_4$ and was concentrated under diminished pressure. The crude product was dissolved in 2 mL of anhydrous DMF and 12.0 mg (0.14 mmol) of NaHCO$_3$ was added followed by 15.0 μL (18.0 mg, 0.24 mmol) of ClCH$_2$CN. The reaction mixture was stirred at 25° C. for 3 h under argon atmosphere. The crude was utilized in the next reaction without further purification.

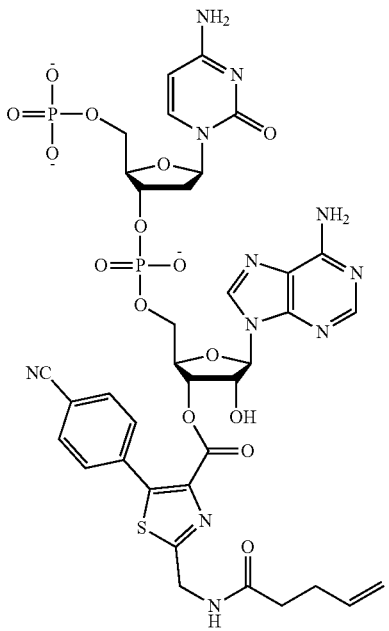

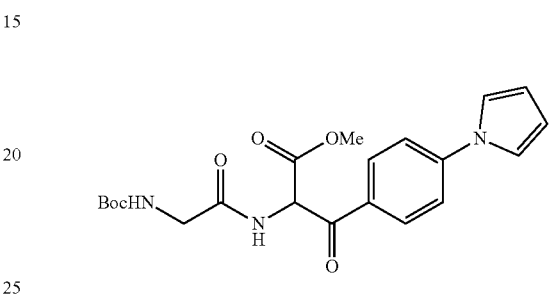

Methyl 3-(4-(1H-Pyrrol-1-yl)phenyl)-2-(2-((tert-butoxycarbonyl)amino)acetamido)-3-oxopropanoate (110). To a solution of 0.83 g (4.41 mmol) of acid 107 in 25 mL of THF were added 1.59 mL (1.16 g, 18.6 mmol) of Et$_3$N and 0.74 mL (0.78 g, 9.31 mmol) of isobutyl chloroformate. The reaction mixture was stirred at rt for 2 h to obtain the acid anhydride 108 which was used as crude for the next step. In a round-bottom flask, having solution of 1.17 g (4.63 mmol) of imine ester 35 in 100 mL of THF was added 4.63 mL (4.63 mmol) of 1M NaHMDS solution in THF at −78° C. After 30 min, the crude acid anhydride 108 was added to the reaction mixture and stirred at −78° C. for 2 h. The reaction mixture was quenched with aqueous HCl solution (6 M), until pH 2 was reached. The solvent was evaporated under diminished pressure to obtain the amine salt 109 as a colorless solid which was used for the next reaction without further purification.

To a solution of 0.85 g (4.85 mmol) of Boc-Gly-OH in 30 mL of DMF were added 2.14 g (4.85 mmol) of BOP and 0.67 mL (0.48 g, 4.85 mmol) of Et$_3$N. After 2 min, the amine salt 109 dissolved in 20 mL of DMF was added to the reaction mixture and stirred overnight at rt. The mixture was diluted with 300 mL of water and extracted with two 50-mL portions of EtOAc. The organic phase was dried (MgSO$_4$) and concentrated under diminished pressure. The residue was purified by chromatography on a silica gel column (10×4 cm). Elution with 1:1 hexanes-ethyl acetate gave the desired product 110 as a colorless foamy solid: yield 1.06 g (58% overall yield from acid 107); silica gel TLC R$_f$ 0.50 (1:1 hexanes-ethyl acetate); $^1$H NMR (CDCl$_3$) δ 1.44 (s, 9H), 3.71 (s, 3H), 3.93 (d, 2H, J=4.0 Hz), 5.39 (br s, 1H), 6.21 (d, 1H, J=8.0 Hz), 6.38-6.39 (m, 2H), 7.16-7.17 (m, 2H), 7.47 (d, 2H, J=12.0 Hz) 7.60 (d, 1H, J=8.0 Hz) and 8.17 (d, 2H, J=8.0 Hz); $^{13}$C NMR (CDCl$_3$) δ 28.5, 44.3, 53.5, 57.9, 80.5, 111.3, 119.1, 119.2, 119.4, 123.3, 130.8, 131.7, 131.8, 145.2, 150.7, 156.2, 167.2, 169.9 and 189.9; mass spectrum (APCI), m/z 416.1824 (M+H)$^+$ (C$_{21}$H$_{26}$N$_3$O$_6$ requires m/z 416.1822).

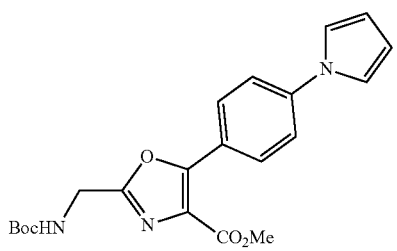 [SMILES: COC(=O)c1nc(CNC(=O)OC(C)(C)C)oc1-c1ccc(-n2cccc2)cc1]

Methyl 5-(4-(1H-Pyrrol-1-yl)phenyl)-2-(((tert-butoxycarbonyl)amino)methyl)oxazole-4-carboxylate (111). To a stirred solution of 0.23 g (0.88 mmol) of triphenylphosphine and 0.22 g (0.88 mmol) of iodine in 50 mL of $CH_2Cl_2$ was added 0.24 mL (0.17 g, 1.75 mmol) of triethylamine. The dark yellow solution was stirred for 5 min and 0.18 g (0.44 mmol) of keto-amide 110 was added to the reaction mixture and stirred at rt for 2 h. The reaction mixture was concentrated under diminished pressure and the residue was purified by chromatography on a silica gel column (10×1 cm). Elution with 1:1 hexanes-ethyl acetate gave the desired product 111 as a colorless solid: yield 0.11 g (63%); silica gel TLC $R_f$ 0.50 (1:1 hexanes-ethyl acetate); $^1$H NMR ($CDCl_3$) δ 1.45 (s, 9H), 3.91 (s, 3H), 4.51 (d, 2H, J=8.0 Hz), 5.34 (br s, 1H), 6.34-6.35 (m, 2H), 7.11-7.13 (m, 2H), 7.42-7.45 (m, 2H) and 8.10-8.13 (m, 2H); $^{13}$C NMR ($CDCl_3$) δ 28.5, 38.1, 53.6, 80.5, 111.4, 119.1, 119.3, 119.8, 120.2, 123.7, 123.7, 126.6, 128.1, 129.9, 142.0, 155.4, 155.7, 159.7 and 162.6; mass spectrum (APCI), m/z 398.1714 (M+H)$^+$ ($C_{21}H_{24}N_3O_5$ requires m/z 398.1716).

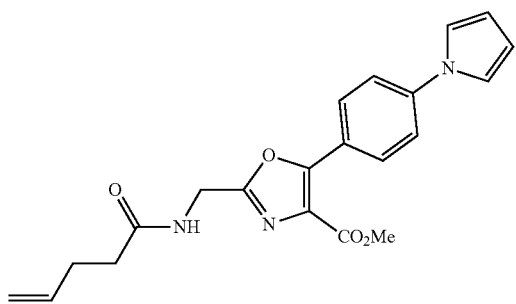 [SMILES: C=CCCC(=O)NCc1nc(C(=O)OC)c(-c2ccc(-n3cccc3)cc2)o1]

Methyl 5-(4-(1H-Pyrrol-1-yl)phenyl)-2-(pent-4-enamidomethyl)oxazole-4-carboxylate (112). To a solution of 0.20 g (0.55 mmol) of Boc-protected amine 111 in 10 mL of $CH_2Cl_2$ was added 10 mL of TFA. The reaction mixture was stirred overnight and concentrated under diminished pressure to obtain the deprotected amine which was used in next step without purification.

To the solution of deprotected amine in 15 mL of THF were added 0.11 g (0.55 mmol) of 4-pentenoyloxysuccinimide and 0.14 mL (0.10 g, 1.00 mmol) of $Et_3N$. The reaction mixture was stirred overnight at rt and concentrated under diminished pressure. The residue was purified by chromatography on a silica gel column (10×1 cm). Elution with 1:10 MeOH-ethyl acetate gave the desired product 112 as a colorless solid: yield 0.14 g (72%); silica gel TLC $R_f$ 0.75 (1:10 MeOH-ethyl acetate); $^1$H NMR ($CDCl_3$) δ 2.31-2.38 (m, 4H), 3.86 (s, 3H), 4.59 (d, 2H, J=4.0 Hz), 4.92-5.03 (m, 2H), 5.76-5.78 (m, 1H), 6.31-6.32 (m, 2H), 6.82-6.85 (m, 1H), 7.08-7.09 (m, 2H), 7.38-7.41 (m, 2H) and 8.04-8.06 (m, 2H); $^{13}$C NMR ($CDCl_3$) δ 29.5, 35.5, 36.6, 52.4, 111.4, 115.8, 119.0, 119.2, 119.3, 119.6, 122.9, 123.5, 126.4, 129.9, 131.6, 136.9, 142.0, 155.3, 159.4, 162.4 and 172.8; mass spectrum (APCI), m/z 380.1607 (M+H)$^+$ ($C_{21}H_{22}N_3O_4$ requires m/z 380.1610).

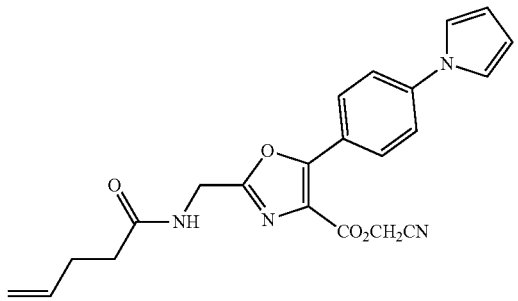

Cyanomethyl 5-(4-(1H-Pyrrol-1-yl)phenyl)-2-(pent-4-enamidomethyl)oxazole-4-carboxylate (113). To a solution of 0.12 g (0.31 mmol) of ester 112 in 3 mL of MeOH and 3 mL of THF was added 0.46 mL (0.46 mmol) of 1 M LiOH aqueous solution. The solution was stirred overnight at rt and concentrated under diminished pressure to obtain the acid which was used in next step without purification.

To a solution of the acid in 15 mL of DMF were added 0.06 mL (0.07 g, 0.93 mmol) of chloroacetonitrile and 0.22 mL (0.16 g, 1.54 mmol) of $Et_3N$. The reaction mixture was stirred overnight at rt and concentrated under diminished pressure. The residue was purified by chromatography on a silica gel column (10×1 cm). Elution with 1:10 MeOH-ethyl acetate gave the desired product 113 as a yellow solid: yield 70.0 mg (56%); silica gel TLC $R_f$ 0.75 (1:10 MeOH-ethyl acetate); $^1$H NMR ($CDCl_3$) δ 2.37-2.44 (m, 4H), 4.66 (d, 2H, J=8.0 Hz), 4.95 (s, 2H), 4.97-5.10 (m, 2H), 5.80-5.84 (m, 1H), 6.27 (br s, 1H), 6.38-6.39 (m, 2H), 7.15-7.16 (m, 2H), 7.48-7.51 (m, 2H) and 8.11-8.14 (m, 2H); $^{13}$C NMR ($CDCl_3$) δ 29.6, 35.7, 36.8, 49.1, 111.8, 114.3, 116.1, 119.2, 119.9, 122.9, 124.7, 130.0, 130.3, 13 7.0, 142.7, 157.4, 159.7, 160.6, 170.1 and 172.7; mass spectrum (APCI), m/z 405.1563 (M+H)$^+$ ($C_{22}H_{21}N_4O_4$ requires m/z 405.1563).

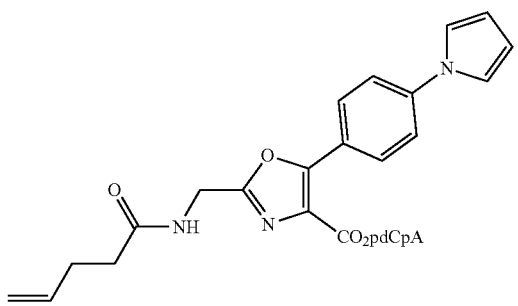

5-(4-(1H-Pyrrol-1-yl)phenyl)-2-(pent-4-enamidomethyl)oxazole-4-carboxylic acid pdCpA Ester (114). To a stirred solution containing 8.50 mg (6.37 μmol) of pdCpA tetrabutylammonium salt in 100 μL of 9:1 anhydrous DMF-$Et_3N$ was added 6.40 mg (15.9 μmol) of cyanomethyl ester 113. The reaction mixture was sonicated for 6 h. The reaction mixture was purified by $C_{18}$ reversed phase HPLC (250×10 mm) using a gradient of 1% to 65% acetonitrile in 50 mM ammonium acetate, pH 4.5, over a period of 1 h. The retention time of the desired product was 24.6 min. The fractions containing the product were lyophilized to afford 114 as a colorless solid: yield 2.0 mg (32%); mass spectrum (ESI), m/z 984.2356 (M+H)$^+$ (C$_{39}$H$_{44}$N$_{11}$O$_{16}$P$_2$ requires m/z 984.2364).

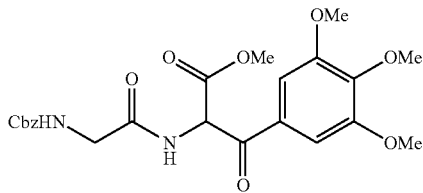 [SMILES: COC(=O)C(NC(=O)CNC(=O)OCc1ccccc1)C(=O)c1cc(OC)c(OC)c(OC)c1]

Methyl 2-(2-(Benzyloxycarbonyl)acetamido)-3-oxo-3-(3, 4,5-trimethoxyphenyl) propanoate (101). To a solution of 3.00 g (11.8 mmol) of imine ester 35 in 100 mL of THF was added 14.2 mL (14.2 mmol) of 1M NaHMDS solution in THF at −78° C. After 30 min, 2.73 g (11.8 mmol) of 3,4,5-trimethoxybenzoyl chloride dissolved in 15 mL of THF was added to the reaction mixture and stirred at −78° C. for 2 h. The reaction mixture was quenched with aqueous HCl solution (6 M), until pH 2 was reached. The solvent was evaporated under diminished pressure to obtain the amine salt 100 as a colorless solid which was used for the next reaction without further purification.

To a solution of the amine salt 100 in 150 mL of THF were added 7.25 g (23.7 mmol) of Cbz-Gly-OSu and 8.30 mL (6.05 g, 59.2 mmol) of Et$_3$N. The reaction mixture was stirred overnight at rt. The mixture was diluted with 300 mL of water and extracted with two 50-mL portions of EtOAc. The organic phase was dried (MgSO$_4$) and concentrated under diminished pressure. The residue was purified by chromatography on a silica gel column (10×4 cm). Elution with 1:1 hexanes-ethyl acetate gave the desired product 101 as a colorless solid: yield 4.43 g (79% overall yield from imine 35); silica gel TLC R$_f$ 0.50 (1:1 hexanes-ethyl acetate); $^1$H NMR (CDCl$_3$) δ 3.71 (s, 3H), 3.87-3.93 (m, 8H), 3.94 (s, 3H), 4.01 (s, 1H), 5.12 (s, 2H), 5.58 (br s, 1H), 6.16 (d, 1H, J=4.0 Hz), 7.31-7.34 (m, 5H), 7.39 (s, 2H) and 7.51 (d, 1H, J=8.0 Hz); $^{13}$C NMR (CDCl$_3$) δ 44.5, 53.5, 56.4, 56.5, 57.9, 61.2, 67.4, 106.6, 107.2, 107.4, 128.3, 128.4, 128.7, 128.8, 136.3, 144.1, 153.0, 153.1, 153.3, 156.8, 167.4, 169.3 and 189.8; mass spectrum (APCI), m/z 475.1721 (M+H)$^+$ (C$_{23}$H$_{27}$N$_2$O$_9$ requires m/z 475.1716).

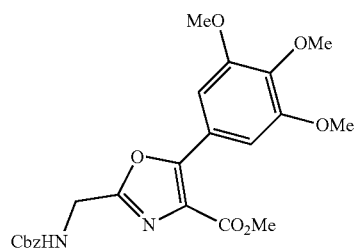 [SMILES: COC(=O)c1nc(CNC(=O)OCc2ccccc2)oc1-c1cc(OC)c(OC)c(OC)c1]

Methyl 2-((Benzyloxycarbonyl)methyl)-5-(3,4,5-trimethoxyphenyl)oxazole-4-carboxylate (102). To a stirred solution of 1.10 g (4.19 mmol) of triphenylphosphine and 1.06 g (4.17 mmol) of iodine in 50 mL of CH$_2$Cl$_2$ was added 1.16 mL (0.84 g, 8.34 mmol) of Et$_3$N. The dark yellow solution was stirred for 5 min and 0.99 g (2.08 mmol) of keto-amide 101 was added to the reaction mixture and stirred at rt for 2 h. The reaction mixture was concentrated under diminished pressure and the residue was purified by chromatography on a silica gel column (10×1 cm). Elution with 1:1 hexanes-ethyl acetate gave the desired product 102 as a colorless oil: yield 0.70 g (74%); silica gel TLC R$_f$ 0.50 (1:1 hexanes-ethyl acetate); $^1$H NMR (CDCl$_3$) δ 3.81-3.92 (m, 12H), 4.56 (d, 2H, J=4.0 Hz), 5.10 (s, 2H), 5.63 (br s, 1H), 7.23-7.29 (m, 5H) and 7.24 (s, 2H); $^{13}$C NMR (CDCl$_3$) δ 38.5, 52.6, 56.4, 56.5, 61.2, 67.5, 103.8, 106.1, 107.4, 121.8, 126.4, 128.3, 128.5, 128.7, 128.7, 132.2, 136.3, 140.3, 153.3, 156.0, 156.4, 158.9 and 162.6; mass spectrum (APCI), m/z 457.1617 (M+H)$^+$ (C$_{23}$H$_{25}$N$_2$O$_8$ requires m/z 457.1611).

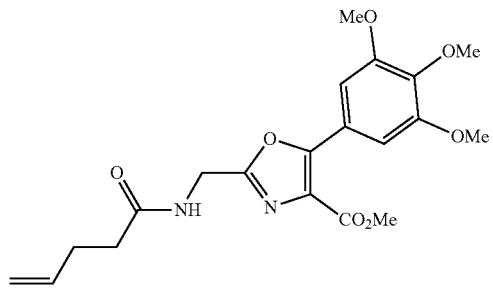 [SMILES: C=CCCC(=O)NCc1nc(C(=O)OC)c(-c2cc(OC)c(OC)c(OC)c2)o1]

Methyl 2-(Pent-4-enamidomethyl)-5-(3,4,5-trimethoxyphenyl)oxazole-4-carboxylate (103). To a solution of 0.36 g (0.79 mmol) of Cbz-protected amine 102 in 25 mL of EtOH was added 100 mg of 10% Pd/C. The suspension was stirred overnight under 1 atm of H$_2$. The reaction mixture was filtered through a celite pad and the filtrate was evaporated under reduced pressure to obtain the deprotected amine which was used in next step without purification.

To the solution of deprotected amine in 8 mL of THF were added 0.23 g (1.18 mmol) of 4-pentenoyloxysuccinimide and 0.33 mL (0.24 g, 2.37 mmol) of Et$_3$N. The reaction mixture was stirred overnight at rt and concentrated under diminished pressure. The residue was purified by chromatography on a silica gel column (10×1 cm). Elution with 1:10 MeOH-ethyl acetate gave the desired product 103 as a colorless oil: yield 0.11 g (35% yield over two steps); silica gel TLC R$_f$ 0.70 (1:10 MeOH-ethyl acetate); $^1$H NMR (CDCl$_3$) δ 2.34-2.42 (m, 4H), 3.86-3.93 (m, 12H), 4.61-4.66 (m, 2H), 4.97-5.08 (m, 2H), 5.81-5.82 (m, 1H), 6.35 (br s, 1H), 7.40-7.43 (m, 2H) and 7.61-7.64 (m, 1H); $^{13}$C NMR (100 MHz, CDCl$_3$) δ 29.6, 35.8, 36.8, 52.7, 56.6, 56.6, 61.2, 106.1, 116.0, 121.8, 126.4, 128.8, 132.2, 137.0, 140.4, 153.3, 156.1, 158.9, 162.6 and 172.6; mass spectrum (APCI), m/z 405.1656 (M+H)$^+$ (C$_{20}$H$_{25}$N$_2$O$_7$ requires m/z 405.1662).

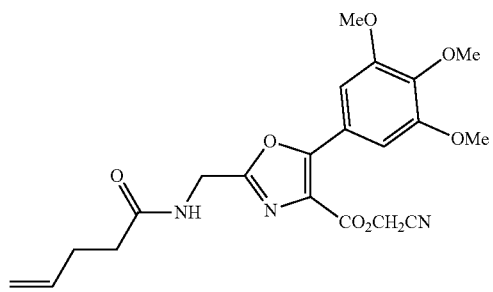

Cyanomethyl 2-(Pent-4-enamidomethyl)-5-(3,4,5-trimethoxyphenyl)oxazole-4-carboxylate (104). To a solution of 0.22 g (0.55 mmol) of ester 103 in 5 mL of MeOH and 5 mL of THF was added 1.11 mL (1.11 mmol) of 1 M LiOH aqueous solution. The solution was stirred overnight at rt and evaporated under reduced pressure to obtain the acid which was used in next step without purification.

To a solution of the acid in 3 mL of chloroacetonitrile was added 0.15 mL (0.11 g, 1.11 mmol) Et$_3$N. The reaction mixture was stirred overnight at rt and concentrated under diminished pressure. The residue was purified by chromatography on a silica gel column (10×1 cm). Elution with 1:10 MeOH-ethyl acetate gave the desired product 104 as a colorless solid: yield 80.0 mg (35% yield over two steps); silica gel TLC R$_f$ 0.70 (1:10 MeOH-ethyl acetate); $^1$H NMR (CDCl$_3$) δ 2.39-2.43 (m, 4H), 3.87-3.92 (m, 9H), 4.65-4.66 (m, 2H), 4.95 (s, 2H), 4.99-5.09 (m, 2H), 5.80-5.86 (m, 1H), 6.33 (br s, 1H) and 7.40-7.42 (m, 2H); $^{13}$C NMR (CDCl$_3$) δ 29.6, 35.7, 41.5, 49.1, 56.6, 56.6, 61.3, 106.2, 114.4, 116.0, 116.1, 121.1, 124.5, 128.8, 132.3, 137.0, 141.0, 153.5, 158.0, 160.7 and 172.8; mass spectrum (APCI), m/z 430.1607 (M+H)$^+$ (C$_{21}$H$_{24}$N$_3$O$_7$ requires m/z 430.1614).

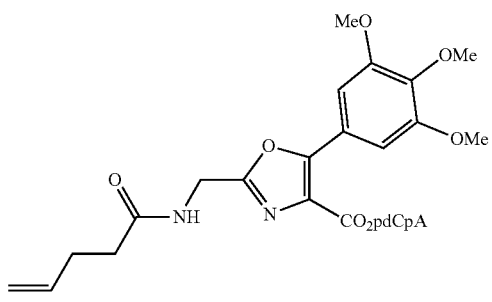

2-(Pent-4-enamidomethyl)-5-(3,4,5-trimethoxyphenyl) oxazole-4-carboxylic acid pdCpA ester (105). To a solution of 6.40 mg (15.0 μmol) of cyanomethyl ester 104 in 100 μL of 9:1 DMF-Et$_3$N was added 4.00 mg (3.00 μmol) of tris(tetrabutylammonium) salt of pdCpA and was subjected to sonication at room temperature for 2.5 h. The reaction mixture was purified by C$_{18}$ reversed phase HPLC (250×10 mm) using a gradient of 1% to 65% acetonitrile in 50 mM ammonium acetate, pH 4.5, over a period of 1 h. The retention time of the desired product was 19.5 min. The fractions containing the product were lyophilized to afford 105 as a colorless solid: yield 1.8 mg (59%); mass spectrum (ESI), m/z 1007.2334 (M–H)$^-$ (C$_{38}$H$_{45}$N$_{10}$O$_{19}$P$_2$ requires m/z 1007.2338).

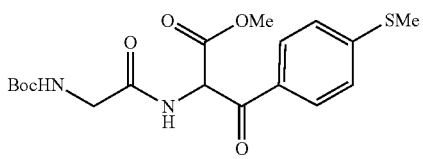 [SMILES: COC(=O)C(NC(=O)CNC(=O)OC(C)(C)C)C(=O)c1ccc(SC)cc1]

Methyl 2-(2-((tert-Butoxycarbonyl)amino)acetamido)-3-(4-(methylthio)phenyl)-3-oxo propanoate (89). To a solution of 0.53 g (1.82 mmol) of Boc-protected glycine methyl ester 87 in 30 mL of THF was added 2.18 mL (2.18 mmol) of 1M NaHMDS solution in THF at −78° C. After 30 min, 0.36 g (1.91 mmol) of 4-thiomethylbenzoyl chloride was added to the reaction mixture and stirred at −78° C. for 2 h. The reaction mixture was quenched with excess aqueous NH$_4$Cl solution and extracted with two 50-mL portions of EtOAc. The organic phase was dried (MgSO$_4$) and concentrated under diminished pressure. The residue was purified by chromatography on a silica gel column (10×4 cm). Elution with 3:1 hexanes-ethyl acetate gave the keto-ester 88 as a colorless foamy solid.

To the solution of keto-ester 88 in 10 mL of CH$_2$Cl$_2$ was added 10 mL of TFA and the reaction was stirred overnight at rt. The reaction mixture was concentrated under diminished pressure to obtain the amine which was used in next step without purification.

To a solution of 0.63 g (3.64 mmol) of Boc-Gly-OH in 15 mL of DMF was added 1.61 g (3.64 mmol) of BOP, 1.51 mL (1.10 g, 10.91 mmol) Et$_3$N and the amine (obtained from previous step). The reaction mixture was stirred overnight at rt. The reaction mixture was concentrated under diminished pressure and the residue was purified by chromatography on a silica gel column (10×4 cm). Elution with 1:1 hexanes-ethyl acetate gave the keto-amide 89 as a colorless oil: yield 0.52 g (72% overall yield from 87); silica gel TLC R$_f$ 0.50 (1:1 hexanes-ethyl acetate); $^1$H NMR (CDCl$_3$) δ 1.44 (s, 9H), 2.51 (s, 3H), 3.69 (s, 3H), 3.93 (br s, 2H), 5.54 (t, 1H, J=10.0 Hz), 6.18 (d, 1H, J=10.0 Hz), 7.26 (d, 2H, J=10.0 Hz), 7.68 (d, 1H, J=10.0 Hz), 7.99 (d, 2H, J=8.0 Hz); $^{13}$C NMR (CDCl$_3$) δ 14.6, 28.4, 44.1, 53.3, 57.7, 80.2, 125.0, 130.0, 130.1, 148.4, 156.1, 167.3, 169.8 and 190.1; mass spectrum (APCI), m/z 397.1429 (M+H)$^+$ (C$_{18}$H$_{25}$N$_2$O$_6$S requires m/z 397.1433).

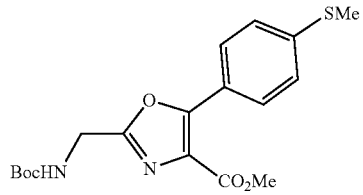 [SMILES: COC(=O)c1nc(CNC(=O)OC(C)(C)C)oc1-c1ccc(SC)cc1]

Methyl 2-(((tert-Butoxycarbonyl)amino)methyl)-5-(4-(methylthio)phenyl)oxazole4-carboxylate (90). To a stirred solution of 0.87 g (3.31 mmol) of triphenylphosphine and 0.83 g (3.30 mmol) of iodine in 50 mL of CH$_2$Cl$_2$ was added 0.92 mL (0.67 g, 6.60 mmol) of Et$_3$N. The dark yellow solution was stirred for 5 min and 0.65 g (1.65 mmol) of keto-amide 89 was added to the reaction mixture and stirred at rt for 2 h. The reaction mixture was concentrated under diminished pressure and the residue was purified by chromatography on a silica gel column (10×1 cm). Elution with 1:1 hexanes-ethyl acetate gave the desired product 90 as a yellow solid: yield 0.38 g (62%); silica gel TLC R$_f$ 0.50 (1:1 hexanes-ethyl acetate); $^1$H NMR (CDCl$_3$) δ 1.39 (s, 9H), 2.44 (s, 3H), 3.85 (s, 3H), 4.45 (d, 2H, J=4.0 Hz), 5.37 (br s, 1H), 7.21 (d, 2H, J=8.0 Hz) and 7.91 (d, 2H, J=8.0 Hz); $^{13}$C NMR (CDCl$_3$) δ 15.1, 28.4, 38.0, 52.4, 80.4, 123.0, 125.5, 126.2, 128.6, 142.4, 155.7, 155.8, 159.4 and 162.5; mass spectrum (APCI), m/z 379.1339 (M+H)$^+$ (C$_{21}$H$_{24}$N$_3$O$_5$ requires m/z 379.1328).

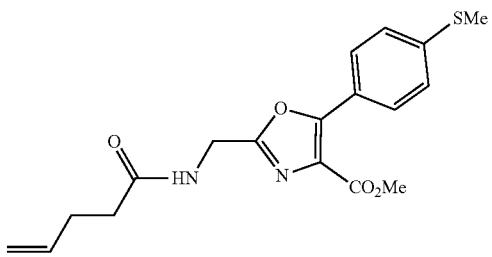 [SMILES: C=CCCC(=O)NCc1nc(C(=O)OC)c(-c2ccc(SC)cc2)o1]

Methyl 5-(4-(Methylthio)phenyl)-2-(pent-4-enamidomethyl)oxazole-4-carboxylate (91). To a solution of 0.39 g (1.02 mmol) of Boc-protected amine 90 in 10 mL of CH$_2$Cl$_2$ was added 10 mL of TFA. The reaction mixture was stirred overnight and concentrated under diminished pressure to obtain the deprotected amine which was used in next step without purification.

To the solution of deprotected amine in 10 mL of THF were added 0.50 g (2.56 mmol) of 4-pentenoyloxysuccinimide and 3 mL of aqueous saturated NaHCO$_3$. The reaction mixture was stirred overnight at rt and concentrated under diminished pressure. The residue was purified by chromatography on a silica gel column (10×1 cm). Elution with 1:10 MeOH-ethyl acetate gave the desired product 91 as a colorless solid: yield 0.23 g (62%); silica gel TLC R$_f$ 0.75 (1:10 MeOH-ethyl acetate); $^1$H NMR (CDCl$_3$) δ 2.30-2.38 (m, 4H), 2.47 (s, 3H), 3.87 (s, 3H), 4.59 (d, 2H, J=4.0 Hz), 4.93-5.04 (m, 2H), 5.75-5.79 (m, 1H), 6.58 (br s, 1H), 7.24 (d, 2H, J=8.0 Hz) and 7.91 (d, 2H, J=8.0 Hz); $^{13}$C NMR (CDCl$_3$) δ 15.1, 29.5, 36.7, 49.2, 52.5, 115.9, 122.8, 125.5, 126.2, 128.7, 137.0, 142.6, 156.0, 159.1, 162.5 and 172.7; mass spectrum (APCI), m/z 361.1232 (M+H)$^+$ (C$_{18}$H$_{21}$N$_2$O$_4$S requires m/z 361.1222).

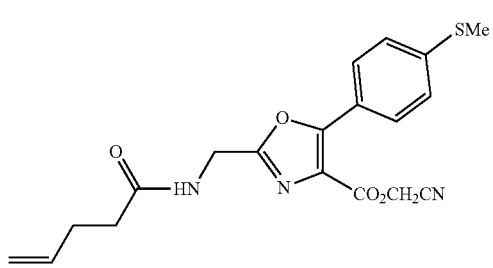

Cyanomethyl 5-(4-(Methylthio)phenyl)-2-(pent-4-enamidomethyl)oxazole-4-carboxylate (92). To a solution of 0.18 g (0.50 mmol) of ester 91 in 5 mL of MeOH and 5 mL of THF was added 1.25 mL (1.25 mmol) of 1 M LiOH aqueous solution. The solution was stirred overnight at rt, concentrated under diminished pressure to obtain the acid which was used in next step without purification.

To a solution of the acid in 1 mL of DMF were added 2 mL of chloroacetonitrile and 0.21 mL (0.16 g, 1.51 mmol) of Et$_3$N. The reaction mixture was stirred overnight at rt, concentrated under diminished pressure. The residue was purified by chromatography on a silica gel column (10×1 cm). Elution with 1:10 MeOH-ethyl acetate gave the desired product 92 as a yellow solid: yield 0.12 g (65%); silica gel TLC R$_f$ 0.75 (1:10 MeOH-ethyl acetate); $^1$H NMR (CDCl$_3$) δ 2.36-2.45 (m, 4H), 2.42 (s, 3H), 4.65 (d, 2H, J=8.0 Hz), 4.94 (s, 2H), 4.99-5.10 (m, 2H), 5.80-5.84 (m, 1H), 6.26 (br s, 1H), 7.31 (d, 2H, J=8.0 Hz) and 7.96 (d, 2H, J=8.0 Hz); $^{13}$C NMR (CDCl$_3$) δ 15.2, 29.6, 35.7, 36.8, 49.0, 114.3, 116.1, 122.2, 124.4, 125.7, 128.9, 137.0, 143.8, 158.0, 159.5, 160.6 and 172.7; mass spectrum (APCI), m/z 386.1176 (M+H)$^+$ (C$_{19}$H$_{20}$N$_3$O$_4$S requires m/z 386.1175).

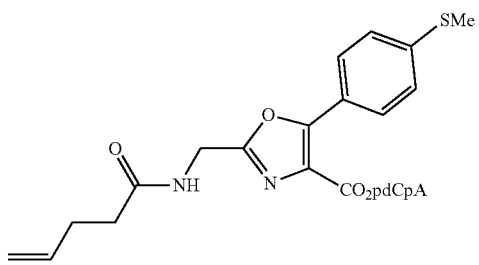

5-(4-(Methylthio)phenyl)-2-(pent-4-enamidomethyl)oxazole-4-carboxylic acid pdCpA ester (93). To a stirred solution containing 6.60 mg (5.00 μmol) of pdCpA tetrabutylammonium salt in 100 μL of 9:1 anhydrous DMF-Et$_3$N was added 9.50 mg (25.0 μmol) of cyanomethyl ester 92. The reaction mixture was sonicated for 6 h. The reaction mixture was purified by C$_{18}$ reversed phase HPLC (250×10 mm) using a gradient of 1% to 65% acetonitrile in 50 mM ammonium acetate, pH 4.5, over a period of 1 h. The retention time of the desired product was 20.3 min. The fractions containing the product were lyophilized to afford 93 as a colorless solid: yield 3.0 mg (63%); mass spectrum (ESI), m/z 963.1908 (M–H)$^-$ (C$_{36}$H$_{41}$N$_{10}$O$_{16}$P$_2$S requires m/z 963.1898).

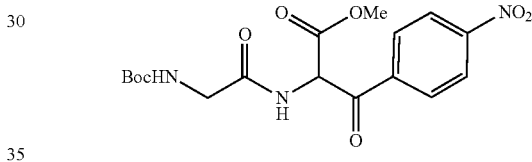

Methyl 2-(2-((tert-Butoxycarbonyl)amino)acetamido)-3-(4-nitrophenyl)-3-oxopropanoate (117). To a solution of 2.00 g (6.92 mmol) of Boc-protected glycine methyl ester 87 in 50 mL of THF was added 6.92 mL (6.92 mmol) of 1M NaHMDS solution in THF at –78° C. After 30 min, 1.28 g (6.92 mmol) of 4-nitrobenzoyl chloride was added to the reaction mixture and stirred at –78° C. for 2 h. The reaction mixture was quenched with excess aqueous NH$_4$Cl solution and extracted with two 50-mL portions of EtOAc. The organic phase was dried (MgSO$_4$) and concentrated under diminished pressure. The residue was purified by chromatography on a silica gel column (10×4 cm). Elution with 3:1 hexanes-ethyl acetate gave the keto-ester 116 as a white foamy solid.

To the solution of keto-ester 116 in 25 mL of CH$_2$Cl$_2$ was added 25 mL of TFA and the reaction was stirred overnight at rt. The reaction mixture was concentrated under diminished pressure to obtain the amine which was used in next step without purification.

To a solution of 1.45 g (8.30 mmol) of Boc-Gly-OH in 100 mL of DMF was added 3.67 g (8.30 mmol) of BOP, 2.88 mL (1.66 g, 20.75 mmol) of Et$_3$N and the amine (obtained from previous step). The reaction mixture was stirred overnight at rt. The reaction mixture was concentrated under diminished pressure and the residue was purified by chromatography on a silica gel column (10×4 cm). Elution with 1:1 hexanes-ethyl acetate gave the keto-amide 117 as a colorless solid: yield 0.65 g (24% overall yield from 87); silica gel TLC R$_f$ 0.50 (1:1 hexanes-ethyl acetate); $^1$H NMR (CDCl$_3$) δ 1.42 (s, 9H), 3.70 (s, 3H), 3.92 (br s, 2H), 5.28 (t, 1H, J=10.0 Hz), 6.17 (d, 1H, J=10.0 Hz), 7.30 (d, 2H, J=10.0 Hz), 7.52 (d, 1H, J=10.0 Hz), 8.15 (d, 2H, J=8.0 Hz); mass spectrum (APCI), m/z 396.1426 (M+H)+ (C17H22N3O8 requires m/z 396.1407).

172.8; mass spectrum (APCI), m/z 360.1199 (M+H)+ (C17H18N3O6 requires m/z 360.1196).

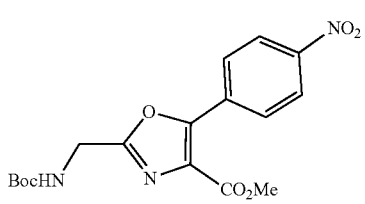

Methyl 2-(((tert-Butoxycarbonyl)amino)methyl)-5-(4-nitrophenyl)oxazole-4-carboxylate (118). To a stirred solution of 0.96 g (3.67 mmol) of triphenylphosphine and 0.93 g (3.67 mmol) of iodine in 50 mL of CH2Cl2 was added 1.02 mL (0.74 g, 7.34 mmol) of Et3N. The dark yellow solution was stirred for 5 min and 0.73 g (1.83 mmol) of keto-amide 117 was added to the reaction mixture and stirred at rt for 2 h. The reaction mixture was concentrated under diminished pressure and the residue was purified by chromatography on a silica gel column (10×1 cm). Elution with 1:1 hexanes-ethyl acetate gave the desired product 118 as a yellow solid: yield 0.40 g (58%); silica gel TLC $R_f$ 0.50 (1:1 hexanes-ethyl acetate); $^1$H NMR (CDCl3) δ 1.43 (s, 9H), 3.97 (s, 3H), 4.53 (d, 2H, J=4.0 Hz), 5.31 (br s, 1H) and 8.27 (s, 4H); $^{13}$C NMR (CDCl3) δ 28.5, 38.2, 52.9, 80.8, 123.9, 129.2, 129.3, 132.6, 148.6, 153.3, 155.7, 161.2 and 162.2; mass spectrum (APCI), m/z 378.1305 (M+H)+ (C17H20N3O7 requires m/z 378.1301).

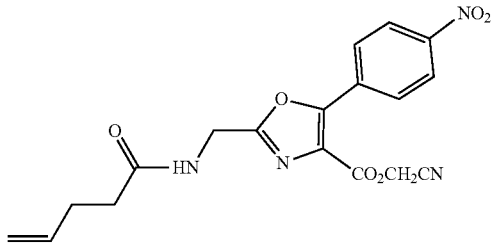

Cyanomethyl 5-(4-Nitrophenyl)-2-(pent-4-enamidomethyl)oxazole-4-carboxylate (120). To a solution of 65.0 mg (0.18 mmol) of ester 119 in 4 mL of MeOH and 4 mL of THF was added 0.36 mL (0.36 mmol) of 1 M LiOH aqueous solution. The solution was stirred overnight at rt and concentrated under diminished pressure to obtain the acid which was used in next step without purification.

To a solution of the acid in 3.00 mL of DMF were added 0.20 mL of chloroacetonitrile and 0.20 mL (0.14 g, 1.51 mmol) of Et3N. The reaction mixture was stirred overnight at rt, concentrated under diminished pressure. The residue was purified by chromatography on a silica gel column (10×1 cm). Elution with 1:10 MeOH-ethyl acetate gave the desired product 120 as a yellow solid: yield 37.0 mg (53%); silica gel TLC $R_f$ 0.75 (1:10 MeOH-ethyl acetate); $^1$H NMR (CDCl3) δ 2.39-2.54 (m, 4H), 4.69 (d, 2H, J=4.0 Hz), 4.98 (s, 2H), 5.01-5.11 (m, 2H), 5.81-5.88 (m, 1H), 6.15 (br s, 1H), 8.27 (d, 2H, J=4.0 Hz) and 8.35 (d, 2H, J=12.0 Hz); mass spectrum (APCI), m/z 385.1153 (M+H)+ (C18H17N4O6 requires m/z 385.1148).

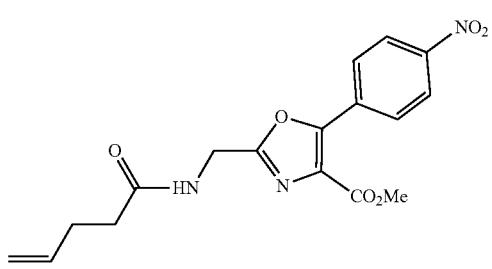 [SMILES: C=CCCC(=O)NCc1nc(C(=O)OC)c(-c2ccc([N+](=O)[O-])cc2)o1]

Methyl 5-(4-Nitrophenyl)-2-(pent-4-enamidomethyl)oxazole-4-carboxylate (119). To a solution of 0.40 g (1.06 mmol) of Boc-protected amine 118 in 10 mL of CH2Cl2 was added 10 mL of TFA. The reaction mixture was stirred overnight and concentrated under diminished pressure to obtain the deprotected amine which was used in next step without purification.

To the solution of deprotected amine in 15 mL of THF were added 0.42 g (2.13 mmol) of 4-pentenoyloxysuccinimide and 5 mL of aqueous saturated NaHCO3. The reaction mixture was stirred overnight at rt and concentrated under diminished pressure. The residue was purified by chromatography on a silica gel column (10×1 cm). Elution with 1:10 MeOH-ethyl acetate gave the desired product 119 as a colorless solid: yield 0.28 g (72%); silica gel TLC $R_f$ 0.75 (1:10 MeOH-ethyl acetate); $^1$H NMR (CDCl3) δ 2.34-2.43 (m, 4H), 3.94 (s, 3H), 4.67 (d, 2H, J=8.0 Hz), 4.97-5.08 (m, 2H), 5.78-5.82 (m, 1H), 6.38 (br s, 1H) and 8.28 (s, 4H); $^{13}$C NMR (CDCl3) δ 29.5, 35.6, 36.8, 53.0, 115.8, 116.1, 123.9, 129.2, 129.4, 132.5, 136.9, 148.6, 153.4, 160.8, 162.1 and

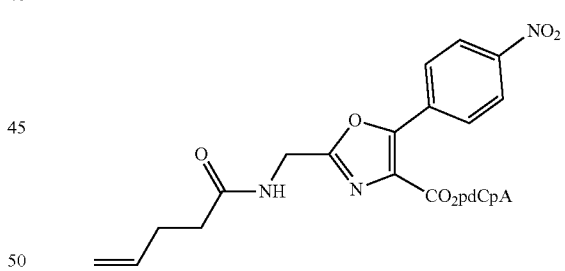

5-(4-Nitrophenyl)-2-(pent-4-enamidomethyl)oxazole-4-carboxylic acid pdCpA ester (121). To a stirred solution containing 18.0 mg (13.5 μmol) of pdCpA tetrabutylammonium salt in 100 μL of 9:1 anhydrous DMF-Et3N was added 13.0 mg (33.7 μmol) of cyanomethyl ester 120. The reaction mixture was sonicated for 6 h. The reaction mixture was purified by C18 reversed phase HPLC (250×10 mm) using a gradient of 1% to 65% acetonitrile in 50 mM ammonium acetate, pH 4.5, over a period of 1 hr. The retention time of the desired product was 25.3 min. The fractions containing the product were lyophilized to afford 121 as a colorless solid: yield 1.8 mg (14%); mass spectrum (ESI), m/z 962.1874 (M−H)− (C35H38N11O18P2 requires m/z 962.1871).

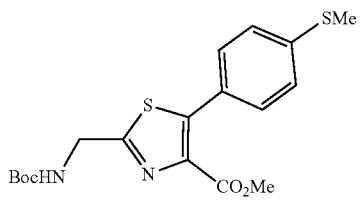 [SMILES: COC(=O)c1nc(CNC(=O)OC(C)(C)C)sc1-c1ccc(SC)cc1]

Methyl 2-(((tert-Butoxycarbonyl)amino)methyl)-5-(4-(methylthio)phenyl)thiazole-4-carboxylate (95). To a solution of 1.72 g (4.35 mmol) of keto-amide 89 in 80 mL of THF was added 2.46 g (6.09 mmol) of Lawesson's reagent and the mixture was refluxed for 4 hours. The reaction mixture was cooled to room temperature, concentrated under diminished pressure and the residue was purified by chromatography on a silica gel column (10×1 cm). Elution with 1:1 hexanes-ethyl acetate gave the desired product 95 as a colorless oil: yield 1.49 g (87%); silica gel TLC $R_f$ 0.50 (1:1 hexanes-ethyl acetate); $^1$H NMR (CDCl$_3$) δ 1.47 (s, 9H), 2.51 (s, 3H), 3.84 (s, 3H), 4.61 (d, 2H, J=4.0 Hz), 5.32 (br s, 1H), 7.26 (d, 2H, J=8.0 Hz) and 7.41 (d, 2H, J=8.0 Hz); $^{13}$C NMR (CDCl$_3$) δ 15.6, 28.6, 42.7, 52.6, 80.8, 125.8, 126.7, 130.5, 139.4, 141.0, 147.7, 155.9, 162.6 and 167.6; mass spectrum (APCI), m/z 395.1100 (M+H)$^+$ (C$_{18}$H$_{23}$N$_2$O$_4$S$_2$ requires m/z 395.1099).

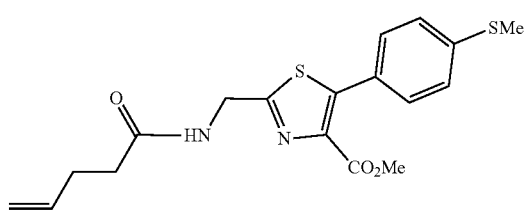 [SMILES: C=CCCC(=O)NCc1nc(C(=O)OC)c(-c2ccc(SC)cc2)s1]

Methyl 5-(4-(Methylthio)phenyl)-2-(pent-4-enamidomethyl)thiazole-4-carboxylate (96). To a solution of 1.30 g (3.30 mmol) of Boc-protected amine 95 in 25 mL of CH$_2$Cl$_2$ was added 25 mL of TFA. The reaction mixture was stirred overnight and concentrated under diminished pressure to obtain the deprotected amine which was used in next step without purification.

To the solution of deprotected amine in 50 mL of THF were added 1.63 g (8.25 mmol) of 4-pentenoyloxysuccinimide and 20 mL of aqueous saturated NaHCO$_3$. The reaction mixture was stirred overnight at rt and concentrated under diminished pressure. The residue was purified by chromatography on a silica gel column (10×1 cm). Elution with 1:10 MeOH-ethyl acetate gave the desired product 96 as a colorless solid: yield 1.06 g (86%); silica gel TLC $R_f$ 0.75 (1:10 MeOH-ethyl acetate); $^1$H NMR (CDCl$_3$) δ 2.39 (s, 4H), 2.49 (s, 3H), 3.80 (s, 3H), 4.71 (d, 2H, J=4.0 Hz), 4.96-5.06 (m, 2H), 5.76-5.83 (m, 1H), 7.23 (d, 2H, J=4.0 Hz), 7.34 (d, 2H, J=4.0 Hz) and 7.44 (br s, 1H); $^{13}$C NMR (CDCl$_3$) δ 15.1, 29.3, 35.2, 41.1, 52.1, 115.6, 115.6, 125.3, 126.1, 130.0, 136.7, 138.7, 140.7, 147.3, 162.3, 166.6 and 173.0; mass spectrum (APCI), m/z 377.0991 (M+H)$^+$ (C$_{18}$H$_{21}$N$_2$O$_3$S$_2$ requires m/z 377.0994).

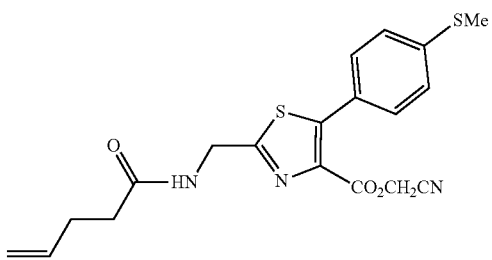

Cyanomethyl 5-(4-(Methylthio)phenyl)-2-(pent-4-enamidomethyl)thiazole-4-carboxylate (97). To a solution of 0.42 g (1.12 mmol) of ester 96 in 5 mL of MeOH and 5 mL of THF was added 2.79 mL (2.79 mmol) of 1 M LiOH aqueous solution. The solution was stirred overnight at rt, concentrated under diminished pressure to obtain the acid which was used in next step without purification.

To a solution of the acid in 3 mL of DMF were added 2 mL of chloroacetonitrile and 0.50 mL (0.36 g, 3.60 mmol) of Et$_3$N. The reaction mixture was stirred overnight at rt, concentrated under diminished pressure. The residue was purified by chromatography on a silica gel column (10×1 cm). Elution with 1:10 MeOH-ethyl acetate gave the desired product 97 as a yellow solid: yield 0.25 g (55%); silica gel TLC $R_f$ 0.75 (1:10 MeOH-ethyl acetate); $^1$H NMR (CDCl$_3$) δ 2.33-2.37 (m, 4H), 2.47 (s, 3H), 4.67 (d, 2H, J=4.0 Hz), 4.81 (s, 2H), 4.95-5.04 (m, 2H), 5.77-5.78 (m, 1H), 6.73 (br s, 1H), 7.22 (d, 2H, J=8.0 Hz) and 7.33 (d, 2H, J=8.0 Hz); $^{13}$C NMR (CDCl$_3$) δ 15.4, 29.5, 34.1, 35.6, 49.3, 114.3, 116.1, 125.7, 125.8, 130.3, 130.4, 136.9, 141.8, 150.6, 160.3, 166.8 and 173.1; mass spectrum (APCI), m/z 402.0958 (M+H)$^+$ (C$_{19}$H$_{20}$N$_3$O$_4$S requires m/z 402.0946).

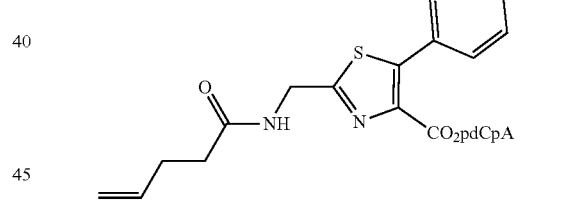

5-(4-(Methylthio)phenyl)-2-(pent-4-enamidomethyl)thiazole-4-carboxylic acid pdCpA ester (98). To a stirred solution containing 7.50 mg (18.0 μmol) of pdCpA tetrabutylammonium salt in 100 μL of 9:1 anhydrous DMF-Et$_3$N was added 10.0 mg (7.00 μmol) of cyanomethyl ester 97. The reaction mixture was sonicated for 6 h. The reaction mixture was purified by C$_{18}$ reversed phase HPLC (250×10 mm) using a gradient of 1% to 65% acetonitrile in 50 mM ammonium acetate, pH 4.5, over a period of 1 h. The retention time of the desired product was 24.2 min. The fractions containing the product were lyophilized to afford 98 as a colorless solid: yield 2.0 mg (27%); mass spectrum (ESI), m/z 979.1682 (M−H)$^-$ (C$_{36}$H$_{41}$N$_{10}$O$_{15}$P$_2$S$_2$ requires m/z 979.1682).

Figure 13:
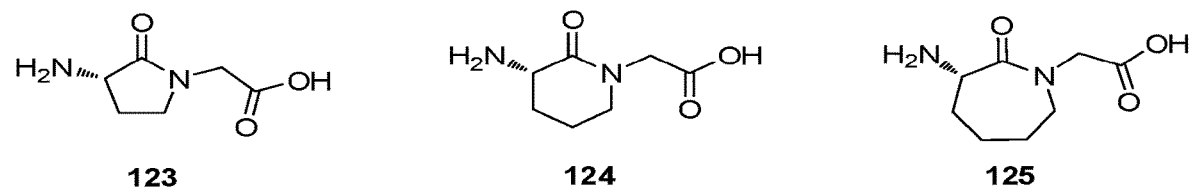
FIG. 13 depicts additional compounds.

Lactam-constrained dipeptide and its pdCpA derivative. In scheme 15, the five-membered lactam intermediate 126 (see FIG. 13) was prepared by cyclization of Boc-L-DAB-OH in DMF at a 10 mM concentration, with BOP as coupling reagent in the presence of sodium bicarbonate as "insoluble base" in 54% yield. Alkylation of the amide with benzyl bromoacetate afforded compounds 127 in 60% yield. Deprotection of the Boc group by TFA produced compound 128 in quantitive yield, and then deprotection of the benzyl group by hydrogenolysis produced compound 123 in quantitive yield. The key intermediate 130 was obtained in two steps.

Initially, 123 was treated with 4-pentenoylsuccinimide in the presence of DIPEA to obtain acid 129, which was treated with chloroacetonitrile in anhydrous DMF in the presence of Et$_3$N afforded the desired cyanomethyl ester 130 as an oil in 7% yield over two steps. Coupling of the cyanomethyl ester 130 with pdCpA tetrabutylammonium salt in anhydrous DMF afforded the five-membered dipeptide pdCpA ester 131 in 9% yield. The six and seven-membered lactam-dipeptide pdCpA esters 138 and 145 were prepared analogously, as outlined in schemes 2 and 3, respectively. Finally, the aminoacylated dinucleotides were ligated to an abbreviated tRNA$_{CUA}$-C$_{OH}$ transcript in the presence of T4 RNA ligase and ATP to afford the corresponding pentenoyl-aminoacyl-tRNAs 132, 139 and 146.

Experimental (for the chemical structures corresponding to the numeric references below, see Schemes 15-18 at the end of the Detailed Description).

All experiments requiring anhydrous conditions were conducted in flame-dried glassware fitted with rubber septa under a positive pressure of dry nitrogen, unless otherwise noted. Reactions were performed at room temperature unless otherwise indicated. Analytical thin layer chromatography (TLC) was performed using glass plates pre-coated with silica gel (0.25 mm, 60 Å pore size, 230-400 mesh, Silicycle) impregnated with a fluorescent indicator (254 nm). TLC plates were visualized by exposure to ultraviolet light (UV). Flash column chromatography was performed employing silica gel (60 Å pore size, 40-63 μm, standard grade, Silicycle). An acetone cooling bath was cooled to the appropriate temperature by the addition of small portions of dry ice.

$^1$H NMR and $^{13}$C NMR spectra were recorded on Varian INOVA 400 (400 MHz) and Varian INOVA 500 (500 MHz) spectrometers at 25° C. Proton chemical shifts are expressed in parts per million (ppm, δ scale) and are referenced to residual protium in the NMR solvent (CDCl$_3$, DMSO-d$_6$ or CD$_3$OD). Splitting patterns are designated as follows: s, singlet; br s, broad singlet; d, doublet; dd, doublet of doublets; t, triplet; q, quartet; m, multiplet. High resolution mass spectra were obtained at the Arizona State University CLAS High Resolution Mass Spectrometry Facility or the Michigan State University Mass Spectrometry Facility. HPLC purification was performed with a Waters 600 pump coupled with a Varian ProStar 340 detector and a Grace Econosil C$_{18}$ column (250×10 mm, 5 μm). The tetra-n-butylammonium (TBA) salt of pdCpA was prepared using Dowex 50W×8, 200-400 mesh, preequilibrated as its TBA form.

Synthesis of Lactam-Constrained Dipeptide and its pdCpA Derivatives

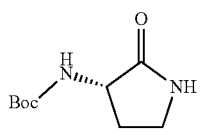

(S)-tert-Butyl (2-Oxopyrrolidin-3-yl)carbamate (126). To a solution of 0.60 g (2.75 mmol) of BOC-L-DAB-OH in 275 mL of DMF at a 10 mM concentration were added 1.22 g (2.75 mmol) of BOP and 1.16 g (20.0 mmol) of sodium bicarbonate. After 12 h stirring at room temperature, the mixture was concentrated to a small volume (around 5 mL) under reduced pressure. The concentrated mixture was diluted with water and saturated sodium bicarbonate solution (1:1, 100 mL) and extracted with three 100-mL portions of EtOAc. The combined organic extracts were washed with 200 mL of water and 200 mL of brine, dried over Na$_2$SO$_4$, filtered, and concentrated under reduced pressure to afford a residue that crystallized upon trituration in 100 mL of ether and filtered to afford 126 as a colorless solid: yield 296 mg (54%); mp 161-164° C. (lit.$^1$ 168-171° C.); silica gel TLC R$_f$0.55 (10:1 DCM-MeOH); $^1$H NMR (CDCl$_3$) δ 1.42 (s, 9H), 1.93-2.01 (m, 1H), 2.60-2.70 (m, 1H), 3.28-3.42 (m, 2H), 4.05-4.20 (m, 1H), 5.25 (s, 1H) and 6.85 (br s, 1H); $^{13}$C NMR (CDCl$_3$) δ 28.3, 30.0, 39.2, 51.7, 79.9, 155.9 and 176.1.

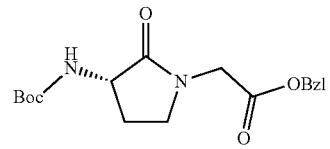

(S)-Benzyl 2-(3-((tert-Butoxycarbonyl)amino)-2-oxopyrrolidin-1-yl)acetate (127). A solution of 290 mg (1.45 mmol) of 126 in 5 mL of anhydrous THF was added to a suspension of 116 mg (2.90 mmol) of sodium hydride (60% dispersion in mineral oil) in 10 mL of anhydrous THF. The reaction was stirred at room temperature for 15 min, and 241 μL (348 mg, 1.52 mmol) of benzyl bromoacetate was added. After 5 h stirring at room temperature, 30 mL of EtOAc was added, followed by 20 mL of water. The organic phase was washed with 20 mL of brine, dried over Na$_2$SO$_4$, filtered and concentrated under reduced pressure to afford an oily residue. The residue was purified by chromatography on a silica gel column (10×2 cm). Elution with 3:1 hexanes-EtOAc afforded 127 as a colorless oil: yield 301 mg (60%); silica gel TLC R$_f$0.38 (3:1 hexanes-EtOAc); $^1$H NMR (CDCl$_3$) δ 1.39 (s, 9H), 1.80-1.96 (m, 1H), 2.50-2.62 (m, 1H), 3.29 (dd, 1H, J=9.2 and 8.4 Hz), 3.40 (td, 1H, J=9.6 and 6.7 Hz), 3.98 (d, 1H, J=17.7 Hz), 4.15 (d, 2H, J=17.7 Hz), 5.10 (s, 2H), 5.24 (s, 1H) and 7.21-7.41 (m, 5H); $^{13}$C NMR (CDCl$_3$) δ 28.0, 28.3, 44.5, 44.6, 51.9, 67.1, 80.0, 128.3, 128.5, 128.6, 135.1, 155.7, 168.1 and 173.0.

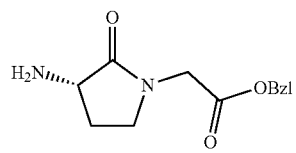

(S)-Benzyl 2-(3-Amino-2-oxopyrrolidin-1-yl)acetate (128). To a solution of 114 mg (0.33 mmol) of 127 in 5 mL of anhydrous DCM at 0° C. was added 1.0 mL of TFA with stirring. After stirring at 0° C. for 1 h, the reaction mixture was directly concentrated to dryness in vacuo as a crude oil. The resulting oil was co-evaporated with 5 mL of toluene and 5 mL of DCM respectively to afford a trifluoroacetate of 128 as a colorless oil: yield 114 mg (100%); silica gel TLC

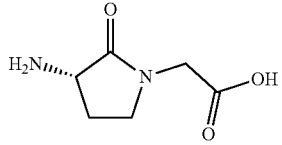 [SMILES: N[C@H]1CCN(CC(=O)O)C1=O]

(S)-2-(3-Amino-2-oxopyrrolidin-1-yl)acetic Acid (123). A solution of 114 mg (0.33 mmol) of 128 in 5 mL of 95% EtOH was introduced into a bottle which was purged with N$_2$ in advance. 20.0 mg of 10% Pd/C was then added. The bottle was filled with H$_2$ through a balloon and stirred at room temperature for 1 h. The catalyst was filtered off on celite and washed several times with EtOH. The solvent was removed under vacuum to give a trifluoroacetate of 123 as a colorless solid: yield 84.0 mg (100%); silica gel TLC R$_f$0.22 (10:1 DCM-MeOH); $^1$H NMR (CD$_3$OD) δ 2.05-2.19 (m, 1H), 2.55-2.67 (m, 1H), 3.47-3.68 (m, 2H), 4.03-4.22 (m, 3H) and 5.04 (br s, 2H); $^{13}$C NMR (CD$_3$OD) δ 23.9, 43.7, 44.54, 50.4, 169.9 and 170.0.

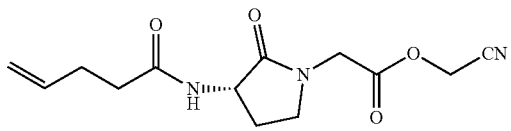 [SMILES: C=CCCC(=O)N[C@H]1CCN(CC(=O)OCC#N)C1=O]

(S)-Cyanomethyl 2-(2-Oxo-3-(pent-4-enamido)pyrrolidin-1-yl)acetate (130). To a solution of 84.0 mg (0.33 mmol) of 123 in 3 mL of anhydrous DMF was added 135 μL (106 mg, 0.82 mmol) of DIPEA with stirring, followed by 97.0 mg (0.49 mmol) of 4-pentenoyloxysuccinimide at room temperature and the reaction mixture was stirred at room temperature for overnight. The mixture was diluted with 15 mL of EtOAc and 15 mL of water, and then the aqueous phase was extracted with another 15 mL portion of EtOAc. The aqueous phase was directly concentrated to dryness in vacuo as oil. The resulting oil was co-evaporated with 5 mL of toluene and 5 mL of DCM respectively to afford 129 as a colorless oil: yield 52.0 mg (65%); silica gel TLC R$_f$0.75 (5:1:1 DCM-MeOH-AcOH). This material was taken forward without further purification. To a solution of 52.0 mg (0.21 mmol) of 129 in 4 mL of anhydrous DMF was added 136 μL (99.0 mg, 0.98 mmol) of Et$_3$N with stirring, followed by 23.0 μL (27.2 mg, 0.36 mmol) of chloroacetonitrile at room temperature and the reaction mixture was stirred at room temperature for overnight. The mixture was diluted with 15 mL of water, and then the aqueous phase was extracted with three 15 mL-portions of EtOAc. The combined organic extract was dried over Na$_2$SO$_4$, filtered, and concentrated under reduced pressure. The residue was purified by chromatography on a silica gel column (10×2 cm). Elution with 80:1 DCM-MeOH afforded 130 as a colorless oil: yield 6.00 mg (7% over two steps); silica gel TLC R$_f$0.25 (40:1 DCM-MeOH); $^1$H NMR (CDCl$_3$) δ 1.52-1.75 (m, 2H), 1.80-2.00 (m, 1H), 2.24-2.45 (m, 4H), 2.71-2.84 (m, 1H), 3.32-3.44 (m, 1H), 3.45-3.56 (m, 1H), 4.02-4.15 (m, 2H), 4.42 (dd, 1H, J=14.1 and 9.5 Hz), 5.03 (dd, 2H, J=24.9 and 13.6 Hz), 5.81 (dq, 1H, J=11.0 and 6.2 Hz) and 6.09 (br s, 1H); $^{13}$C NMR (CDCl$_3$) δ 28.3, 29.4, 35.4, 44.4, 44.9, 48.9, 51.3, 52.4, 115.7, 136.8, 168.6, 172.9 and 173.0.

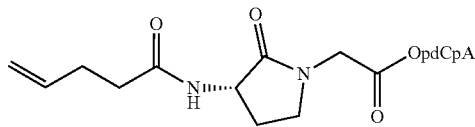

(S)-2-(2-Oxo-3-(pent-4-enamido)pyrrolidin-1-yl)acetyl-pdCpA (131). A solution containing 6.00 mg (21.5 μmol) of 130 and 7.00 mg (5.13 μmol) of pdCpA tetrabutylammonium salt in 100 μL of 9:1 anhydrous DMF-Et$_3$N was sonicated at room temperature for 12 h. After which time, the reaction mixture was purified by C$_{18}$ reversed phase HPLC (250×10 mm) using a gradient of 1%-+65% acetonitrile in 50 mM ammonium acetate, pH 4.5, over a period of 45 min. The fractions eluting at around 14.2 min were collected, combined and lyophilized to afford 131 as a colorless solid by lyophilization: yield 0.40 mg (9%); mass spectrum (ESI), m/z 857.2028 (M−H)$^-$ (C$_{30}$H$_{39}$N$_{10}$O$_{16}$P$_2$ requires m/z 857.2026).

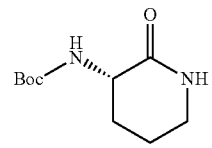

(S)-tert-Butyl (2-Oxopiperidin-3-yl)carbamate (133). To a solution of 0.64 g (2.75 mmol) of BOC-L-ORN-OH in 275 mL of DMF at a 10 mM concentration were added 1.22 g (2.75 mmol) of BOP and 1.16 g (20.0 mmol) of sodium bicarbonate. After 12 h stirring at room temperature, the mixture was concentrated to a small volume (around 5 mL) under reduced pressure. The concentrated mixture was diluted with water and saturated sodium bicarbonate solution (1:1, 100 mL) and extracted with three 100-mL portions of EtOAc. The combined organic extracts were washed with 300 mL of water and 300 mL of brine, dried over Na$_2$SO$_4$, filtered, and concentrated under reduced pressure to afford a 133 as a colorless solid: yield 0.37 g (62%); Silica gel TLC R$_f$0.55 (10:1 DCM-MeOH); $^1$H NMR (CDCl$_3$) δ 1.32 (s, 9H), 1.45-1.64 (m, 1H), 1.65-1.84 (m, 2H), 2.10-2.30 (m, 1H), 3.15-3.25 (m, 2H), 3.79-4.05 (m, 1H), 5.62 (br s, 1H) and 6.99 (br s, 1H); $^{13}$C NMR (CDCl$_3$) δ 27.7, 28.2, 36.56, 36.61, 41.5, 51.0, 79.5, 156.0 and 172.3.

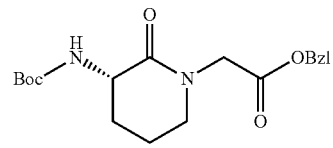

(S)-Benzyl 2-(3-((tert-Butoxycarbonyl)amino)-2-oxopiperidin-1-yl)acetate (134). A solution of 0.36 g of 133 (1.68 mmol) in 5 mL of anhydrous THF was added to a suspension of 134 mg (3.36 mmol) of sodium hydride (60% dispersion in mineral oil) in 10 mL of anhydrous THF. The reaction was stirred at room temperature for 15 min, and 280 µL (403 mg, 1.76 mmol) of benzyl bromoacetate was added. After 5 h stirring at room temperature, 30 mL of EtOAc was added, followed by 20 mL of water. The organic phase was washed with 20 mL of brine, dried over Na₂SO₄, filtered and concentrated under reduced pressure to afford an oily residue. The residue was purified by chromatography on a silica gel column (10×2 cm). Elution with 3:1 hexanes-EtOAc afforded 134 as colorless oil: yield 353 mg (58%); Silica gel TLC R$_f$0.52 (3:1 hexanes-EtOAc); $^1$H NMR (CDCl₃) δ 1.35 (s, 9H), 1.47-1.63 (m, 1H), 1.75-1.85 (m, 2H), 2.26-2.38 (m, 1H), 3.17-3.34 (m, 2H), 4.01 (m AB system, 2H), 3.93-4.07 (m, 1H), 4.99-5.11 (m, 2H), 5.43 (br s, 1H) and 7.16-7.31 (m, 5H); $^{13}$C NMR (CDCl₃) δ 20.8, 27.8, 28.3, 48.7, 48.9, 51.6, 66.8, 79.3, 128.2, 128.3, 128.5, 135.3, 155.8, 168.6 and 170.3.

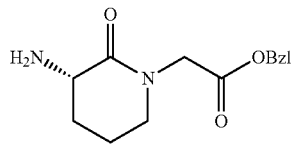

(S)-Benzyl 2-(3-Amino-2-oxopiperidin-1-yl)acetate (135). To a solution of 180 mg (0.50 mmol) of 134 in 4 mL of anhydrous DCM at 0° C. was added 1.0 mL of TFA with stirring. After stirring at 0° C. for 1 h, the reaction mixture was directly concentrated to dryness in vacuo as oil. The resulting oil was co-evaporated with 5 mL of toluene and 5 mL of DCM respectively to afford a trifluoroacetate of 135 as colorless oil: 180 mg (100%); silica gel TLC R$_f$0.52 (10:1 DCM-MeOH); $^1$H NMR (CDCl₃) δ 1.73-2.12 (m, 3H), 2.25-2.45 (m, 1H), 3.15-3.45 (m, 2H), 3.86-3.99 (m, 1H), 4.09 (dd, 2H, J=43.0 and 17.3 Hz), 5.12 (s, 2H), 7.25-7.47 (m, 5H) and 8.20 (br s, 2H); $^{13}$C NMR (CDCl₃) δ 20.3, 21.4, 24.8, 48.8, 50.5, 67.3, 128.3, 128.5, 128.6, 167.5 and 168.4.

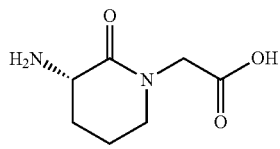

(S)-2-(3-Amino-2-oxopiperidin-1-yl)acetic Acid (124). A solution of 180 mg (0.50 mmol) of 135 in 5 mL of 95% EtOH was introduced into a bottle which was purged with N₂ in advance. 20.0 mg of 10% Pd/C was then added. The bottle was filled with H₂ through a balloon and stirred at room temperature for 1 h. The catalyst was filtered off on celite and washed several times with EtOH. The solvent was removed under vacuum to give a trifluoroacetate of 124 as a viscous oil: yield 135 mg (100%); silica gel TLC R$_f$ 0.42 (10:1 DCM-MeOH); $^1$H NMR (CD₃OD) δ 1.79-2.14 (m, 3H), 2.23-2.38 (m, 11H), 3.35-3.55 (m, 2H), 3.93 (dd, 11H, J=11.8, 5.8 Hz), 4.10 (dd, 2H, J=72.9, 17.5 Hz) and 4.96 (br s, 2H); $^{13}$C NMR (CD₃OD) δ 20.1, 25.1, 48.1, 48.5, 49.9, 166.7 and 170.5.

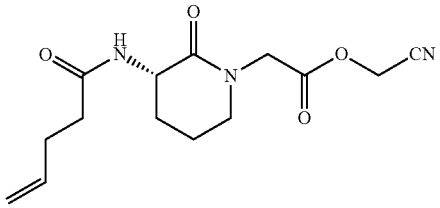 [SMILES: C=CCCC(=O)N[C@H]1CCCN(CC(=O)OCC#N)C1=O]

(S)-Cyanomethyl 2-(2-oxo-3-(pent-4-enamido)piperidin-1-yl)acetate (137). To a solution of 135 mg (0.50 mmol) of 124 in 4 mL of anhydrous DMF was added 207 µL (162 mg, 1.25 mmol) of DIPEA with stirring, followed by 147 mg (0.75 mmol) of 4-pentenoyloxysuccinimide at room temperature and the reaction mixture was stirred at room temperature for overnight. The mixture was diluted with 15 mL of EtOAc and 15 mL of water, and then the aqueous phase was extracted with another 15 mL of EtOAc. The aqueous phase was directly concentrated to dryness in vacuo. The resulting oil was co-evaporated with 5 mL of toluene and 5 mL of DCM respectively to afford 136 as a colorless oil: yield 89.0 mg (70%); silica gel TLC R$_f$0.45 (10:1:1 DCM-MeOH-AcOH). This material was taken forward without further purification. To a solution of 89.0 mg (0.35 mmol) of 136 in 4 mL of anhydrous DMF was added 230 µL (168 mg, 1.66 mmol) of Et₃N with stirring, followed by 39.0 µL (46.0 mg, 0.61 mmol) of chloroacetonitrile at room temperature and the reaction mixture was stirred at room temperature overnight. The mixture was diluted with 15 mL of water, and then the aqueous phase was extracted with three 15-mL portions of EtOAc. The combined organic extract was dried over Na₂SO₄, filtered, and concentrated under reduced pressure. The residue was purified by chromatography on a silica gel column (10×2 cm). Elution with 80:1 DCM-MeOH afforded 137 as a colorless oil: yield 33.0 mg (23% over two steps); silica gel TLC R$_f$ 0.45 (60:3:2 DCM-MeOH-AcOH); $^1$H NMR (CDCl₃) δ 1.50-1.68 (m, 1H), 1.85-2.10 (m, 2H), 2.25-2.43 (m, 4H), 2.48-2.62 (m, 1H), 3.29-3.55 (m, 2H), 3.93 (d, 1H, J=17.5 Hz), 4.27-4.41 (m, 2H), 4.77 (q, 2H, J=15.7 Hz), 4.92-5.12 (m, 2H), 5.80 (dq, 1H, J=10.7 and 6.3 Hz) and 6.42 (br s, 1H); $^{13}$C NMR (CDCl₃) (20.9, 27.3, 29.4, 35.7, 48.7, 48.9, 49.0, 50.9, 113.8, 115.5, 136.9, 167.5, 170.7 and 172.5.

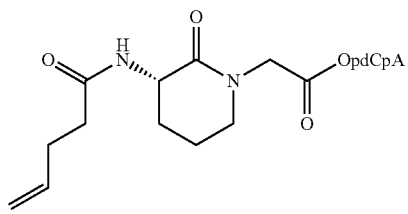

(S)-2-(2-Oxo-3-(pent-4-enamido)piperidin-1-yl)acetyl-pdCpA (138). A solution containing 8.00 mg (27.0 µmol) of 137 and 6.00 mg (4.40 µmol) of pdCpA tetrabutylammonium salt in 100 µL of 9:1 anhydrous DMF-Et₃N was sonicated at room temperature for 12 h. After which time, the reaction mixture was purified by C₁₈ reversed phase HPLC (250×10 mm) using a gradient of 1%-65% acetonitrile in 50 mM ammonium acetate, pH 4.5, over a period of 45 min. The fractions eluting at around 15.1 min were collected, combined and lyophilized to afford 138 as a colorless solid by lyophilization: yield 0.7 mg (18%); mass spectrum (ESI), m/z 871.2188 (M−H)⁻ (C₃₁H₄₁N₁₀O₁₆P₂ requires m/z 871.2183).

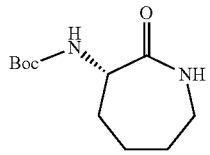 [SMILES: CC(C)(C)OC(=O)N[C@H]1CCCCNC1=O]

(S)-tert-Butyl (2-Oxoazepan-3-yl)carbamate (140). To a solution of 0.68 g (2.75 mmol) of BOC-L-LYS-OH in 275 mL of DMF at a 10 mM concentration were added 1.22 g (2.75 mmol) of BOP and 1.16 g (20.0 mmol) of sodium bicarbonate. After 12 h stirring at room temperature, the mixture was concentrated to a small volume (around 5 mL) under reduced pressure. The concentrated mixture was diluted with water and saturated sodium bicarbonate solution (1:1, 100 mL) and extracted with three 100-mL portions of EtOAc. The combined organic extracts were washed with 200 mL of water and 200 mL of brine, dried over Na₂SO₄, filtered, and concentrated under reduced pressure to afford a residue that crystallized upon trituration in 100 mL of ether and filtered to afford 140 as a colorless solid: yield 398 mg (63%); mp 140-141° C.; silica gel TLC R$_f$0.75 (10:1 DCM-MeOH); ¹H NMR (CDCl₃) δ 1.40 (s with overlap, 9H), 1.29-1.58 (m with overlap, 2H), 1.63-1.88 (m, 2H), 1.87-2.12 (m, 2H), 3.16-3.28 (m, 2H), 4.20-4.32 (m, 1H), 5.88 (br s, 1H) and 6.68 (br s, 1H); ¹³C NMR (CDCl₃) δ 28.1, 28.4, 28.8, 32.2, 42.1, 53.2, 79.4, 155.1 and 175.9.

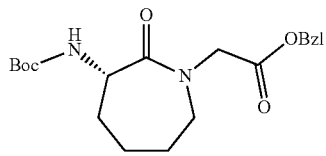

(S)-Benzyl 2-(3-((tert-Butoxycarbonyl)amino)-2-oxoazepan-1-yl)acetate (141). A solution of 417 mg (1.83 mmol) of 140 in 5 mL of anhydrous THF was added to a suspension of 147 mg (3.65 mmol) of sodium hydride (60% dispersion in mineral oil) in 10 mL of anhydrous THF. The reaction was stirred at room temperature for 15 min, and 304 μL (440 mg, 1.92 mmol) of benzyl bromoacetate was added. After 5 h stirring at room temperature, 30 mL of EtOAc was added, followed by 20 mL of water. The organic phase was washed with 20 mL of brine, dried over Na₂SO₄, filtered and concentrated under reduced pressure. The residue was purified by chromatography on a silica gel column (10×2 cm). Elution with 6:1 hexanes-EtOAc afforded 141 as a colorless oil: yield 497.0 mg (72%); silica gel TLC R$_f$0.72 (1:1 hexanes-EtOAc); ¹H NMR (CDCl₃) δ 1.34 (s, 9H), 1.42-1.55 (m, 2H), 1.57-1.74 (m, 2H), 1.73-2.01 (m, 2H), 2.98-3.14 (m, 1H), 3.42-3.60 (m, 1H), 4.09 (q, 2H, J=17.4 Hz), 4.24-4.40 (m, 1H), 4.95-5.13 (m, 2H), 5.85-5.90 (m, 2H) and 7.15-7.34 (m, 5H); ¹³C NMR (CDCl₃) δ 26.9, 27.8, 28.3, 32.2, 50.5, 50.8, 53.3, 66.8, 79.1, 128.2, 128.3, 128.5, 135.3, 155.0, 168.9 and 173.5.

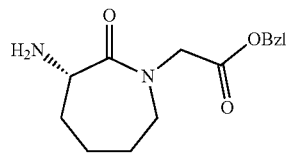

(S)-Benzyl 2-(3-Amino-2-oxoazepan-1-yl)acetate (142). To a solution of 160 mg (0.43 mmol) of 141 in 6 mL of anhydrous DCM at 0° C. was added 1.0 mL of TFA with stirring. After stirring at 0° C. for 1 h, the reaction mixture was directly concentrated to dryness in vacuo as oil. The resulting oil was co-evaporated with 5 mL of toluene and 5 mL of DCM respectively to afford a trifluoroacetate of 142 as a colorless oil: yield 160 mg (100%); silica gel TLC R$_f$0.18 (10:1 DCM-MeOH); ¹H NMR (CDCl₃) δ 1.47-1.82 (m, 4H), 1.85-1.96 (m, 1H), 2.05-2.10 (m, 1H), 3.03-3.19 (m, 1H), 3.50-3.70 (m, 1H), 4.13 (m AB system, 2H), 4.29-4.40 (m, 1H), 5.10 (s, 2H), 7.27-7.37 (m, 5H) and 8.10-8.30 (br s, 2H); ¹³C NMR (CDCl₃) δ 26.3, 26.9, 28.3, 50.5, 51.1, 53.6, 67.3, 128.4, 128.5, 128.6, 135.1, 168.8 and 171.4.

(S)-2-(3-Amino-2-oxoazepan-1-yl)acetic Acid (125). A solution of 160 mg (0.43 mmol) of 142 in 5 mL of 95% EtOH was introduced into a bottle which was purged with N₂ in advance. 20.0 mg of 10% Pd/C was then added. The bottle was filled with H₂ through a balloon and stirred at room temperature for 1 h. The catalyst was filtered off on celite and washed several times with EtOH. The solvent was removed under vacuum to give a trifluoroacetate of 125 as a colorless solid: yield 122 mg (100%); mp 182-184° C.; silica gel TLC R$_f$0.05 (10:1 DCM-MeOH); ¹H NMR (CD₃OD) δ 1.62-1.86 (m, 4H), 1.88-2.10 (m, 2H), 3.36 (dd, 1H, J=15.6 and 4.4 Hz), 3.62-3.73 (m, 1H), 4.18 (s, 2H), 4.26-4.34 (m, 1H) and 4.87 (br s, 2H); ¹³C NMR (CD₃OD) δ 26.3, 26.9, 28.5, 49.8, 50.1, 53.0, 170.6 and 170.9.

(S)-Cyanomethyl 2-(2-Oxo-3-(pent-4-enamido)azepan-1-yl)acetate (144). To a solution of 61.0 mg (0.22 mmol) of 125 in 3 mL of anhydrous DMF was added 90.0 μL (70.0 mg, 0.55 mmol) of DIPEA with stirring, followed by 64.0 mg (0.32 mmol) of 4-pentenoyloxysuccinimide at room temperature and the reaction mixture was stirred at room temperature for overnight. The mixture was diluted with 15 mL of EtOAc and 15 mL of water, and then the aqueous phase was extracted with another 15 mL portion of EtOAc. The aqueous phase was directly concentrated to dryness in vacuo. The resulting oil was co-evaporated with 5 mL of toluene and 5 mL of DCM respectively to afford 143 as a colorless oil: yield 50.0 mg (85%); silica gel TLC $R_f$ 0.10 (60:3:2 DCM-MeOH-AcOH). This material was taken forward without further purification. To a solution of 50.0 mg (0.19 mmol) of 143) in 3 mL of anhydrous DMF was added 90.0 μL (66.0 mg, 0.65 mmol) of $Et_3N$ with stirring, followed by 25.0 μL (30.0 mg, 0.40 mmol) of chloroacetonitrile at room temperature and the reaction mixture was stirred at room temperature overnight. The mixture was diluted with 10 mL of water, and then the aqueous phase was extracted with three 10-mL portions of EtOAc. The combined organic extract was dried over $Na_2SO_4$, filtered, and concentrated under reduced pressure to afford a residue. The residue was purified by chromatography on a silica gel column (10×2 cm). Elution with 50:1 DCM-MeOH afforded 144 as a colorless oil: yield 14.0 mg (21% over two steps); silica gel TLC $R_f$ 0.45 (40:1 DCM-MeOH); $^1H$ NMR ($CDCl_3$) δ 1.40-1.70 (m, 2H), 1.75-2.10 (m, 4H), 2.22-2.45 (m, 4H), 3.15-3.30 (m, 1H), 3.64-3.80 (m, 1H), 4.24 (dd, 2H, J=41.4 and 17.6 Hz), 4.64-4.71 (m, 1H), 4.75-4.81 (m, 2H), 4.95-5.12 (m, 2H), 5.73-5.87 (m, 1H) and 6.85 (br s, 1H); $^{13}C$ NMR ($CDCl_3$) a 27.0, 27.7, 29.4, 31.8, 35.7, 48.8, 50.6, 51.0, 52.3, 113.8, 115.5, 136.8, 167.7, 171.3 and 173.9.

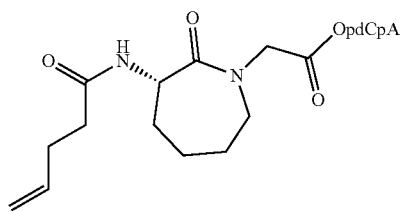

144

(S)-2-(2-Oxo-3-(pent-4-enamido)azepan-1-yl)acetyl-pdCpA (145). A solution containing 14.0 mg (45.5 μmol) of 144 and 15.5 mg (11.4 μmol) of pdCpA tetrabutylammonium salt in 100 μL of 9:1 anhydrous DMF-$Et_3N$ was sonicated at room temperature for 12 h. After which time, the reaction mixture was purified by $C_{18}$ reversed phase HPLC (250×10 mm) using a gradient of 1%-+65% acetonitrile in 50 mM ammonium acetate, pH 4.5, over a period of 45 min. The fractions eluting at around 16.8 min were collected, combined and lyophilized to afford 145 as a coloeless solid by lyophilization: yield 3.8 mg (38%); mass spectrum (ESI), m/z 885.2342 (M–H)$^-$ ($C_{32}H_{43}N_{10}O_{16}P_2$ requires m/z 885.2339).

Figure 14:
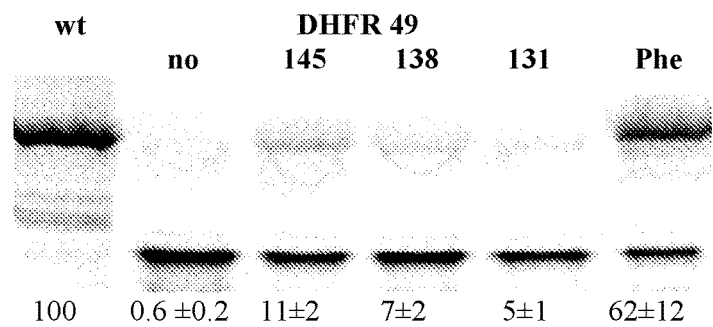
FIG. 14. Analysis of samples of DHFR after in vitro translation from wild-type (wt) and modified (DHFR49) genes in the absence (no) and in the presence of compounds 131, 138 and 145, coupled with tRNA$_{CUA}$, and Phe-tRNA$_{CUA}$ (Phe), by SDS-polyacrylamide gel electrophoresis.

Incorporation of cyclic peptidomimetics 131, 138 and 145 in (DHFR using modified ribosomes. Three cyclic peptidomimetics were incorporated into position 49 of DHFR (pETDH49 plasmid). An S-30 system from clones 010328R4, which belong to group 1 (Table 1), was prepared. The suppression efficiency was expressed relative to the DHFR synthesis from wild-type gene (pETDHwt plasmid). As a negative and positive control, full-size DHFR synthesis in the presence of nonacylated tRNA$_{CUA}$ and tRNA$_{CUA}$ acylated with phenylalanine were measured (FIG. 14). The best level of full-length DHFR synthesis (11-13% relative to wild-type) was demonstrated for cyclic peptidomimetic 145. The other two compounds gave about 1.5-2 times lower suppression efficiency (7-9 and 5-6%).

Figure 15:
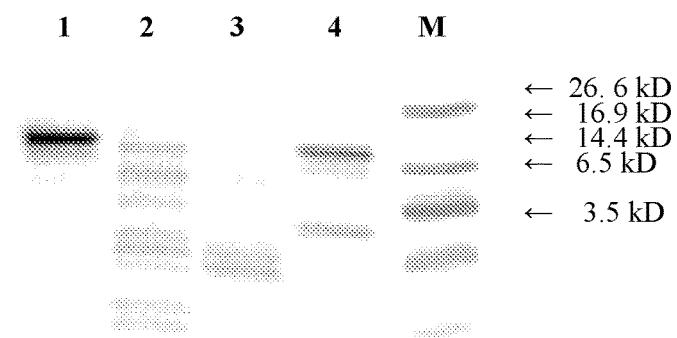
FIG. 15. GluC digestion of DHFR samples. Lanes 1 and 4—non digested DHFRwt samples before and after incubation at 37° C.; lane 2—GluC digested DHFRwt sample; lane 3—GluC digested modified DHFR (cyclic peptidomimetic 145 in position 49). M-markers of molecular weight.

The proteolytic stability of DHFR with cyclic peptidomimetic 145 in position 49 was studied. Two samples of DHFR (wt and mutant) were prepared during in vitro translation and purified by Ni-NTA chromatography followed by a desalting/concentration procedure using an Amicon Ultra 10K filtration device. Bothe samples were incubated in the presence of GluC endoproteinase and analyzed by Tris-Tricine gel electrophoresis (FIG. 15). It was found that the DHFR sample with the cyclic peptidomimetic in position 49 after digestion has demonstrated only one fragment with molecular weight around 7 kD, i.e. that corresponding to the expected fragment (18-80 amino acids). No small fragments (~3-4 kD) were found. A large excess of enzyme was used; that may have activate non-specific digestion of the proteins. Therefore, the wild-type control contained several bands. The absence of these bands in the modified protein represents additional evidence of its higher stability.

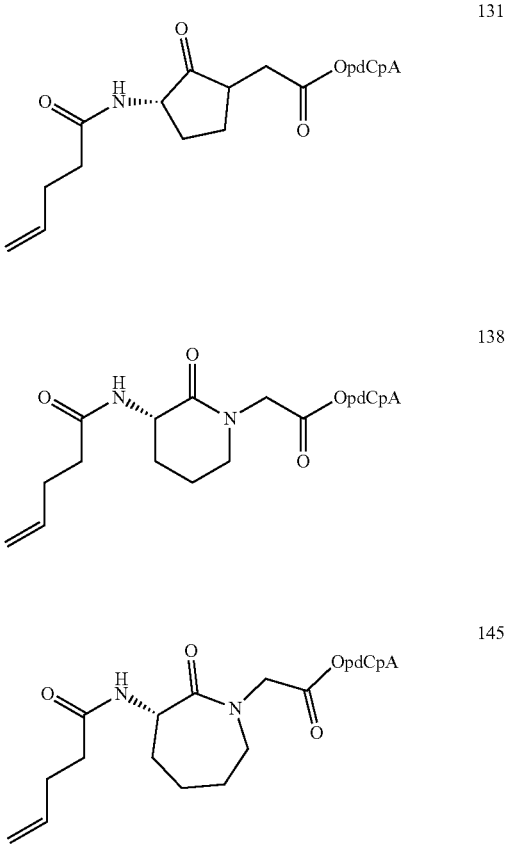

In view of the methods and materials described herein, one of ordinary skill in the art will readily appreciate that the sequence modifications in 23S rRNA are not limited to those found in Tables 1-3 below, but may encompass any combinations and permutations given in Table 5.

TABLE 1

Selection Data and 23S rRNA Sequence Modifications in the PTC for the Clones used for S-30 preparations.

| Clone group | Clone name | Sequence in 23S rRNA of modified ribosomes Region 1 (2057-2063) | Region 2 (2502-2507) | Inhibition by Puromycin Derivative 1 (%) | Erythromycin (MIC, µg/mL) |
|---|---|---|---|---|---|
| 1 | 010309R3 | UGCGUGG | ACGAAG | 63.2 | 12.5-6.25 |
|   | 010326R6 | UGCGUGG | ACGAAG | 50.4 | 12.5-6.25 |
|   | 010328R4 | UGCGUGG | ACGAAG | 61 | 6.25-3.12 |
|   | 010322 | UGCGUGG | ACGAAG | 77 | 12.5-6.25 |
| 2 | 010310R4 | UGCGUGG | CGCACG | 52.9 | 12.5-6.25 |
| 3 | 010326R5 | UGCGUGG | CUAUGU | 50.4 | 12.5-6.25 |
| 4 | 010310R1 | UGCGUGG | CGCAAU | 52.9 | 12.5-6.25 |
| 5 | 010328R2 | UGCGUGG | CUACAG | 77 | 12.5-6.25 |
|   | 010326R1 | UGCGUGG | CUACAG | 50.4 | 12.5-6.25 |
| 6 | 040322 | AGCGUGA | CUGCGU | 54 | 6.25-3.12 |
| 7 | 040329 | AGCGUGA | UGGCAG | 54 | 6.25-3.12 |
| 8 | 040338 | AGCGUGA | AUCAGG | 56 | 6.25-3.12 |
| 9 | 080337 | AGUGAGA | AUCCGA | 51 | 25-12.5 |
|   | Wild-type | GAAAGAC | GAUGUC | <1 | 3.12-1.56 |

TABLE 2

Sequence in Region 2502-2507 of Clones Having Same Sequence in Region 2057-2063 (UGCGUGG).

| Clones | Nucleotide in position |  |  |  |  |  |
|---|---|---|---|---|---|---|
|  | 2502 | 2503 | 2504 | 2505 | 2506 | 2507 |
| 010309R3 | A | C | G | A | A | G |
| 010326R6 | A | C | G | A | A | G |
| 010328R4 | A | C | G | A | A | G |
| 010322 | A | C | G | A | A | G |
| 010310R4 | C | G | C | A | C | G |
| 010326R5 | C | U | A | U | G | U |
| 010310R1 | C | G | C | A | A | U |
| 010328R2 | C | U | A | C | A | G |
| 010326R1 | C | U | A | C | A | G |

TABLE 3

Incorporation of Dipeptides 2 and 3 into Position 10 of E. coli DHFR by the Use of S-30 Systems Having Different Modified Ribosomes.

| Clone group | Sequence in 23S rRNA of modified ribosomes Region 1 (2057-2063) | Region 2 (2502-2507) | Suppression efficiency in different S-30 systems, having modified ribosomes (%)[a] Amino acids −[b] | 2 | 3 |
|---|---|---|---|---|---|
| 1 | UGCGUGG | ACGAAG | 0.8 ± 0.2[c] | 8.4 ± 1.6 | 13.9 ± 1.7 |
| 2 | UGCGUGG | CGCACG | 1.6 ± 0.9 | 9.5 ± 0.5 | 10.6 ± 0.5 |
| 3 | UGCGUGG | CUAUGU | 1.1 ± 0.5 | 8.6 ± 1.5 | 12.7 ± 2.5 |
| 4 | UGCGUGG | CGCAAU | 1.5 ± 0.7 | 3.1 ± 0.2 | N.T. |
| 5 | UGCGUGG | CUACAG | 0.5 ± 0.1 | 4.5 ± 0.7 | N.T. |
| 6 | AGCGUGA | CUGCUU | 0.1[d] | 3.5 | N.T. |

TABLE 3-continued

Incorporation of Dipeptides 2 and 3 into Position 10 of E. coli DHFR by the Use of S-30 Systems Having Different Modified Ribosomes.

| Clone group | Sequence in 23S rRNA of modified ribosomes | | Suppression efficiency in different S-30 systems, having modified ribosomes (%)[a] Amino acids | | |
|---|---|---|---|---|---|
| | Region 1 (2057-2063) | Region 2 (2502-2507) | -[b] | 2 | 3 |
| 7 | AGCGUGA | UGGCAG | 1.1 ± 0.1 | 2.1 ± 0.1 | N.T. |
| 8 | AGCGUGA | AUCAGG | 0.9 | 2.2 | N.T. |
| 9 | AGUGAGA | AUCCGA | 1.4 ± 0.6 | 9.6 ± 2.0 | 13.3 ± 2.5 |

[a] Amount of the wild-type DHFR translated using S-30 systems having corresponding modified ribosome was arbitrarily assigned a value of 100. The suppression efficiency for each amino acid was calculated in relative to the amount of wild-type DHFR.
[b] Non-specific read through of the amber stop codon in relative to the amount of wild-type DHFR synthesis.
[c] Each number represents the average of three independent experiments ± S.D.
[d] Single experiment was performed.
N.T = not tested

TABLE 4

Incorporation of Dipeptidomimetics 5, 6, 8, 9 and 10 into Position 10 of E. coli DHFR by the Use of S-30 Systems Having Different Modified Ribosomes.

| Clone group | Suppression efficiency in different S-30 systems, having modified ribosomes (%)[a] Amino acids | | | | | |
|---|---|---|---|---|---|---|
| | -[b] | 5 | 6 | 8 | 9 | 10 |
| 1 | 0.8 ± 0.2[c] | 11.5 ± 0.7 | 10.2 ± 1.7 | 9.1[d] | 11.7 ± 1.4 | 11.9 |
| 9 | 1.4 ± 0.6 | 10.7 ± 1.6 | 9.8 ± 2.1 | N.T. | N.T. | N.T. |

[a] Amount of the wild-type DHFR translated using S-30 systems having corresponding modified ribosome was arbitrarily assigned a value of 100. The suppression efficiency for each dipeptidomimetic was calculated in relative to the amount of wild-type DHFR.
[b] Non-specific read through of the amber stop codon in relative to the amount of wild-type DHFR synthesis.
[c] Each number represents the average of three independent experiments ± S.D.
[d] Single experiment was performed.
N.T = not tested

TABLE 5

Possible nucleotide(s) present at a given position of modified 23S rRNA.

| Region 1 | | | | | | | | |
|---|---|---|---|---|---|---|---|---|
| 2056 | 2057 | 2058 | 2059 | 2060 | 2061 | 2062 | 2063 | 2064 |
| G | U | G | C | G | U | G | G | C |
| | A | | U | | A | | A | |

| Region 2 | | | | | | | |
|---|---|---|---|---|---|---|---|
| 2501 | 2502 | 2503 | 2504 | 2505 | 2506 | 2507 | 2508 |
| C | U | C | G | U | G | U | G |
| | A | U | A | A | A | A | |
| | C | G | C | C | C | G | |

TABLE 6
Examples of non-naturally occurring dipeptidomimetics added to proteins to yield modified proteins
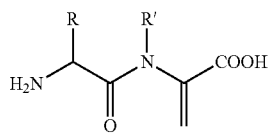
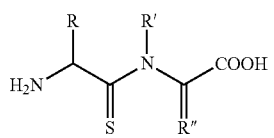
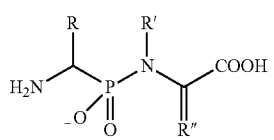
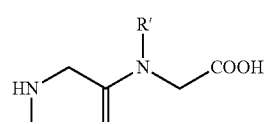
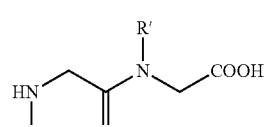
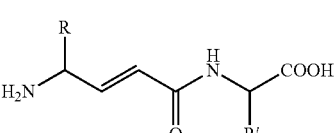
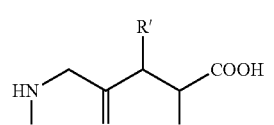
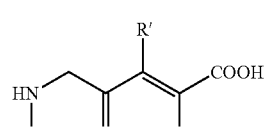
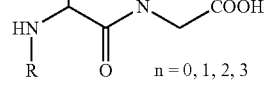
n = 0, 1, 2, 3
Scheme 1: Synthesis of dipeptidyl-puromycin aminonucleoside 1
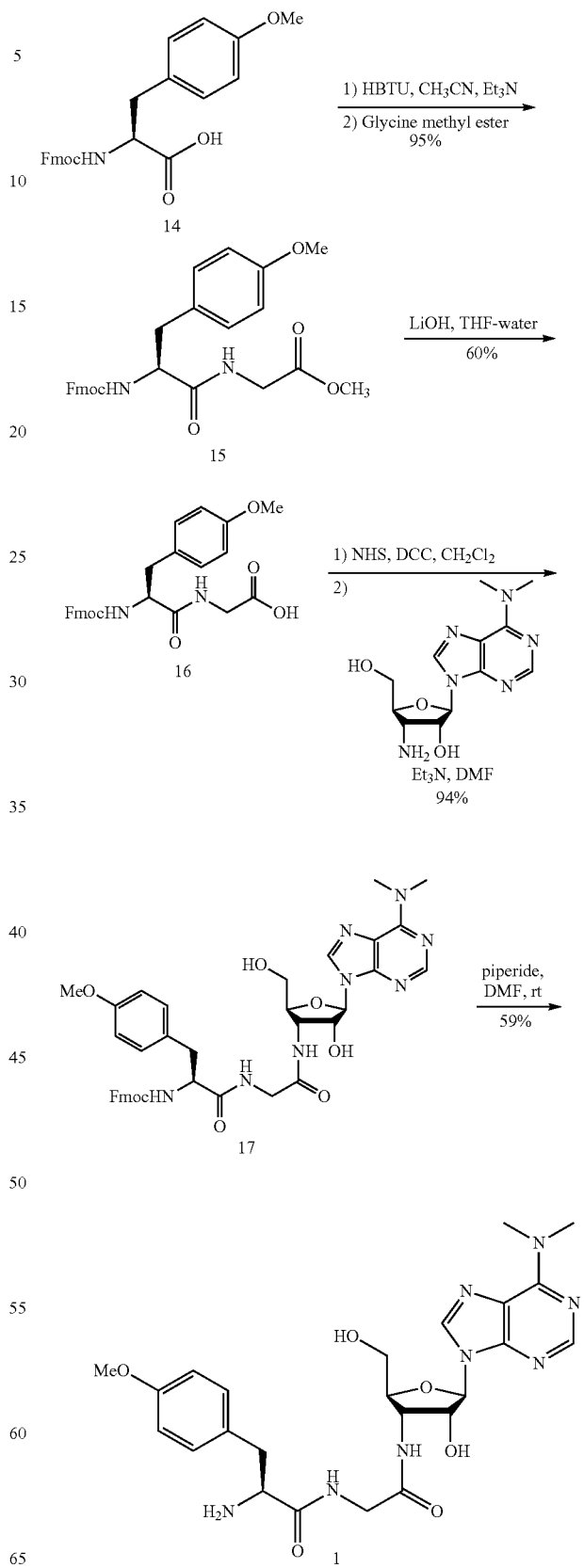

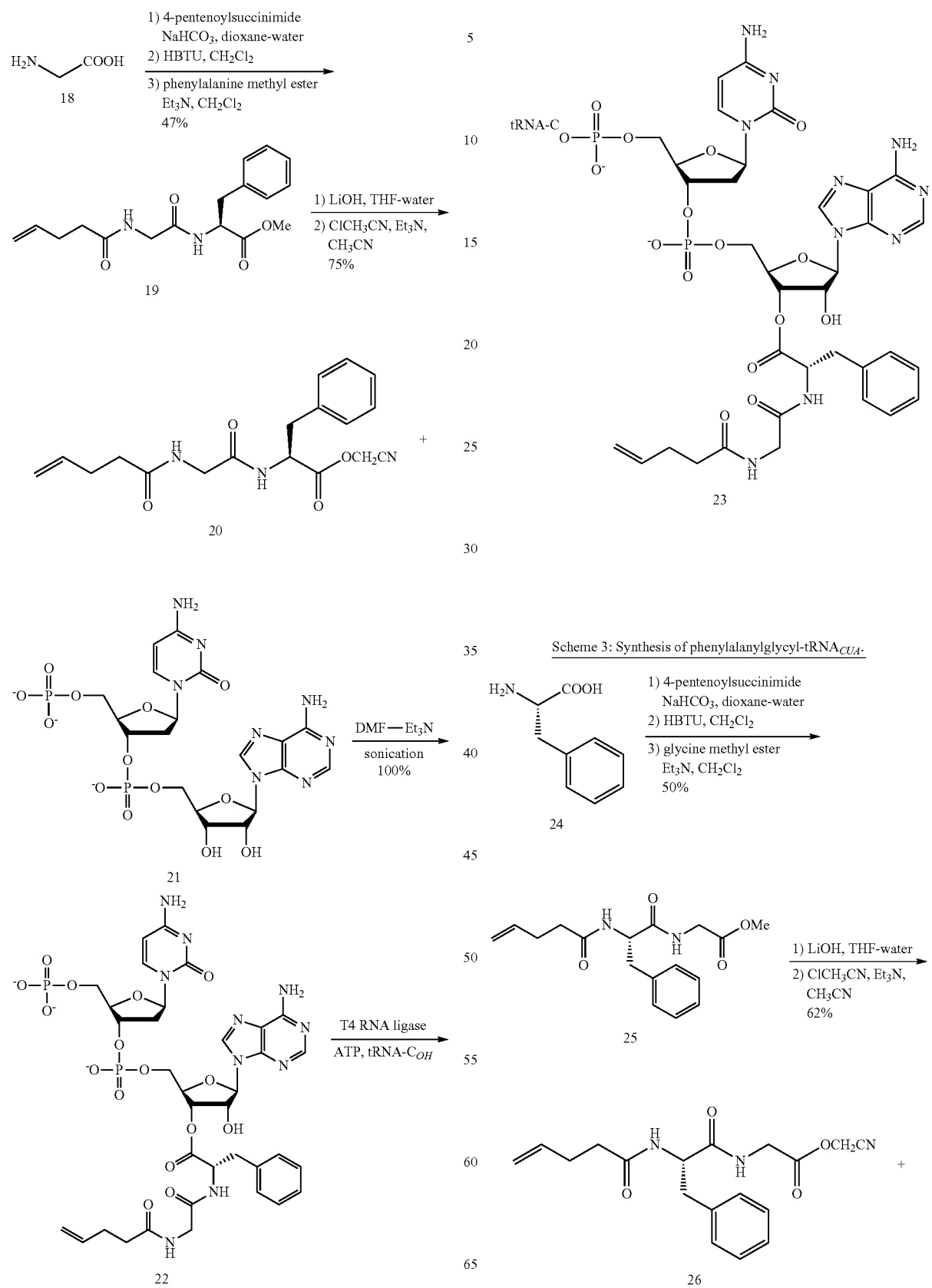

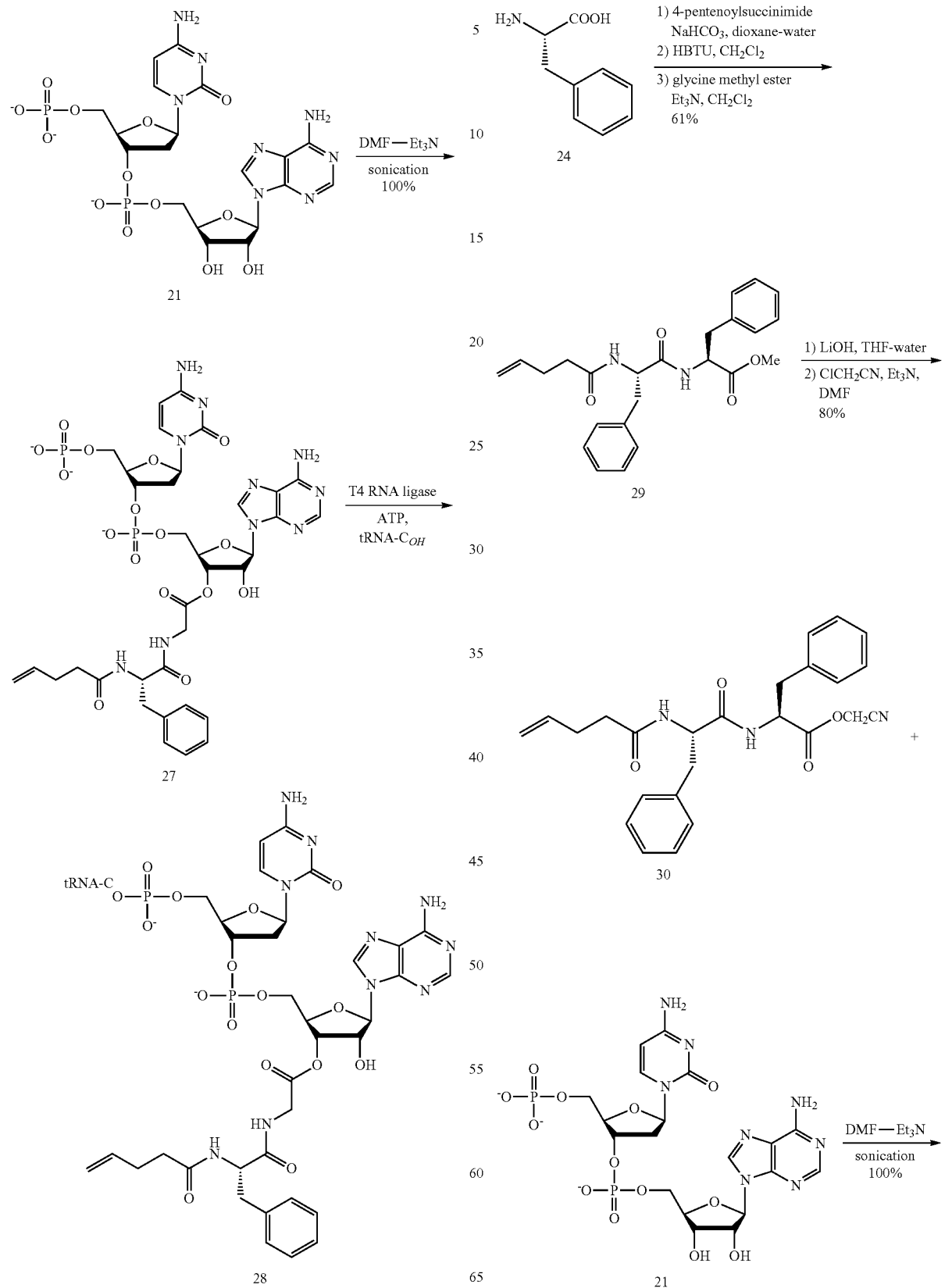

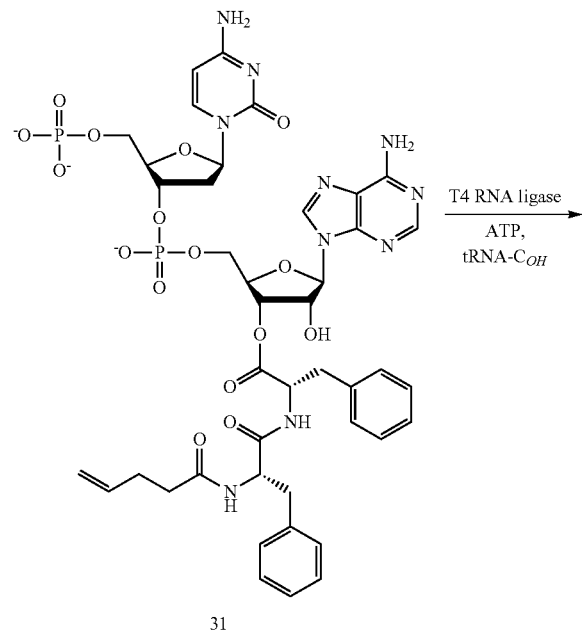
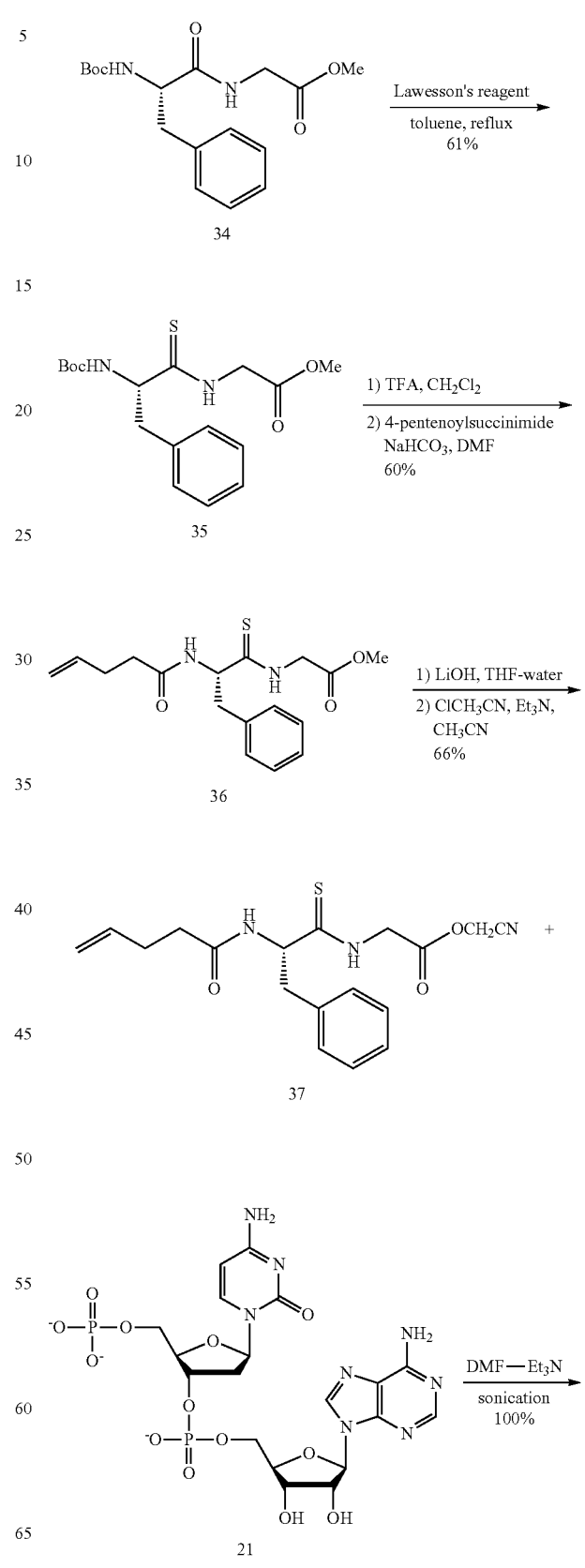
Scheme 5: Preparation of tRNA$_{CUA}$ activated with dipeptidomimetic 5.
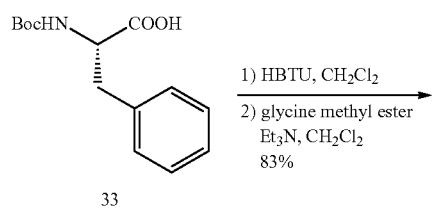

63
-continued
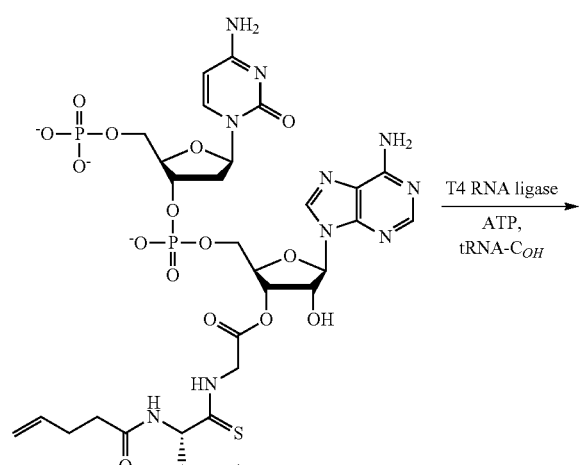
38
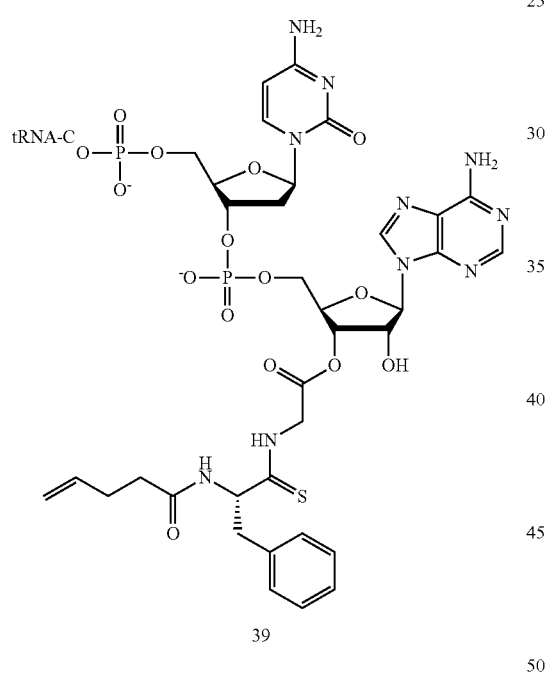
39
Scheme 6: Preparation of tRNA$_{CUA}$ activated with dipeptidomimetics 6 and 7
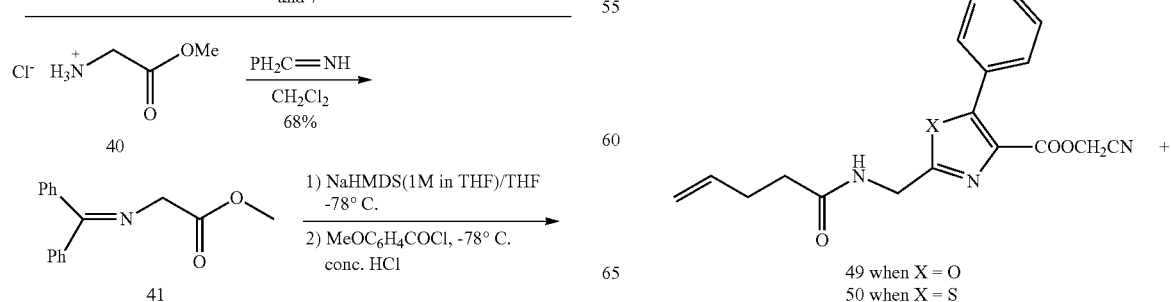
64
-continued
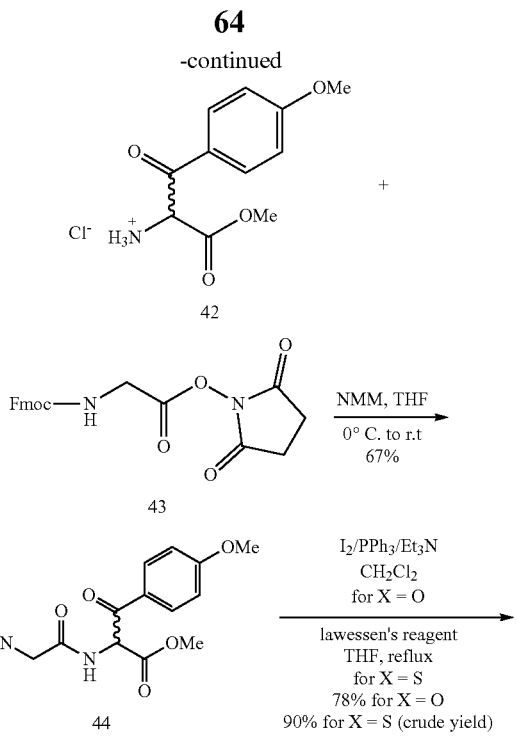
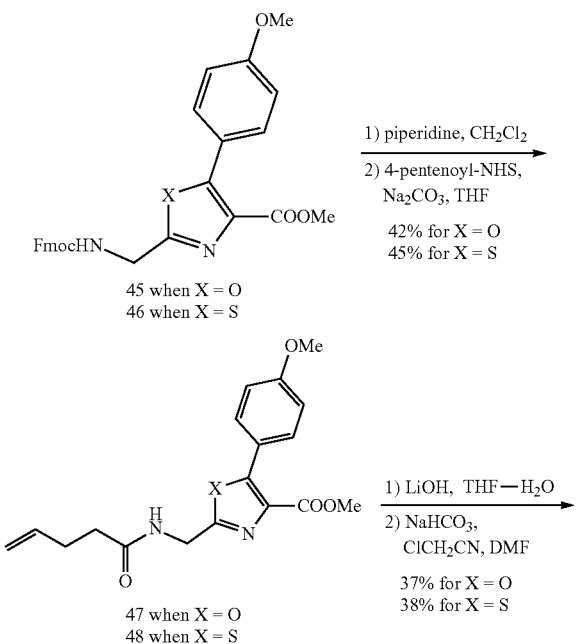
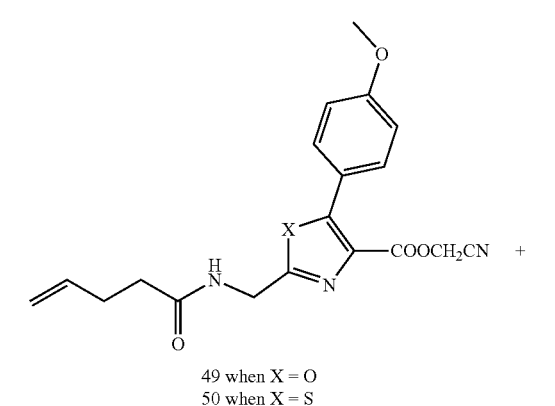

-continued
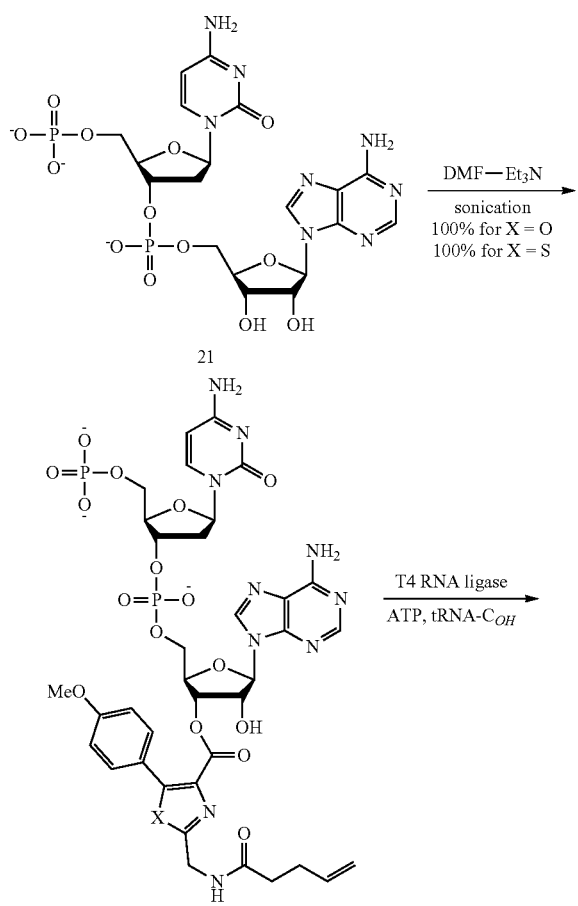
Scheme 7. Preparation of tRNA$_{CUA}$ activated with dipeptidomimetics 8 and 9
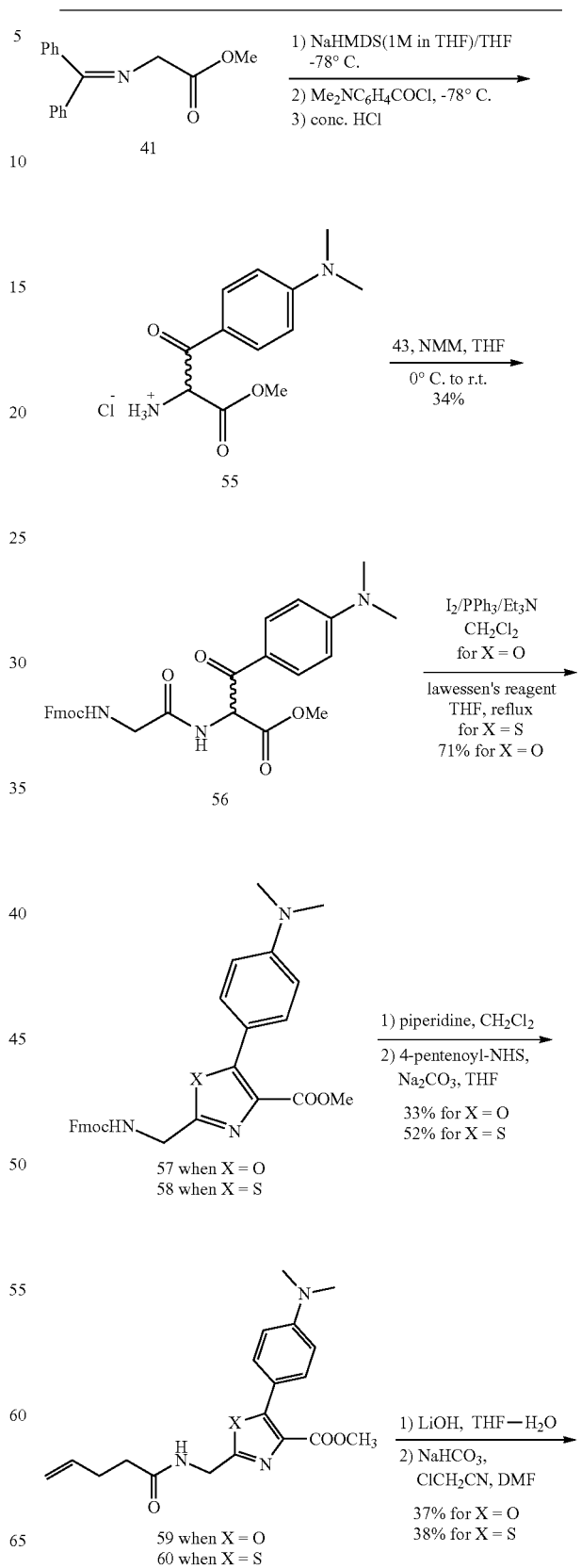

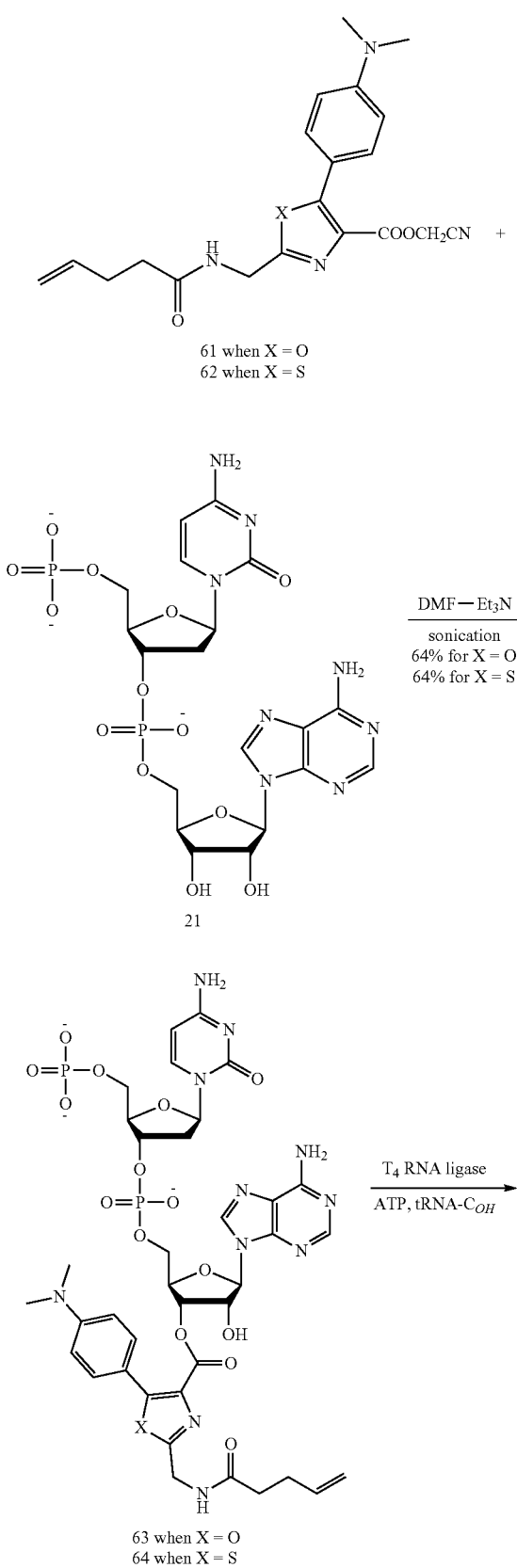
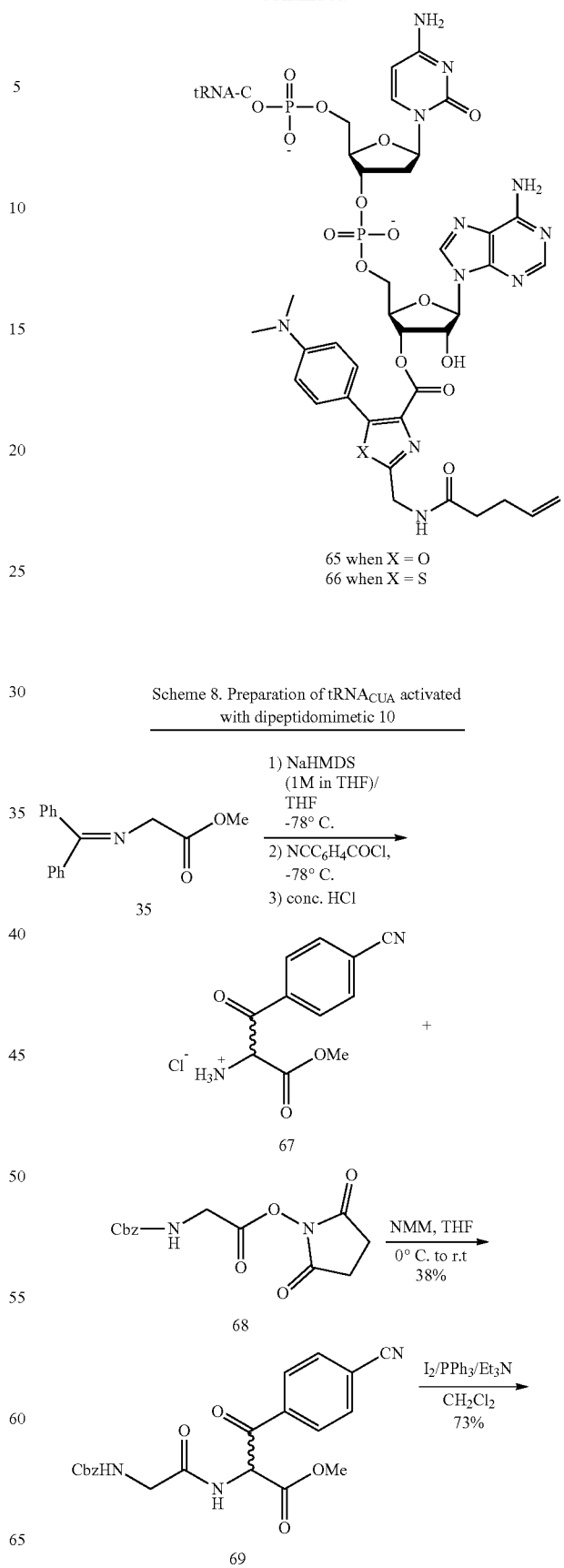

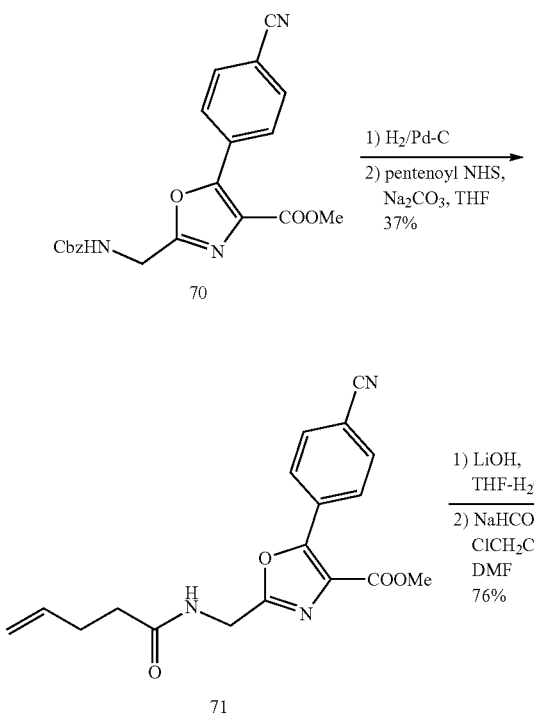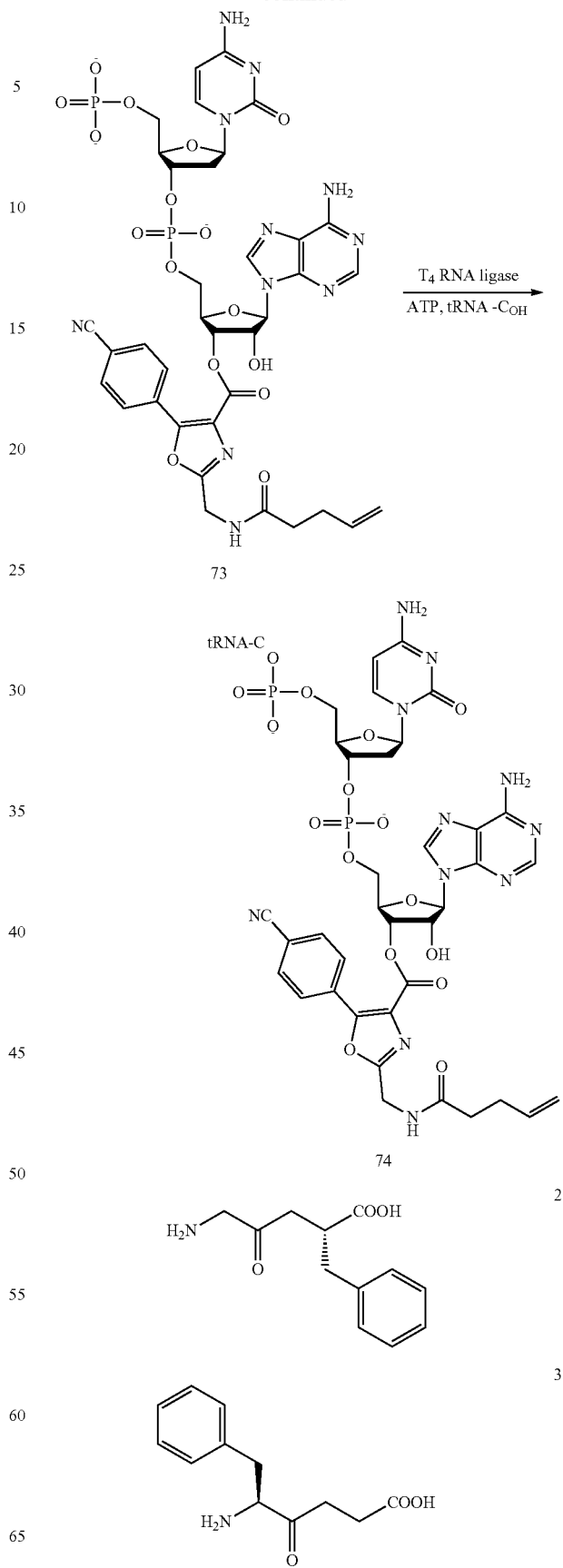

71
-continued
4
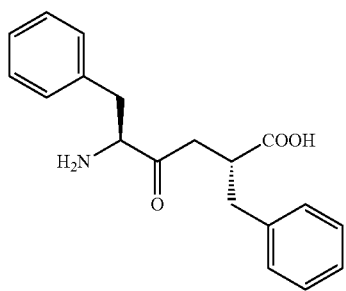
5
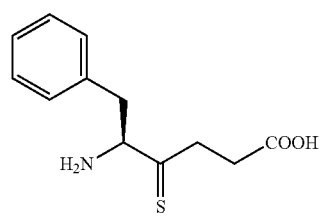
6
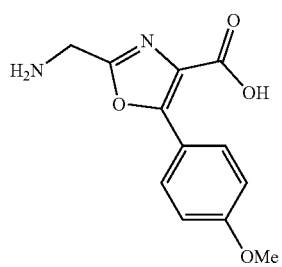
7
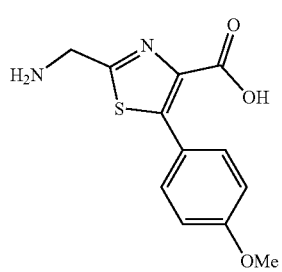
8
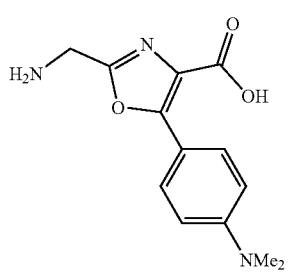
9
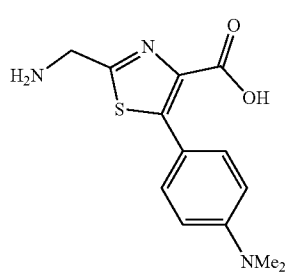
72
-continued
10
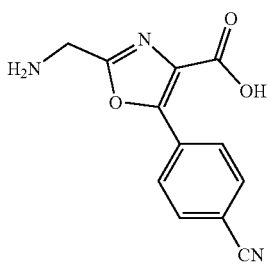
11
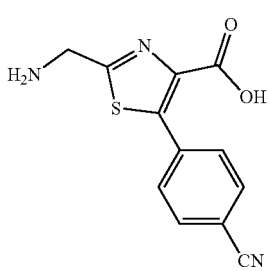
12
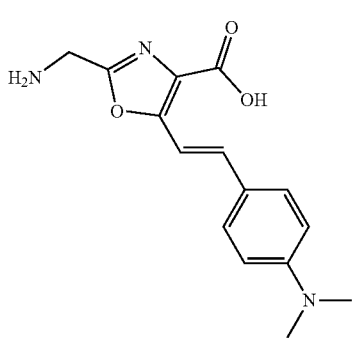
13
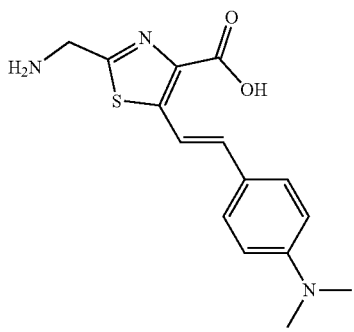
75
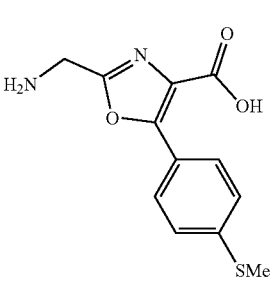

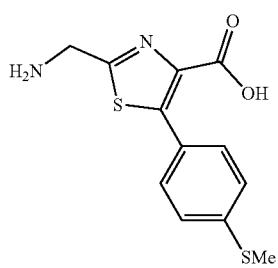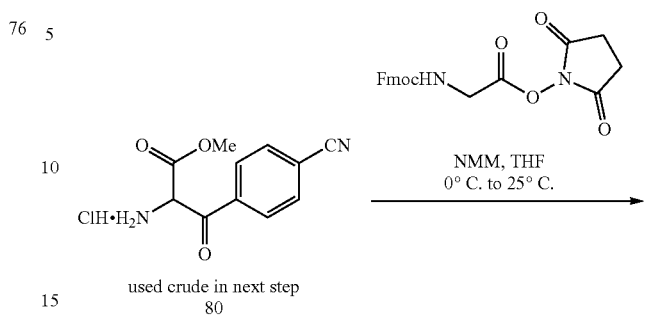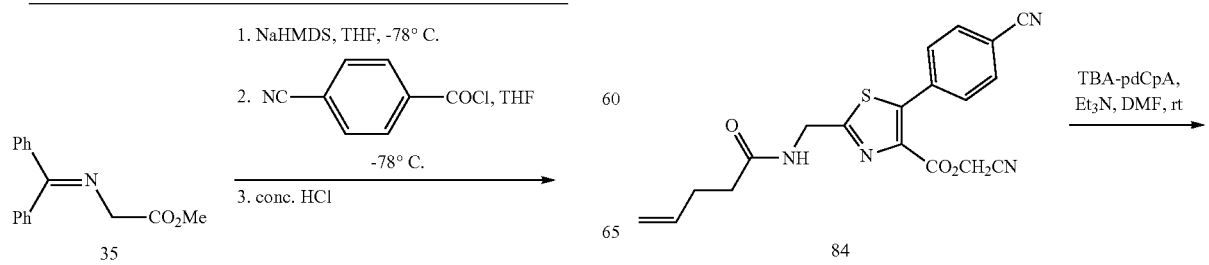

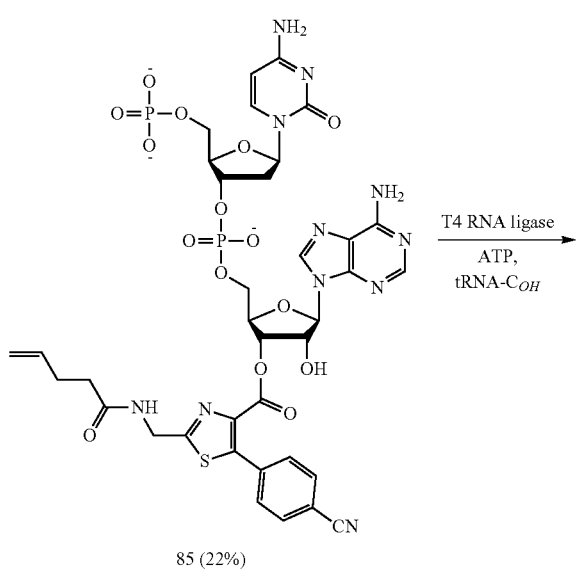
85 (22%)
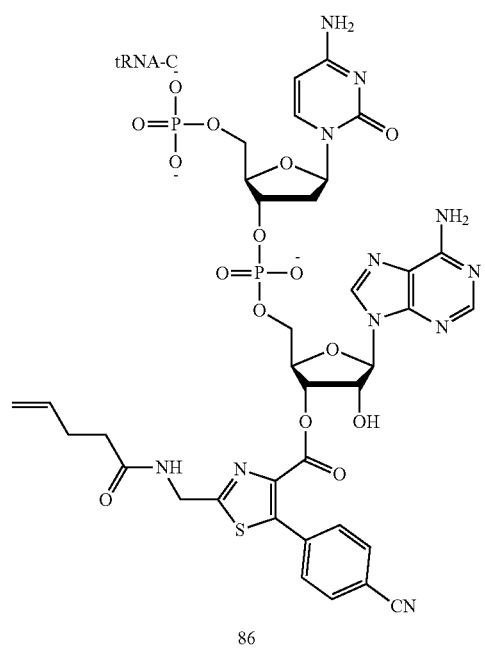
86
Scheme 10. Preparation of tRNA$_{CUA}$ activated with dipeptidomimetic 75
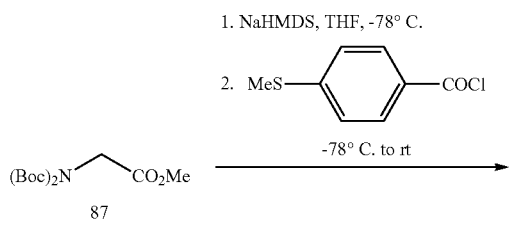
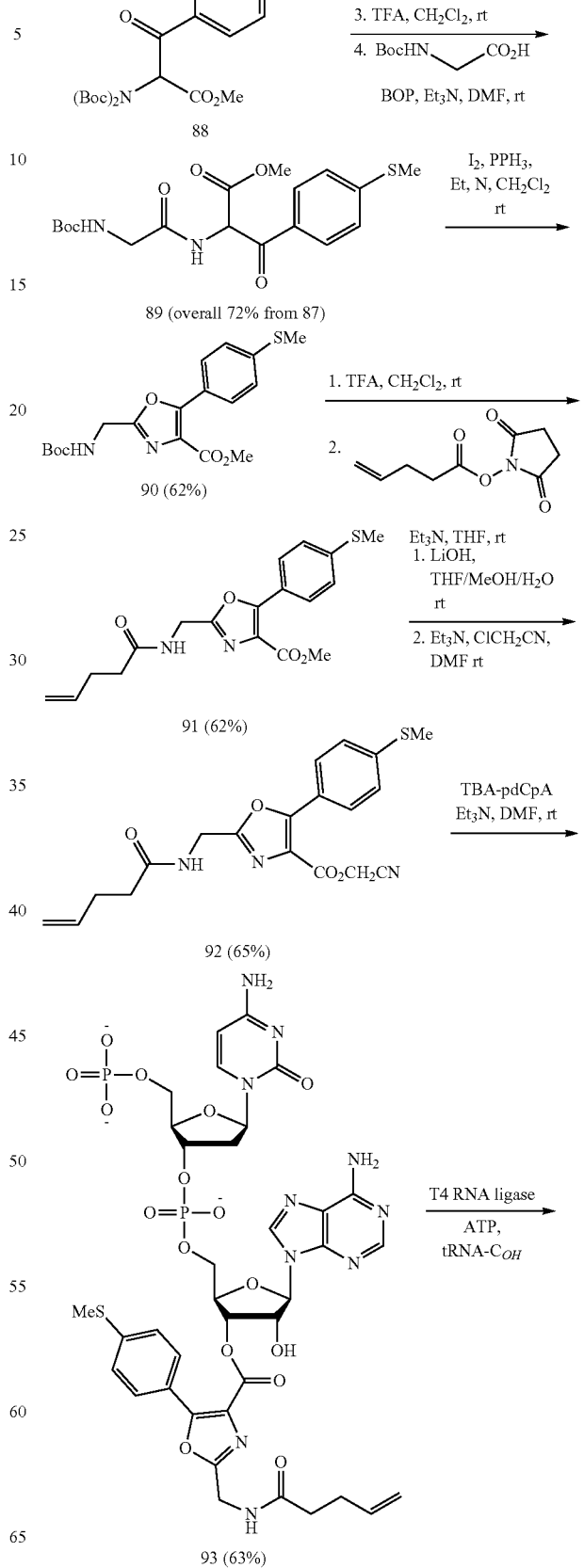
89 (overall 72% from 87)
90 (62%)
91 (62%)
92 (65%)
93 (63%)

Scheme 11. Preparation of tRNA$_{CUA}$ activated with dipeptidomimetic 76

Scheme 12. Preparation of tRNA<sub>CUA</sub> activated with dipeptidomimetic 77
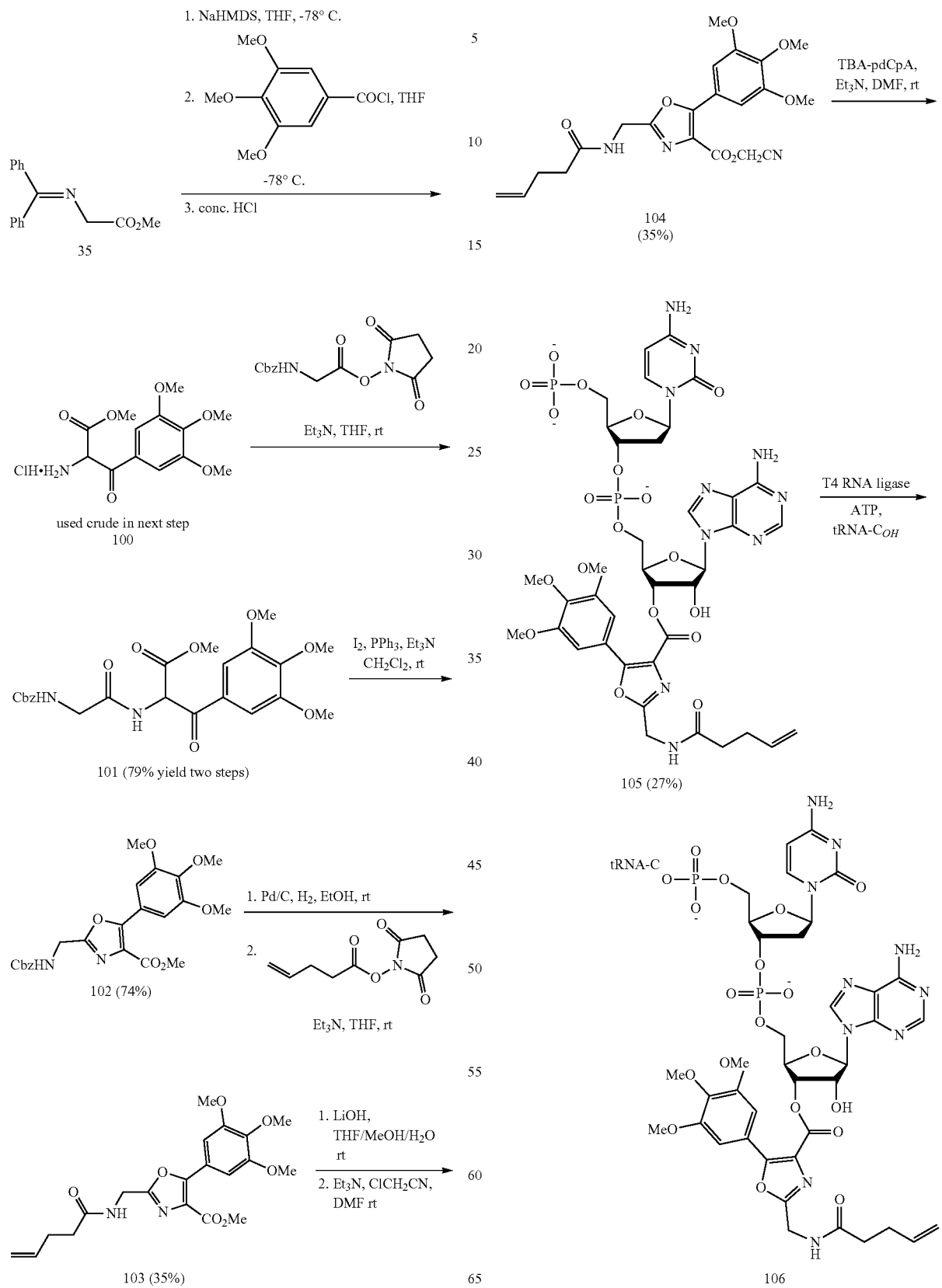

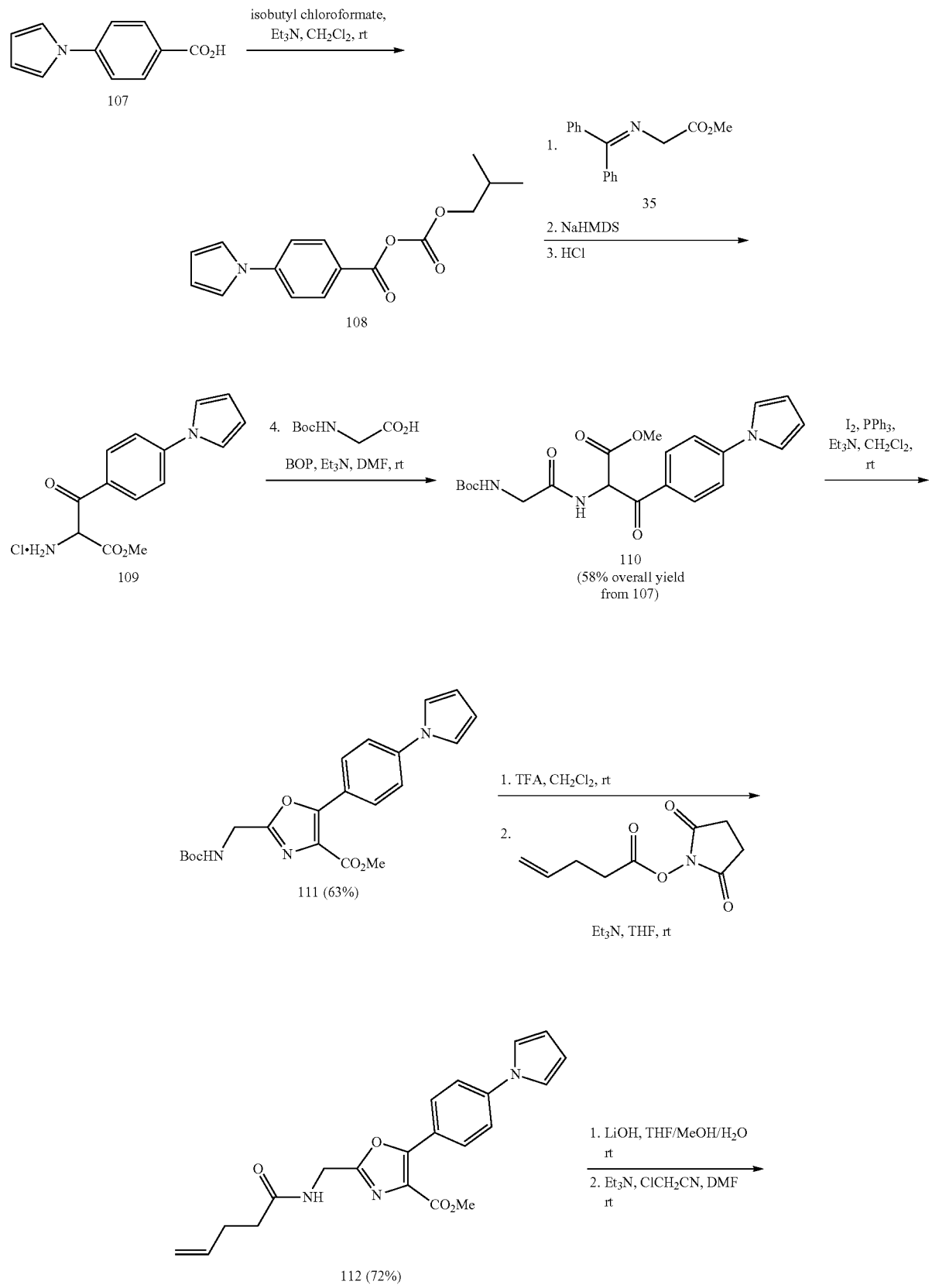

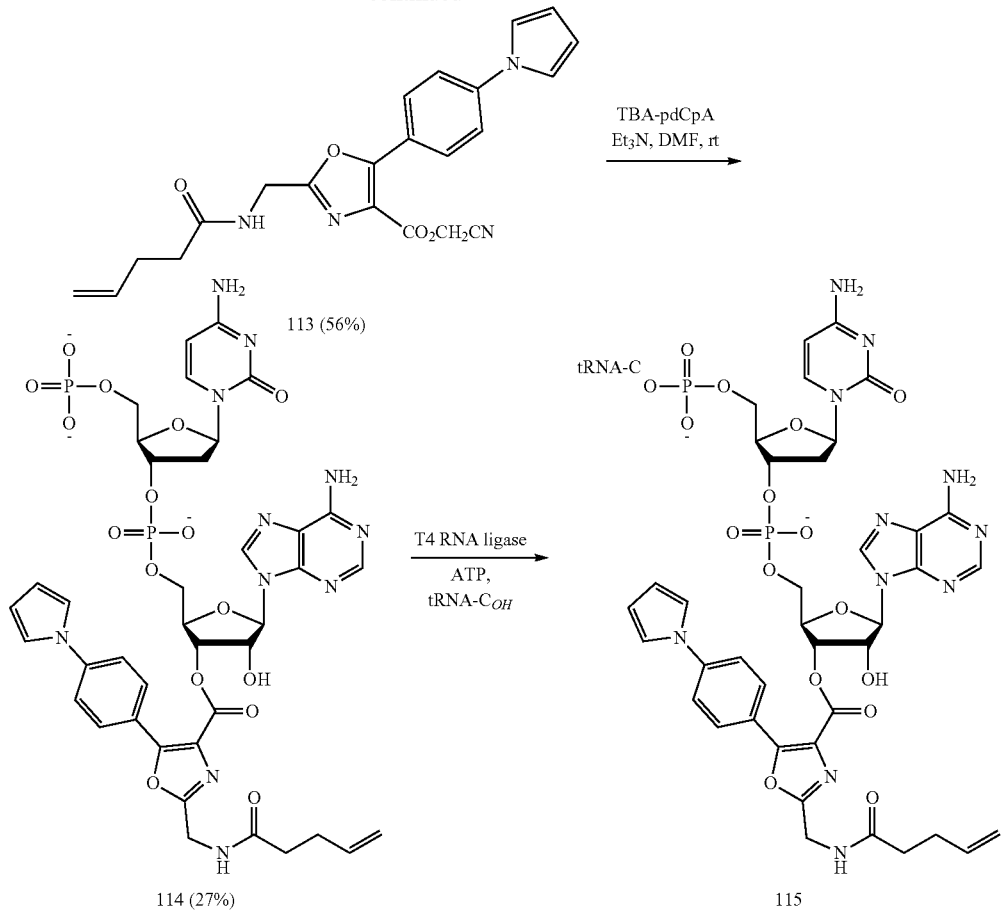
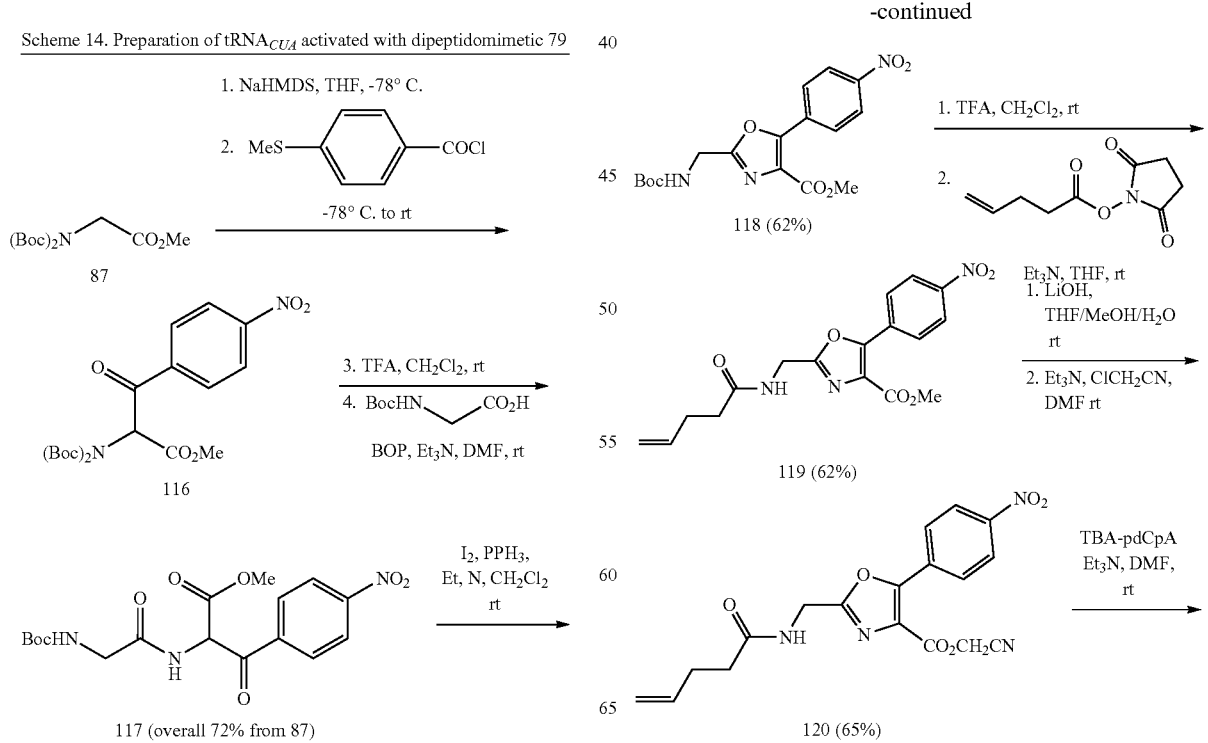

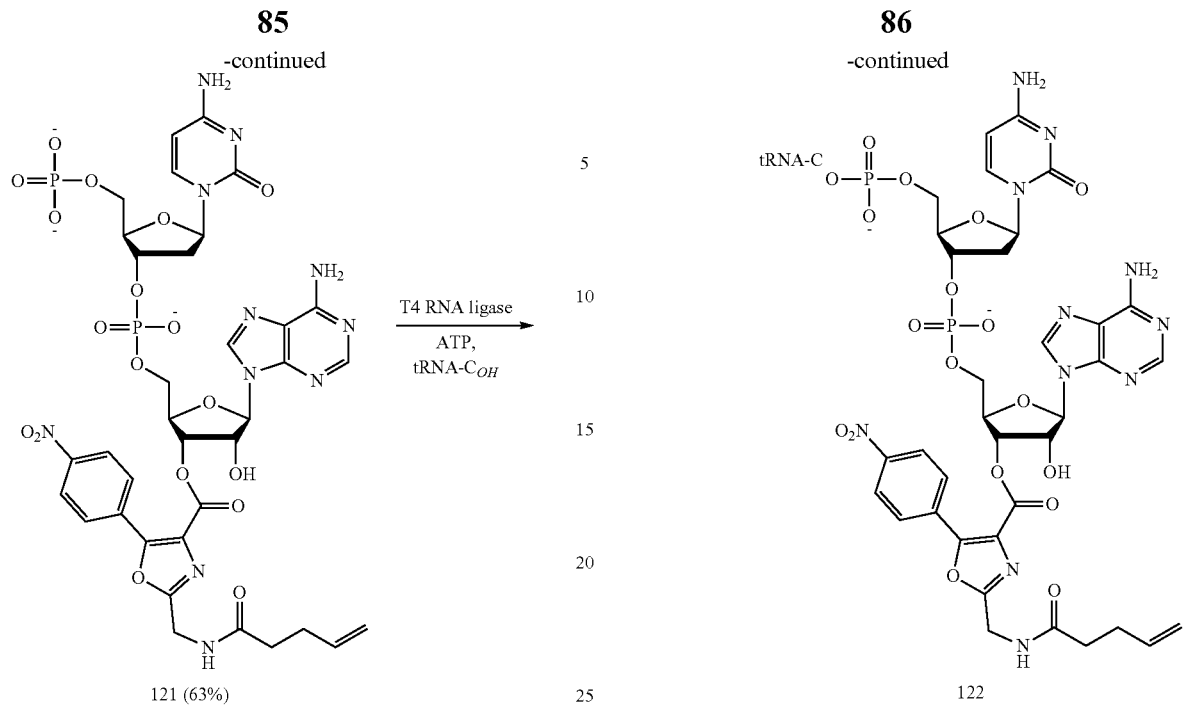
Scheme 15: Synthesis of suppressor tRNA$_{CUA}$ activated with five-membered ring lactam-constrained dipeptide amino acid analogue.
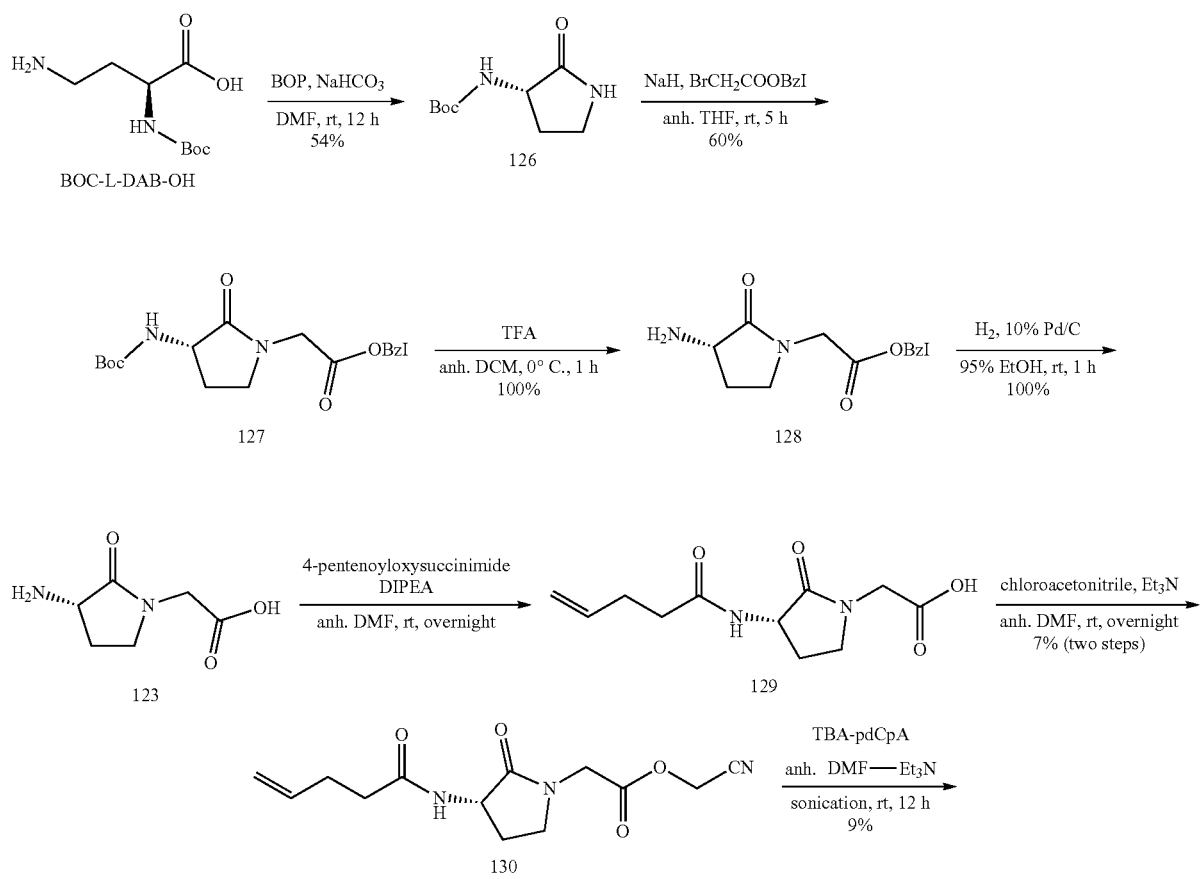

-continued
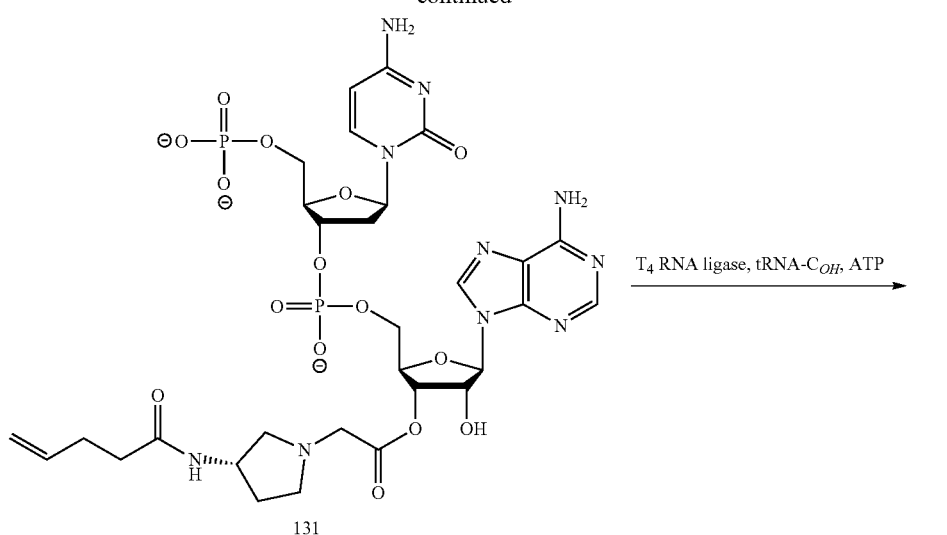
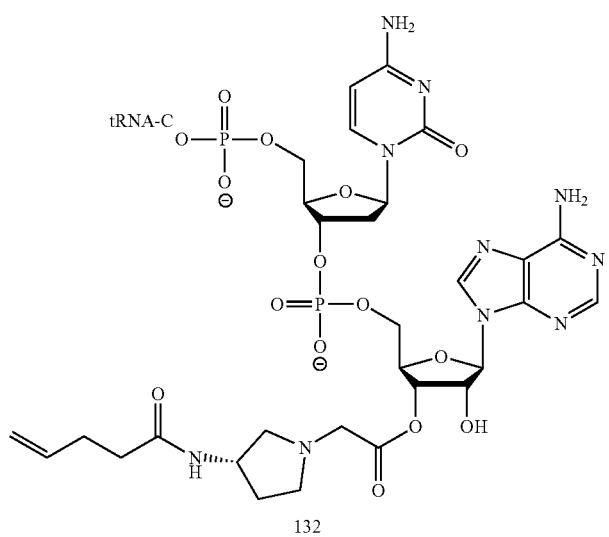
Scheme 16. Synthesis of suppressor tRNA$_{CUA}$ activated with six-membered ring lactam-constrained dipeptide amino acid analogue
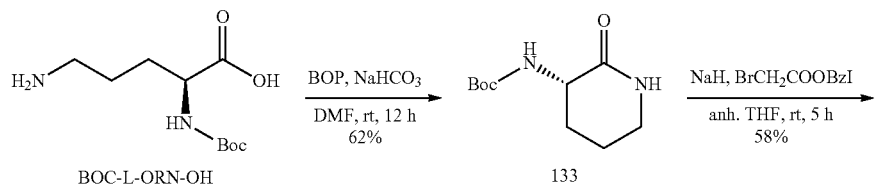
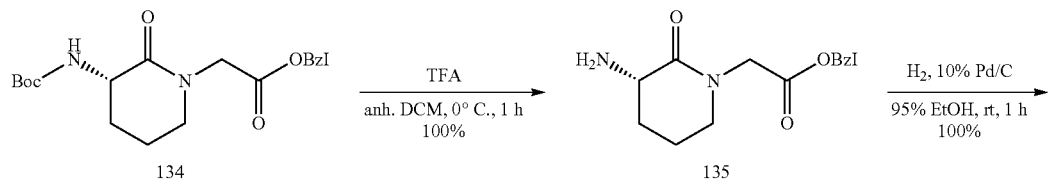

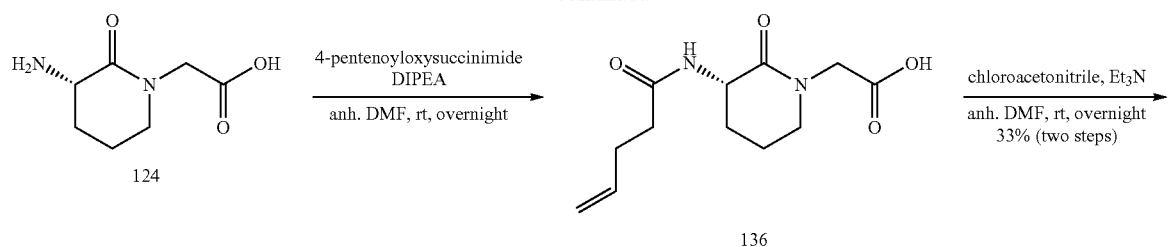
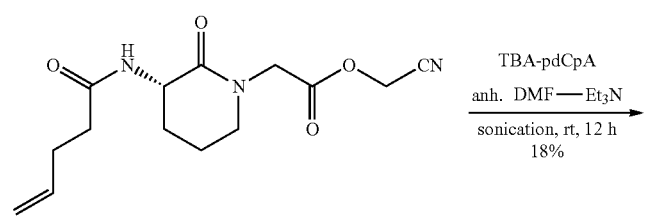
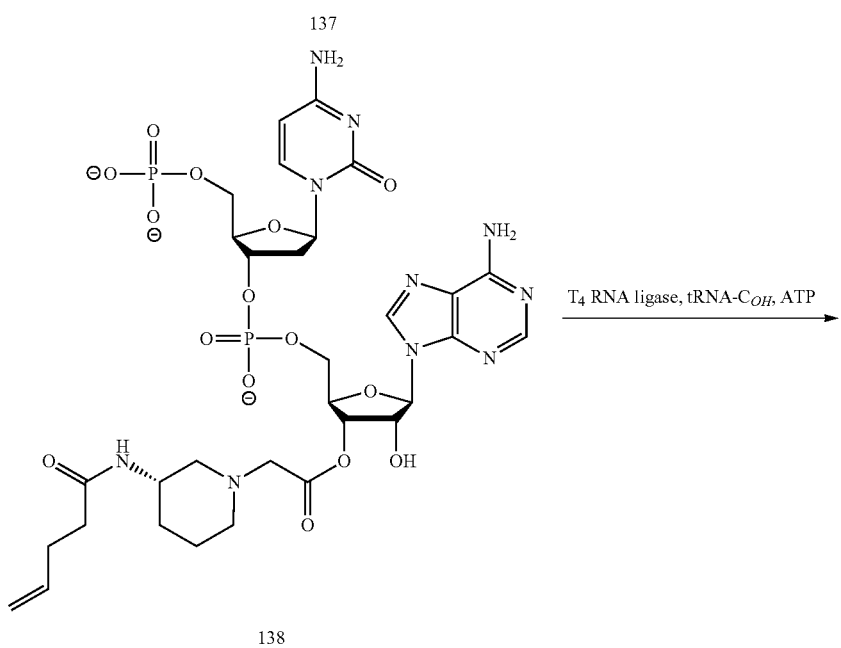
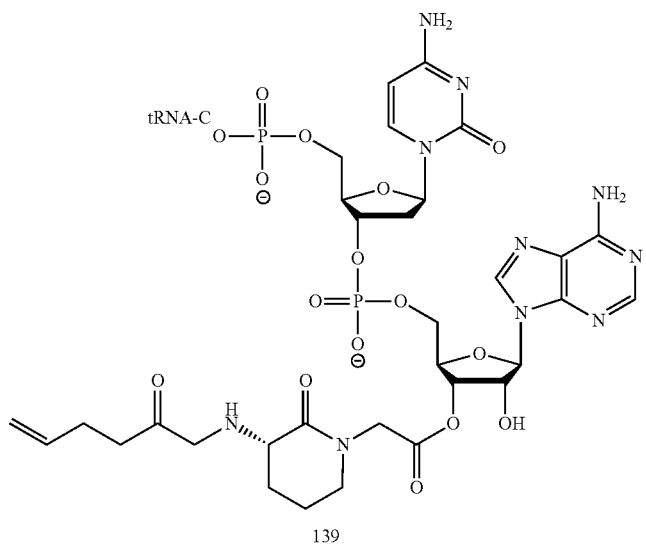

Scheme 17: Synthesis of suppressor tRNA$_{CUA}$ activated with seven-membered ring lactam-constrained dipeptide amino acid analogue
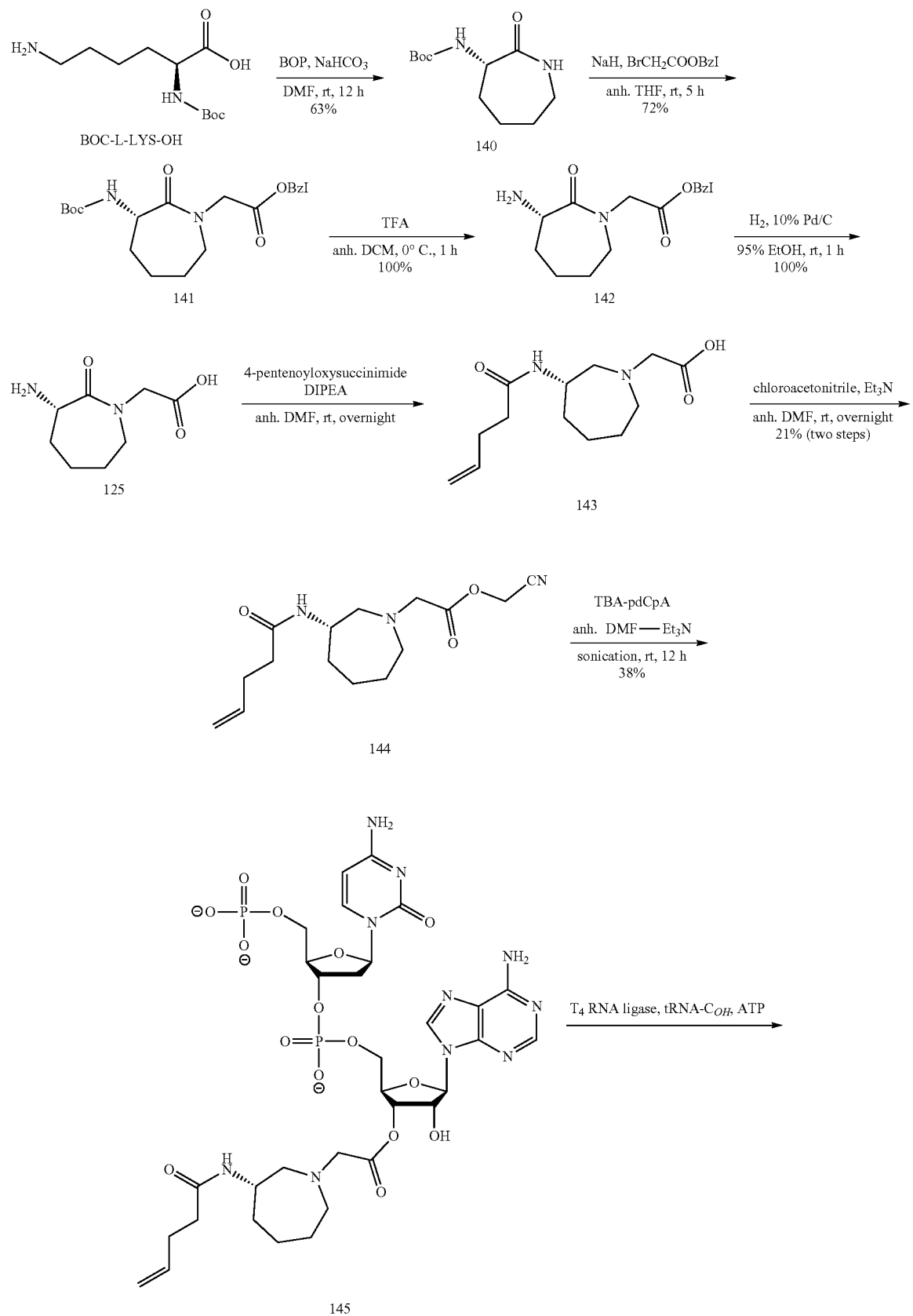

-continued

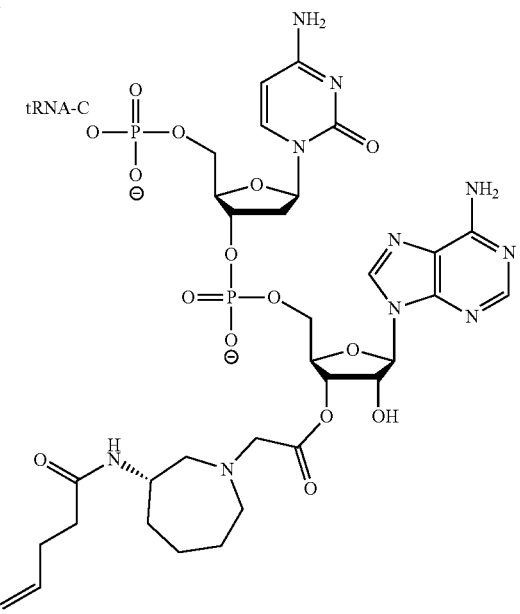

146

REFERENCES (1) Dedkova, L. M.; Fahmi, N. E.; Paul, R.; del Rosario, M.; Zhang, L.; Chen, S.; Feder, G.; Hecht, S. M. *Biochemistry* 2012, 51, 401.
(2) Maini, R.; Nguyen, D. T.; Chen, S.; Dedkova, L. M.; Chowdhury, S. R.; Alcala-Torano, R.; Hecht, S. M. *Bioorg. Med. Chem.* 2013, 21, 1088.
(3) Robertson, S. A.; Noren, C. J.; Anthony-Cahill, S. J.; Griffith, M. C.; Schultz, P. G. *Nucleic Acids Res.* 1989, 17, 9649.
(4) Lodder, M.; Golovine, S.; Hecht, S. M. *J. Org. Chem.* 1997, 62, 778.
(5) Lodder, M.; Golovine, S.; Laikhter, A. L.; Karginov, V. A.; Hecht, S. M. *J. Org. Chem.* 1998, 63, 794.
(6) Polacek, N.; Mankin, A. S. *Crit. Rev. Biochem. Mol. Biol.* 2005, 40, 285.
(7) Wang, B.; Zhou, J.; Lodder, M.; Anderson, R. D., 3rd; Hecht, S. M. *J. Biol. Chem.* 2006, 281, 13865.
(8) Huynh, M. L.; Russell, P.; Walsh, B. *Methods Mol. Biol.* 2009, 519, 507.

The embodiments described above are not intended to be limiting. All publications cited herein are incorporated by reference in their entirety.

What is claimed is:

1. An in vitro translation system comprising:

a transfer RNA (tRNA) comprising a modified dipeptidomimetic selected from

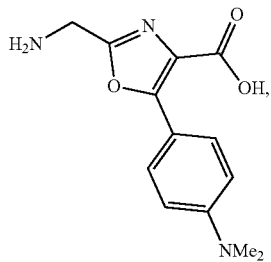

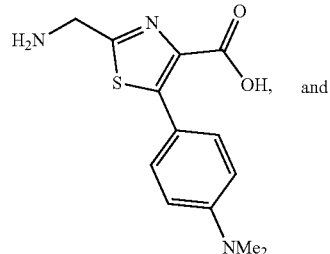

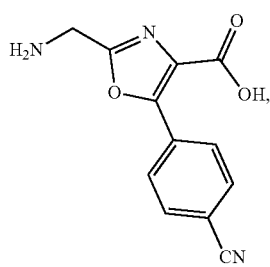

and a genetically modified *Escherichia coli* (*E. coli*) ribosome, the modification of the genetically modified ribosome consisting of: a 23S ribosomal RNA (rRNA) sequence consisting of a modified Region 1 (position 2057-2063) selected from UGCGUGG or AGCGUGA, and a modified Region 2 (position 2502-2507), wherein:

(a) if the modified Region 1 consists of UGCGUGG from position 2057-2063, the modified Region 2 is selected from the group consisting of ACGAAG, CGCACG, CUAUGU, CGCAAU, or CUACAG from position 2502-2507;

(b) if the modified Region 1 consists of AGCGUGA from position 2057-2063, the modified Region 2 is selected from the group consisting of CUGCGU, UGGCAG, AUCAGG, or AUCCGA from position 2502-2507.

2. The system of claim 1, comprising an *E. coli* S-30 extract.

3. A method for producing a modified peptide, polypeptide, or protein, comprising one or more of a modified dipeptidomimetic selected from

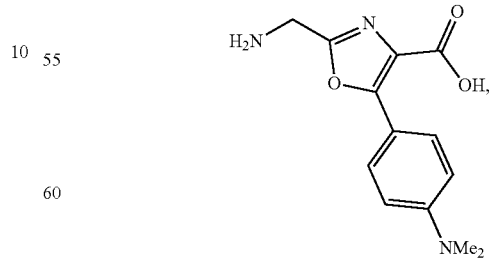

-continued

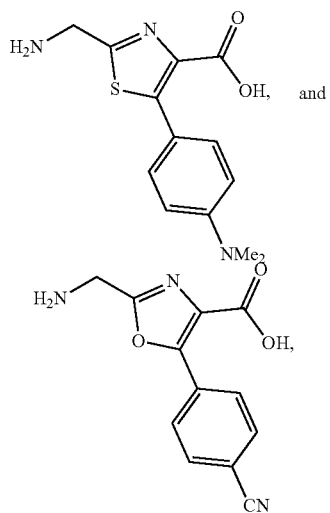

the method comprising:

providing to the in vitro translation system of claim 1:

(1) a messenger RNA (mRNA) encoding the modified peptide, polypeptide, or protein, wherein the mRNA encoding the modified peptide, polypeptide, or protein comprises at least one codon that recognizes an anticodon on the tRNA comprising the modified dipeptidomimetic; and (2) reagents sufficient to effect translation of the mRNA.

4. The method of claim 3, wherein the codon that recognizes the tRNA comprising the modified dipeptidomimetic comprises one or more stop codons, and wherein the tRNA comprising the modified dipeptidomimetic comprises one or more suppressor tRNA(s).

* * * * *

UNITED STATES PATENT AND TRADEMARK OFFICE
CERTIFICATE OF CORRECTION

PATENT NO. : 11,434,492 B2
APPLICATION NO. : 16/915362
DATED : September 6, 2022
INVENTOR(S) : Sidney Hecht et al.

Page 1 of 2

It is certified that error appears in the above-identified patent and that said Letters Patent is hereby corrected as shown below:

In the Specification

Column 11, Line 42, "THE-water" should be --THF-water--.

Column 13, Line 16, "THE" should be --THF--.

Column 13, Line 20, "THE" should be --THF--.

Column 17, Line 43, "aqueous 12 at" should be --aqueous $I_2$ at--.

Column 17, Line 54, "100 g/mL" should be --100 µg/mL--.

Column 24, Lines 54-55, "LPVPWPTLVTTFSYGVQ FSR" should be --LPVPWPTLVTTFSYGVQCFSR--.

Column 25, Line 3, "LPVPWPTLVTTFSGGVQ FSR" should be --LPVPWPTLVTTFSGGVQCFSR--.

Column 25, Line 7, "LPVPWPTLVTTFSxGVQ FSR" should be --LPVPWPTLVTTFSxGVQCFSR--.

Column 44, Line 19, "1%-+65%" should be --1%→65%--.

Column 45, Line 64, "(m, 11H)" should be --(m, 1H)--.

Column 45, Line 64, "dd, 11H" should be --dd, 1H--.

Column 46, Line 64, "1%-65%" should be --1%→65%--.

Column 49, Line 50, "1%-+65%" should be --1%→65%--.

Signed and Sealed this
First Day of November, 2022

Katherine Kelly Vidal
*Director of the United States Patent and Trademark Office*

CERTIFICATE OF CORRECTION (continued)
U.S. Pat. No. 11,434,492 B2

Column 52, Line 52, "haying" should be --having--.

Column 53, Line 6, "haying" should be --having--.